United States Patent [19]

Showalter et al.

[11] Patent Number: 4,556,654

[45] Date of Patent: Dec. 3, 1985

[54] ANTIMICROBIAL SUBSTITUTED ANTHRA[1,9-CD]PYRAZOL-6(2H)-ONES

[75] Inventors: Howard D. H. Showalter, Ann Arbor; Judith L. Johnson, Ypsilanti; Leslie M. Werbel; Edward F. Elslager, both of Ann Arbor, all of Mich.

[73] Assignee: Warner-Lambert Company, Morris Plains, N.J.

[21] Appl. No.: 507,961

[22] Filed: Jun. 28, 1983

[51] Int. Cl.[4] .................. A61K 31/415; A61K 31/445; C07D 401/12; C07D 231/54
[52] U.S. Cl. .................................... 514/222; 546/187; 546/199; 514/226; 548/181; 548/215; 514/227; 548/300; 514/253; 548/371; 548/372; 514/254; 514/256; 514/316; 514/322; 514/365; 514/374; 514/385; 514/403; 514/406; 544/55; 544/60; 544/96; 544/121; 544/122; 544/133; 544/137; 544/139; 544/140; 544/295; 544/296; 544/333; 544/357; 544/360; 544/364; 544/367; 544/369; 544/370; 544/371; 544/129
[58] Field of Search ............... 548/371, 372, 357, 181, 548/215, 300; 424/273 N; 564/464; 260/384, 383; 546/199, 187; 514/403, 322, 254, 256, 316, 253, 222, 226, 227, 365, 374, 385, 406; 544/133, 55, 60, 96, 121, 122, 129, 333, 360, 371, 137, 139, 140, 295, 296, 357, 364, 367, 369, 370

[56] References Cited

U.S. PATENT DOCUMENTS 3,471,485 10/1969 Trepanier ............................. 564/464
3,505,341 4/1970 Elslager ............................... 548/370

FOREIGN PATENT DOCUMENTS 817422 9/1937 France .
191142 8/1937 Switzerland .
1371644 10/1974 United Kingdom ................ 260/384

OTHER PUBLICATIONS

Ciba, Chem. Abst. 44, 9686d (1950).
Scalera, Chem. Abst., 51, 18630c (1957).
Akamatsu, Chem. Abst. 58, 4542a (1963).
Desai, Chem. Abst. 73, 4958y (1970).
Frass, Chem. Abst. 88, 113354d (1978).
Bradley and Bruce, "1:9-Pyrazoloanthrone", J. Chem. Soc., 1954, pp. 1894–1902 (1954).
Russell et al., Org. Magn. Resonance, 1969, 1(2), pp. 125–137.

*Primary Examiner*—Richard A. Schwartz
*Assistant Examiner*—Kurt G. Briscoe
*Attorney, Agent, or Firm*—Ronald A. Daignault

[57] ABSTRACT

Substituted anthra[1,9-cd]pyrazol-6(2H-ones have antimicrobial activity. Methods for their preparation, use and pharmaceutical compositions are disclosed.

26 Claims, No Drawings

ANTIMICROBIAL SUBSTITUTED ANTHRA[1,9-CD]PYRAZOL-6(2H)-ONES

CROSS-REFERENCE TO RELATED APPLICATION

This is a continuation-in-part of U.S. Ser. No. 401,157 filed July 23, 1982, now abandoned.

BACKGROUND OF THE INVENTION

Several 2,5 and 2,7-disubstituted anthra[1,9-cd]pyrazol-6(2H)-ones are disclosed in the prior literature. See for example J. Chem. Soc., 1630 (1952); J. Chem. Soc., 1894 (1954). Neither reference discloses any utility for these compounds.

SUMMARY OF THE INVENTION

The invention in its first generic chemical compound aspect is a compound having the structural formula

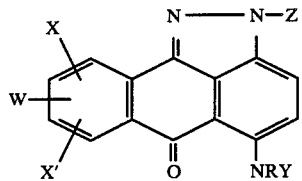

wherein X, X' and W may be the same or different and are hydrogen, hydroxy, alkoxy having one to four carbon atoms and chlorine; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an $NR_aR_a$ wherein $R_a$ may be the same or different and is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may be ethylene or may form

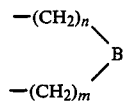

wherein n and m may be the same or different and are one, two, or three provided that the sum of n and m is an integer of from three to six, and B is a direct bond, O, S, or $N-R_4$ wherein $R_4$ is H or alkyl of from one to six carbon atoms; R and Y when taken together may be ethylene or may form

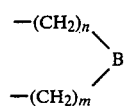

wherein n and m and B are defined above; Z is H, alkyl of from one to six carbon atoms which may be substituted with an $N(R_1)_2$, $SR_1$, or $OR_1$ group wherein $R_1$ is the same or different and is defined above, or $DNR_2R_3$ wherein D is straight or branched alkylene of from two to eight carbon atoms which may be substituted with an OH group and $R_2$ and $R_3$ are as defined above; and the pharmaceutically acceptable salts thereof; with the following provisos, (1) when X, X' and W are H and Z is H, R and Y when taken together do not complete a piperidine ring, (2) when X, X', and W are H and Z is $CH_3$, R and Y when taken together do not complete a piperidine ring or a morpholine ring.

The invention sought to be patented in its second generic chemical compound aspect is a compound having the structural formula

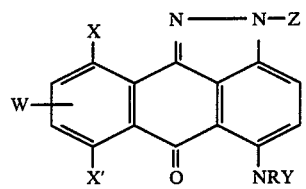

wherein X, X' and W may be the same or different and are H or OH, alkoxy having one to four carbon atoms or chlorine; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an $NR_aR_a$ wherein $R_a$ may be the same or different and is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may be ethylene or may form

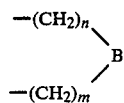

wherein n and m may be the same or different and are one, two, or three provided that the sum of n and m is an integer of from three to six, and B is a direct bond, O, S, or $N-R_4$ wherein $R_4$ is H or alkyl of from one to six carbon atoms; R and Y when taken together may be ethylene or may form

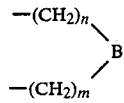

wherein n, m, and B are defined above; Z is H, alkyl of from one to six carbon atoms which may be substituted with an $N(R_1)_2$, $SR_1$, or $OR_1$ group wherein $R_1$ is the same or different and is defined above, or $DNR_2R_3$ wherein D is straight or branched alkylene of from two to eight carbon atoms which may be substituted with an OH group and $R_2$ and $R_3$ are as defined above; and the pharmaceutically acceptable salts thereof; with the following provisos, (1) when X, X', and W are H and Z is H, R and Y when taken together do not complete a piperidine ring, (2) when X, X', and W are H and Z is CH₃ R and Y when taken together do not complete a piperidine ring or a morpholine ring.

The invention sought to be patented in its third generic chemical compound aspect is a compound having the structural formula

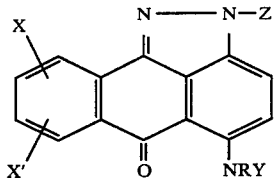

wherein X and X' may be the same or different and are H, OH, alkoxy of one to four carbon atoms or chlorine; R is H or alkyl of from one to six carbon atoms; Y is H, alkyl of from one to six carbon atoms which may be substituted with an OR₁ group wherein R₁ is H or alkyl of from one to six carbon atoms, or ANR₂R₃ wherein A is alkylene of from two to 11 carbon atoms, R₂ and R₃ may be the same or different and are H, alkyl of from one to six carbon atoms which may be substituted with OH or an NRaRa wherein Ra is H or alkyl of from one to three carbon atoms which may be substituted with OH, or NR$_b$R$_b$ wherein R$_b$ is the same or different and is H or alkyl of from one to three carbon atoms, or R₂ and R₃ when taken together may be ethylene or may form

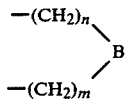

wherein n, m, and B are defined above; Z is H, alkyl of from one to six carbon atoms which may be substituted with an N(R₁)₂, SR₁, or OR₁ group wherein R₁ is defined above, or DNR₂R₃ wherein D is alkylene of from two to 11 carbon atoms which may be substituted with an OH group and R₂ and R₃ are as defined above; and the pharmaceutically acceptable salts thereof; with the following provisos, (1) when X is H and Z is H, R and Y when taken together do not complete a piperidine ring, (2) when X is H and Z is CH₃ R and Y when taken together do not complete a piperidine ring or a morpholine ring.

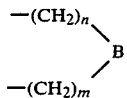

wherein n, m, and B are defined above; Z is H, alkyl of from one to six carbon atoms which may be substituted with an N(R₁)₂, SR₁, or OR₁ group wherein R₁ is defined above, or DNR₂R₃ wherein D is alkylene of from two to 11 carbon atoms which may be substituted with an OH group and R₂ and R₃ are as defined above; and the pharmaceutically acceptable salts thereof; with the following provisos, (1) when X is H and Z is H, R and Y when taken together do not complete a piperidine ring, (2) when X is H and Z is CH₃ R and Y when taken together do not complete a piperidine ring or a morpholine ring.

The invention in its fourth generic chemical compound aspect is a compound having the structural formula I

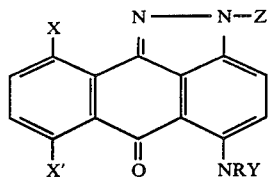

wherein X, and X' may be the same or different and are H or OH; R is H or alkyl of from one to six carbon atoms; Y is H, alkyl of from one to six carbon atoms which may be substituted with an OR₁ group wherein R₁ is H or alkyl of from one to six carbon atoms, or ANR₂R₃ wherein A is straight or branched alkylene of from two to eight carbon atoms, R₂ and R₃ may be the same or different and are H, alkyl of from one to six carbon atoms which may be substituted with OH or an NRaRa wherein Ra is the same or different and as H or alkyl of from one to three carbon atoms which may be substituted with OH, or NR$_b$R$_b$ wherein R$_b$ is the same or different and is H or alkyl of from one to three carbon atoms, or R₂ and R₃ when taken together may be ethylene or may form

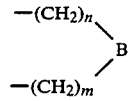

and m is an integer of from three to six, and B is a direct bond, O, S, or N-R₄ wherein R₄ is H or alkyl of from one to six carbon atoms; R and Y when taken together may be ethylene or may form

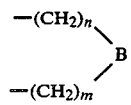

wherein n, m, and B are defined above; Z is H, alkyl of from one to six carbon atoms which may be substituted with an N(R₁)₂, SR₁, or OR₁ group wherein R₁ is the same or different and is as defined above, or DNR₂R₃ wherein D is straight or branched alkylene of from two to eight carbon atoms which may be substituted with an OH group and R₂ and R₃ are as defined above; and the pharmaceutically acceptable salts thereof; with the following provisos, (1) when X and X' are H and Z is H, R, and Y when taken together do not complete a piperidine ring, (2) when X and X' are H and Z is CH₃, R and Y when taken together do not complete a piperidine ring or a morpholine ring.

The invention in a first subgeneric aspect of its fourth chemical compound aspect is a chemical compound having structural formula I wherein X and X' are OH; and the pharmaceutically acceptable salts thereof.

The invention in a second subgeneric aspect of its fourth chemical compound aspect is a chemical compound having structural formula I wherein X and X' are H; and the pharmaceutically acceptable salts thereof.

The invention in a third subgeneric aspect of its fourth chemical compound aspect is a chemical compound having structural formula I wherein A and D are the same or different and are ethylene or propylene; and the pharmaceutically acceptable salts thereof.

The invention in a fourth subgeneric aspect of its fourth chemical compound aspect is a compound having structural formula I′

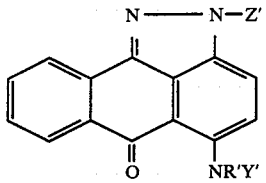

wherein R′ is H or alkyl of from 1 to 6 carbon atoms; Y′ is $CH_2CH_2NHCH_2CH_2OH$ when Z′ is alkyl of from one to four carbon atoms which may be substituted with an $SR_1'$, or $OR_1'$ group wherein $R_1'$ is H or alkyl of from one to four carbon atoms or $D'NR_2'R_3'$ wherein D′ is straight or branched alkylene of from two to four carbon atoms which may be substituted with an OH group and $R_2'$ and $R_3'$ may be the same or different and are H, alkyl of from one to six carbon atoms which may be substituted with an OH or $R_2'$ and $R_3'$ when taken together may be ethylene or may form

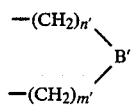

wherein n′ and m′ may be the same or different and are one or two provided that the sum of n′ and m′ is three or four, and B′ is a direct bond, O, S, or $N-R_4'$ wherein $R_4'$ is H or alkyl of from one to four carbon atoms; or Z′ is $CH_2CH_2NHCH_2CH_2OH$ when Y′ is H, alkyl of from one to six carbon atoms which may be substituted with an $OR_1'$ group wherein $R_1'$ is defined above or $A'NR_1'R_2'$ wherein A′ is alkylene of from two to four carbon atoms and $R_1'$ and $R_2'$ are as defined above; and the pharmaceutically acceptable salts thereof.

The invention in a fifth subgeneric aspect of its fourth chemical compound aspect is a compound having structural formula I″

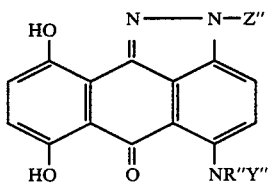

wherein R″ is H or alkyl of from one to six carbon atoms; Y″ is H, alkyl of from one to six carbon atoms which may be substituted with an $OR_1''$ group wherein $R_1''$ is H or alkyl of from one to four carbon atoms, or $A''NR_2''R_3''$ wherein A″ is alkylene of from two to four carbon atoms, $R_2''$ and $R_3''$ may be the same or different and are H, alkyl of from one to six carbon atoms which may be substituted with an OH or an $NRa''Ra''$ wherein Ra″ is the same or different and is H or alkyl of from one to three carbon atoms which may be substituted with an OH or $R_2''$ and $R_3''$ when taken together may be ethylene or may form

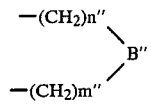

wherein n″ and m″ may be the same or different and are one or two provided that the sum of n″ and m″ is three or four, and B″ is a direct bond, O, S, or $N-R_4''$ wherein $R_4''$ is H or alkyl of from one to four carbon atoms; Z″ is alkyl of from one to four carbon atoms which may be substituted with an $SR_1''$, or $OR_1''$ group wherein $R_1''$ is defined above, or $D''NR_2''R_3''$ wherein D″ is alkylene of from two to four carbon atoms which may be substituted with an OH group and $R_2''$ and $R_3''$ are as defined above; and the pharmaceutically acceptable salts thereof.

The invention in a sixth subgeneric aspect of its second chemical compound aspect is a compound having the structural formula I‴

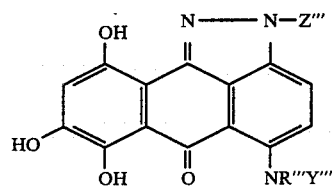

wherein R‴ is H or alkyl of from one to six carbon atoms; Y‴ is H, alkyl of from one to six carbon atoms which may be substituted with an $OR_1'''$ group wherein $R_1'''$ is H or alkyl of from one to four carbon atoms, or $A'''NR_2'''R_3'''$ wherein A‴ is alkylene of from two to four carbon atoms, $R_2'''$ and $R_3'''$ may be the same or different and are H, alkyl of from one to six carbon atoms which may be substituted with an OH or an $NRa'''Ra'''$ wherein Ra‴ is the same or different and is H or alkyl of from one to three carbon atoms which may be substituted with an OH or $R_2'''$ and $R_3'''$ when taken together may be ethylene or may form

wherein n‴ and m‴ may be the same or different and are one or two provided that the sum of n‴ and m‴ is three or four, and B‴ is a direct bond, O, S, or $N-R_4'''$ wherein $R_4'''$ is H or alkyl of from one to four carbon atoms; Z‴ is alkyl of from one to four carbon atoms which may be substituted with an $SR_1'''$, or $OR_1'''$ group wherein $R_1'''$ is defined above, or $D'''NR_2'''R_3'''$ wherein D‴ is alkylene of from two to four carbon atoms which may be substituted with an OH group and $R_2'''$ and $R_3'''$ are as defined above; and the pharmaceutically acceptable salts thereof.

The invention in a seventh subgeneric aspect of its fourth chemical compound aspect is a compond having the structural formula I″″

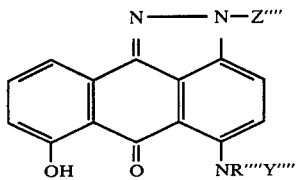

wherein R'''' is H or alkyl of from one to six carbon atoms; Y'''' is H, alkyl of from one to six carbon atoms which may be substituted with an OR$_1$'''' group wherein R$_1$'''' is H or alkyl of from one to four carbon atoms, or A''''NR$_2$''''R$_3$'''' wherein A'''' is alkylene of from two to four carbon atoms, R$_2$'''' and R$_3$'''' may be the same or different and are H, alkyl of from one to six carbon atoms which may be substituted with an OH or an NRa''''Ra'''' wherein Ra'''' is the same or different and is H or alkyl of from one to three carbon atoms which may be substituted with an OH or R$_2$'''' and R$_3$'''' when taken together may be ethylene or may form

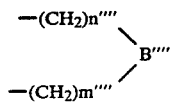

wherein n'''' and m'''' may be the same or different and are one or two provided that the sum of n'''' and m'''' is three or four, and B'''' is a direct bond, O, S, or N-R$_4$'''' wherein R$_4$'''' is H or alkyl of from one to four carbon atoms; Z'''' is alkyl of from one to four carbon atoms which may be substituted with an SR$_1$'''', or OR$_1$'''' group wherein R$_1$'''' is defined above, or D''''NR$_2$''''R$_3$'''' wherein D'''' is alkylene of from two to four carbon atoms which may be substituted with an OH group and R$_2$'''' and R$_3$'''' are as defined above; and the pharmaceutically acceptable salts thereof.

The invention in an eighth subgeneric aspect of its fourth chemical compound aspect is a compound having the structural formula I$^v$

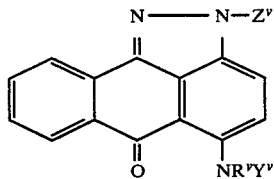

wherein R$^v$ is H or alkyl of from one to six carbon atoms; Y$^v$ is H, alkyl of from one to four carbon atoms or A$^v$NR$_2$$^v$R$_3$$^v$ wherein A$^v$ is alkylene of from two to four carbon atoms, R$_2$ and R$_3$ may be the same or different and are H or alkyl of from one to six carbon atoms which may be substituted with an OH or R$_2$$^v$ and R$_3$$^v$ when taken together may be ethylene or may form

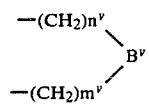

wherein n$^v$ and m$^v$ may be the same or different and are one or two provided that the sum of n$^v$ and m$^v$ is three or four, and B$^v$ is a direct bond, O, S, or NR$_4$$^v$ wherein R$_4$$^v$ is H or alkyl of from one to four carbon atoms; Z$^v$ is alkyl of from one to four carbon atoms, which may be substituted with an SR$_1$$^v$, or OR$_1$$^v$ group wherein R$_1$$^v$ is H or alkyl of from one to four carbon atoms, or D$^v$NR$_2$$^v$R$_3$$^v$ wherein D$^v$ is alkylene of from two to four carbon atoms which may be substituted with an OH group and R$_2$$^v$ and R$_3$$^v$ are defined above; and the pharmaceutically acceptable salts thereof.

The invention in a ninth subgeneric aspect of its fourth chemical compound aspect is a compound having the structural formula I$^{vi}$

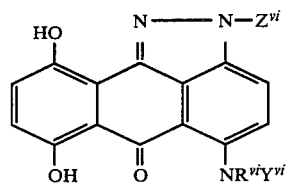

wherein R$^{vi}$ is H or alkyl of from one to six carbon atoms; Y$^{vi}$ is H, alkyl of from one to four carbon atoms which may be substituted with an OR$_1$$^{vi}$ group wherein R$_1$$^{vi}$ is H or alkyl of from one to four carbon atoms or A$^{vi}$NR$_2$$^{vi}$R$_3$$^{vi}$ wherein A$^{vi}$ is alkylene of from two to four carbon atoms R$_2$$^{vi}$ and R$_3$$^{vi}$ may be the same or different and are alkyl of from one to six carbon atoms which may be substituted with an OH, or R$_2$$^{vi}$ and R$_3$$^{vi}$ when taken together may be ethylene or may form

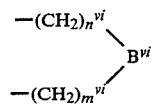

wherein n$^{vi}$ and m$^{vi}$ may be the same or different and are one or two provided that the sum of n$^{vi}$ and m$^{vi}$ is three or four, and B$^{vi}$ is a direct bond, O, S, or NR$_4$$^{vi}$ wherein R$_4$$^{vi}$ is H or alkyl of from one to four carbon atoms; Z$^{vi}$ is D$^{vi}$NR$_2$$^{vi}$R$_3$$^{vi}$ wherein D$^{vi}$ is alkylene of from two to four carbon atoms, R$_2$$^{vi}$ and R$_3$$^{vi}$ are defined above; and the pharmaceutically acceptable salts thereof.

The invention as species of the first generic chemical compound aspect of the invention are the chemical compounds having the following names:

2-[2-(diethylamino)ethyl)]-5-[[2-[(2-hydroxyethyl)amino]ethyl]amino]anthra[1,9-cd]pyrazol-6(2H)-one;

2-[2-[(2-hydroxyethyl)amino]ethyl]-5-[[2-[(2-hydroxyethyl)amino]ethyl]amino]anthra[1,9-cd]pyrazol-6(2H)-one;

5-[(2-aminoethyl)amino]-2-[2-[(2-hydroxyethyl)amino]ethyl]anthra[1,9-cd]pyrazol-6(2H)-one;

2-[2-(diethylamino)ethyl]-7,10-dihydroxy-5-[[2-[(2-hydroxyethyl)amino]ethyl]amino]anthra[1,9-cd]pyrazol-6(2H)-one;

5-[[2-[(2-hydroxyethyl)amino]ethyl]amino]-7,10-dihydroxy-2-(2-hydroxyethyl)anthra[1,9-cd]pyrazol-6(2H)-one;

2-[2-[[2-(dimethylamino)ethyl]amino]ethyl]-5-[[2-[(2-hydroxyethyl)amino]ethyl]amino]-7,10-dihydroxyanthra[1,9-cd]pyrazol-6(2H)-one;

2-[2-(diethylamino)ethyl]-[[2-(4-morpholinyl)ethyl)]amino]anthra[1,9-cd]pyrazol-6(2H)-one;

2-(2-aminoethyl)-5-[[2-[(2-hydroxyethyl)amino]ethyl]amino]anthra[1,9-cd]pyrazol-6(2H)-one;

5-[(2-aminoethyl)amino]-2-[2-(diethylamino)ethyl]-7,10-dihydroxyanthra[1,9-cd]pyrazol-6(2H)-one;

2-[2-(diethylamino)ethyl]-7,10-dihydroxy-5-[[2-(methylamino)ethyl]amino]anthra[1,9-cd]pyrazol-6(2H)-one;

2-[2-(dimethylamino)ethyl]-7,10-dihydroxy-5-[[2-[(2-hydroxyethyl)amino]ethyl]amino]anthra[1,9-cd]pyrazol-6(2H)-one;

5-[(2-aminoethyl)amino]-2-[2-(dimethylamino)ethyl]-7,10-dihydroxyanthra[1,9-cd]pyrazol-6(2H)-one;

5-[(3-aminopropyl)amino]-2-[2-(dimethylamino)ethyl]-7,10-dihydroxyanthra[1,9-cd]pyrazol-6(2H)-one;

5-[(2-aminoethyl)amino]-7,10-dihydroxy-2-(2-hydroxyethyl)anthra[1,9-cd]pyrazol-6(2H)-one;

5-[[2-(dimethylamino)ethyl]amino]-7,10-dihydroxy-2-(2-hydroxyethyl)anthra[1,9-cd]pyrazol-6(2H)-one;

2-[3-(diethylamino)-2-hydroxypropyl]-7,10-dihydroxy-5-[[2-[(2-hydroxyethyl)amino]ethyl]amino]anthra[1,9-cd]-pyrazol-6(2H)-one;

5-[(2-aminoethyl)amino]-2-[3-(diethylamino)-2-hydroxypropyl]-7,10-dihydroxyanthra[1,9-cd]pyrazol-6(2H)-one;

2-[3-(dimethylamino)propyl]-7,10-dihydroxy-5-[[2-[(2-hydroxyethyl)amino]ethyl]amino]anthra[1,9-cd]pyrazol-6(2H)-one;

7,10-dihydroxy-5-[[2-[(2-hydroxyethyl)amino]ethyl]amino]-2-[2-[(2-hydroxyethyl)methylamino]ethyl]anthra[1,9-cd]pyrazol-6(2H)-one;

7,10-dihydroxy-5-[[2-[(2-hydroxyethyl)amino]ethyl]amino]-2-[3-[(2-hydroxyethyl)amino]propyl]anthra[1,9-cd]pyrazol-6(2H)-one;

5-[(2-aminoethyl)amino]-7,10-dihydroxy-2-[2-[(2-hydroxyethyl)amino]ethyl]anthra[1,9-cd]pyrazol-(2H)-one;

5-[[2-(dimethylamino)ethyl]amino]-7,10-dihydroxy-2-[2-[(2-hydroxyethyl)amino]ethyl]anthra[1,9-cd]pyrazol-6(2H)-one;

5-[[2-(diethylamino)ethyl]amino]-7,10-dihydroxy-2-[2-[(2-hydroxyethyl)amino]ethyl]anthra[1,9-cd]pyrazol-6(2H)-one;

5-[(3-aminopropyl)amino]-7,10-dihydroxy-2-[2-[(2-hydroxyethyl)amino]ethyl]anthra[1,9-cd]pyrazol-6(2H)-one;

7,10-dihydroxy-2-[2-[(2-hydroxyethyl)amino]ethyl]-5-[[3-[(2-hydroxyethyl)amino]propyl]amino]anthra[1,9-cd]pyrazol-6(2H)-one;

5-[[2-[[2-(dimethylaminoethyl]amino]ethyl]amino]-7,10-dihydroxy-2-[2-[(2-hydroxyethyl)amino]ethyl]anthra[1,9-cd]pyrazol-6(2H)-one;

5-[[2-[(2-aminoethyl)amino]ethyl]amino]-7,10-dihydroxy-2-[2-[(2-hydroxyethyl)amino]ethyl]anthra[1,9-cd]-pyrazol-6(2H)-one;

5-[[2-[bis(2-hydroxyethyl)amino]ethyl]amino]-7,10-dihydroxy-2-[2-[(2-hydroxyethyl)amino]ethyl]anthra[1,9-cd]pyrazol-6(2H)-one;

7,10-dihydroxy-2-[2-[(2-hydroxyethyl)amino]ethyl]-5-[[2-(methylamino)ethyl]amino]anthra[1,9-cd]pyrazol-6(2H)-one;

2-(2-aminoethyl)-7,10-dihydroxy-5-[[2-[(2-hydroxyethyl)amino]ethyl]amino]anthra[1,9-cd]pyrazol-6(2H)-one;

2-(2-aminoethyl)-5-[(2-aminoethyl)amino]-7,10-dihydroxyanthra[1,9-cd]pyrazol-6(2H)-one;

2-[2-aminoethyl]-5-[[2-[[2-(dimethylamino)ethyl]amino]ethyl]amino]-7,10-dihydroxyanthra[1,9-cd]pyrazol-6(2H)-one;

2-(2-aminoethyl)-5-[[3-[(2-hydroxyethyl)amino]propyl]amino]-7,10-dihydroxyanthra[1,9-cd]pyrazol-6(2H)-one;

2-(2,3-dihydroxypropyl)-7,10-dihydroxy-5-[[2-[(2-hydroxyethyl)amino]ethyl]amino]anthra[1,9-cd]pyrazol-6(2H)-one;

7-hydroxy-2-[2-[(2-hydroxyethyl)amino]ethyl]-5-[[2-[(2-hydroxyethyl)amino]ethyl]amino]anthra[1,9-cd]pyrazol-6(2H)-one;

7-hydroxy-2-[2-[(2-hydroxyethyl)amino]ethyl]-5-[[2-(methylamino)ethyl]amino]anthra[1,9-cd]pyrazol-6(2H)-one;

10-Hydroxy-2-[2-[(2-hydroxyethyl)amino]ethyl]-5-[[2-[(2-hydroxyethyl)amino]ethyl]amino]anthra[1,9-cd]pyrazol-6(2H)-one;

7,8,10-trihydroxy-2-[2-[(2-hydroxethyl)amino]ethyl]-5-[[2-[(2-hydroxyethyl)amino]ethyl]amino]anthra1,9-cd]pyrazol-6(2H)-one;

7,8,10-trihydroxy-2-[2-[(2-hydroxyethyl)amino)]ethyl]-5-[[2-(methylamino)ethyl]amino]anthra[1,9-cd]pyrazol-6(2H)-one;

5-[[2-[(2-aminoethyl)amino]ethyl]amino]-7,10-dihydroxy-2-(2-hydroxyethyl)anthra[1,9-cd]pyrazol-6(2H)-one;

2-(3-aminopropyl)-7,10-dihydroxy-5-[[2-[(2-hydroxyethyl)amino]ethyl]amino anthra[1,9-cd]pyrazol-6(2H)-one;

2-(3-aminopropyl)-5-[[2-[[2-(dimethylamino)ethyl]amino]ethyl]amino]-7,10-dihydroxy anthra[1,9-cd]pyrazol-6(2H)-one;

2-(2-aminoethyl)-7,10-dihydroxy-5-[[2-(methylamino)ethyl]amino]anthra[1,9-cd]pyrazol-6(2H)-one;

5-[(2-aminoethyl)amino]-2-[3-(dimethylamino)propyl]-7,10-dihydroxyanthra[1,9-cd]pyrazol-6(2H)-one;

7,8-dihydroxy-2-[2-[(2-hydroxyethyl)amino]ethyl]-5-[[2-[(2-hydroxyethyl)amino]ethyl]amino]anthra[1,9-cd]pyrazol-6(2H)-one; and the pharmaceutically acceptable salts thereof.

The invention in its fifth generic chemical compound aspect is a chemical compound having the structural formula

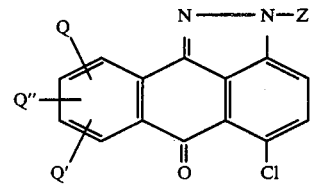

wherein Q, Q', and Q" may be the same or different and are hydrogen, OH, alkoxy of one to four carbon atoms, chlorine, benzyloxy, p-chlorobenzyloxy and p-methoxybenzyloxy; and the pharmaceutically acceptable salts thereof; Z is defined above; and the pharmaceutically acceptable salts thereof; provided that when Q=Q'=Q"=H, Z may not be H or CH₃.

The invention in its sixth generic chemical compound aspect is a chemical compound having the structural formula III

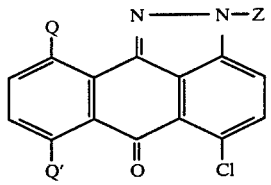

wherein Q and Q' may be the same different and are H, OH, benzyloxy, p-chlorobenzyloxy, or p-methoxybenzyloxy and Z is defined above; and the pharmaceutically acceptable salts thereof; provided that when Q=Q'=H, Z may not be H or $CH_3$.

The invention in a first subgeneric aspect of its sixth chemical compound aspect is a chemical compound having structural formula III wherein Q and Q' are H; and the pharmaceutically acceptable salts thereof.

The invention in a second subgeneric aspect of its sixth chemical compound aspect is a chemical compound having the structural formula III wherein Q and Q' are benzyloxy, p-chlorobenzyloxy, or p-methoxybenzyloxy; and the pharmaceutically acceptable salts thereof.

The invention in a third subgeneric aspect of its sixth chemical compound aspect is a chemical compound having structural formula III wherein Q and Q' are OH; and the pharmaceutically acceptable salts thereof.

The invention as species of the fifth generic chemical compound aspect of the invention are the chemical compounds having the following names:

5-chloro-2-[2-(diethylamino)ethyl]anthra[1,9-cd]pyrazol-6(2H)-one;

5-chloro-2-[2-[(2-hydroxyethyl)amino]ethyl]anthra[1,9-cd]pyrazol-6(2H)-one;

5-chloro-2-[2-(diethylamino)ethyl]-7,10-dihydroxyanthra[1,9-cd]pyrazol-6(2H)-one;

5-chloro-7,10-dihydroxy-2-(2-hydroxyethyl)anthra[1,9-cd]pyrazol-6(2H)-one;

5-chloro-2-[2-(diethylamino)ethyl]-7,10-bis(phenylmethoxy)anthra[1,9-cd]pyrazol-6(2H)-one;

5-chloro-2-[2-[[(4-methylphenyl)sulfonyl]oxy]ethyl]-7,10-bis(phenylmethoxy)anthra[1,9-cd]pyrazol-6(2H)one;

5-chloro-7,10-dihydroxy-2-[2-[(2-hydroxyethyl)amino]ethyl]anthra[1,9-cd]pyrazol-6(2H)-one;

5-chloro-2-[2-[(2-hydroxyethyl)amino]ethyl]-7,10-bis(phenylmethoxy)anthra[1,9-cd]pyrazol-6(2H)-one;

5-chloro-2-[2-[[2-(dimethylamino)ethyl]amino]ethyl]-7,10-dihydroxyanthra[1,9-cd]pyrazol-6(2H)-one;

2-(2-aminoethyl)-5-chloroanthra[1,9-cd]pyrazol-6-(2H)-one;

5-chloro-2-[2-(dimethylamino)ethyl]-7,10-dihydroxyanthra[1,9-cd]pyrazol-6(2H)-one;

5-chloro-2-[3-(diethylamino)-2-hydroxypropyl]-7,10-dihydroxyanthra[1,9-cd]pyrazol-6(2H)-one;

5-chloro-2-[3-(dimethylamino)propyl]-7,10-dihydroxyanthra[1,9-cd]pyrazol-6(2H)-one;

5-chloro-2-(2-hydroxyethyl)-7,10-bis(phenylmethoxy)anthra[1,9-cd]pyrazol-6(2H)-one;

5-chloro-7,10-dihydroxy-2-[2-[(2-hydroxyethyl)methylamino]ethyl]anthra[1,9-cd]pyrazol-6(2H)-one;

5-chloro-2-[2-[(2-hydroxyethyl)methylamino]ethyl]7,10-bis(phenylmethoxy)anthra[1,9-cd]pyrazol-6(2H)-one;

5-chloro-7,10-dihydroxy-2-[3-[(2-hydroxyethyl)amino]propyl]anthra[1,9-cd]pyrazol-6(2H)-one;

5-chloro-2-[3-[(2-hydroxyethyl)amino]propyl]7,10-bis(phenylmethoxy)anthra[1,9-cd]pyrazol-6(2H)-one;

5-chloro-2-[3-[[(4-methylphenyl)sulfonyl]oxy]propyl]-7,10-bis(phenylmethoxy)anthra[1,9-cd]pyrazol-6(2H)-one;

5-chloro-2-(3-hydroxypropyl)-7,10-bis(phenylmethoxy)anthra[1,9-cd]pyrazol-6(2H)-one;

2-(2-aminoethyl)-5-chloro-7,10-dihydroxyanthra-[1,9-cd]pyrazol-6(2H)-one;

2-(2-aminoethyl)-5-chloro-7,10-bis(phenylmethoxy)anthra[1,9-cd]pyrazol-6(2H)-one;

5-chloro-2-[(2,2-dimethyl-1,3-dioxolan-4-yl)methyl]-7,10-bis(phenylmethoxy)anthra[1,9-cd]pyrazol-6(2H)-one;

5-chloro-2-[2-[(2-hydroxyethyl)amino]ethyl]-7-(phenylmethoxy)anthra[1,9-cd]pyrazol-6(2H)-one;

5-chloro-2-[2-[(2-hydroxyethyl)amino]ethyl]-10-(phenylmethoxy)anthra[1,9-cd]pyrazol-6(2H)-one;

5-chloro-2-[2-[(2-hydroxyethyl)amino]ethyl]-7,8,10-tris(phenylmethoxy)anthra[1,9-cd]pyrazol-6(2H)-one;

2-(3-aminopropyl)-5-chloro-7,10-bis(phenylmethoxy)anthra[1,9-cd]pyrazol-6(2H)-one;

5-chloro-2-[2-[(2-hydroxyethyl)amino]ethyl]-7,8-bis(phenylmethoxy)anthra[1,9-cd]pyrazol-6(2H)-one;

5-chloro-2-[2-[[2-(dimethylamino)ethyl]amino]ethyl]-7,10-bis(phenylmethoxy)anthra[1,9-cd]pyrazol-6(2H)-one; and the pharmaceutically acceptable salts thereof.

The invention in its seventh generic chemical compound aspect is a compound having the structural formula IV

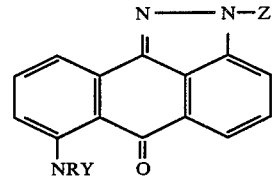

wherein R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is alkylene of from two to eight carbon atoms, $R_2$ and $R_3$ may be the same or different and are H, alkyl of from one to six carbon atoms which may be substituted with OH or an $NR_aR_a$ wherein $R_a$ may be the same or different and is H or alkyl of from one to three carbon atoms which may be substituted with OH, or $R_2$ and $R_3$ when taken together may be ethylene or may form

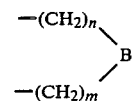

wherein n and m may be the same or different and are one, two, or three, provided that the sum of n and m is an integer of from three to six, and B is a direct bond, O, S, or $N-R_4$ wherein $R_4$ is H or alkyl of from one to six carbon atoms; R and Y when taken together may be ethylene or may form

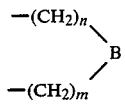

wherein n, m, and B are defined above; Z is H, alkyl of from one to six carbon atoms which may be substituted with an $N(R_1)_2$, $SR_1$, or $OR_1$ group wherein $R_1$ may be the same or different and is defined above, or $DNR_2R_3$ wherein D is alkylene of from two to eight carbon atoms which may be substituted with an OH group and $R_2$ and $R_3$ are as defined above; and the pharmaceutically acceptable salts thereof; with the following provisos, (1) when Z is H, R and Y when taken together do not complete a piperidine ring, (2) when Z is $CH_3$, R and Y when taken together do not complete a piperidine ring or a morpholine ring.

The invention as species of the seventh generic chemical compound aspect of the invention are the chemical compounds having the following names:

2-[2-(diethylamino)ethyl]-7-[[2-[(2-hydroxyethyl)amino]ethyl]amino]anthra[1,9-cd]pyrazol-6(2H)-one;

2-[2-(diethylamino)ethyl]-7-[[2-(diethylamino)ethyl]amino]anthra[1,9-cd]pyrazol-6(2H)-one;

2-[2-[(2-hydroxyethyl)amino]ethyl]-7-[[2-[(2-hydroxyethyl)amino]ethyl]amino]anthra[1,9-cd]pyrazol-6-(2H)-one; and the pharmaceutically acceptable salts thereof.

The invention in its eighth generic chemical compound aspect is a compound having the structural formula VII

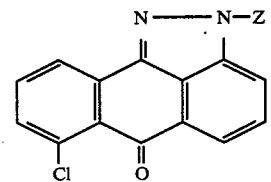

wherein Z is defined above, provided it is not H or $CH_3$.

The invention as a species of the eighth generic chemical compound aspect of the invention is the chemical compound having the following names:

7-chloro-2-[2-(diethylamino)ethyl]anthra[1,9-cd]pyrazol-6(2H)-one;

7-chloro-2-[2-[(2-hydroxyethyl)amino]ethyl]anthra[1,9-cd]pyrazol-6(2H)-one; and the pharmaceutically acceptable salts thereof.

The invention in its ninth chemical compound aspect is 5,8-dichloro-1,4,9,10-anthracenetetrone.

The invention in its tenth chemical compound aspect is the compound 2-[(hydrazinoethyl)amino] ethanol and the acid addition salts thereof.

The invention in its first generic chemical process aspect is a process for preparing a compound having the structural formula

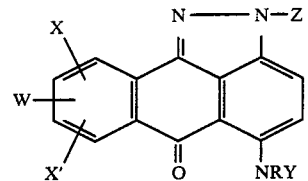

which comprises reacting a compound having the structural formula

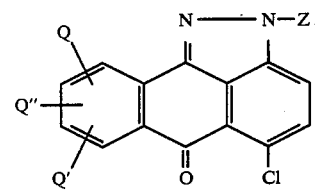

with an amine having the formula HNRY wherein W, X, X', Q, Q', Q'', Y, Z, and R are defined above and, when necessary, removing by catalytic hydrogenation or by treatment with boron tribromide or trichloride any benzyl groups.

The invention in its second generic chemical process aspect is a process for preparing a compound having structural formula I

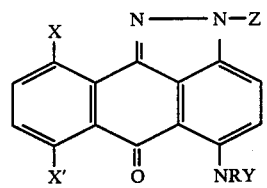

which comprises reacting a compound having structural formula II

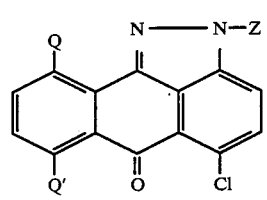

with an amine having the formula HNRY wherein X, X', Q, Q', Y, Z, and R are defined above and, when necessary, removing by catalytic hydrogenation or by treatment with boron tribromide or boron trichloride any benzyl groups.

The invention in a first subgeneric aspect of its second chemical process aspect is the process defined above wherein X and X' are OH.

The invention in a second subgeneric aspect of its second chemical process aspect is the process defined above wherein X and X' are H.

The invention in its third generic chemical process aspect is a process for preparing a compound having structural formula III

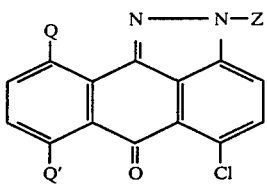

which comprises reacting a compound having formula V

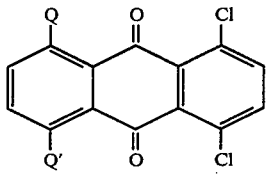

with a hydrazine having the formula H₂N-NHZ, wherein Q, Q' and Z are defined above.

The invention in a first subgeneric aspect of its third chemical process aspect is the process defined above wherein Q and Q' are benzyloxy, p-chlorobenzyloxy, or p-methoxybenzyloxy.

The invention in a second subgeneric aspect of its third chemical process aspect is the process defined above wherein Q and Q' are OH.

The invention in a third subgeneric aspect of its third chemical process aspect is the process defined above wherein Q and Q' are H.

The invention in its fourth generic chemical process aspect is a process for preparing a compound having structural formula IV

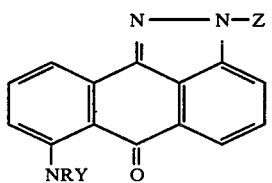

which comprises reacting a compound having structural formula VII

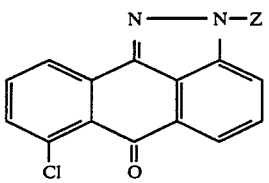

with an amine having the formula HNRY, wherein Y, Z, and R are defined above.

The invention in its fifth chemical process aspect is a process for preparing 5,8-dichloro-1,4,9,10-anthracenetetrone which comprises reacting 1,4-dichloro-5,8-dihydroxy-9,10-anthracenedione with lead tetracetate.

The invention in its sixth chemical process aspect is a process for preparing 2-[(hydrazinoethyl)amino]ethanol which comprises reacting hydrazine with N-(2-hydroxyethyl)aziridine.

The invention in its first pharmaceutical composition aspect is a pharmaceutical composition comprising a compound having structural formula I and the pharmaceutically acceptable salts thereof in combination with a pharmaceutically acceptable carrier.

The invention in its second pharmaceutical composition aspect is a pharmaceutical composition comprising a compound having structural formula I' and the pharmaceutically acceptable salts thereof in combination with a pharmaceutically acceptable carrier.

The invention in its third pharmaceutical composition aspect is a pharmaceutical composition comprising a compound having structural formula I'' and the pharmaceutically acceptable salts thereof in combination with a pharmaceutically acceptable carrier.

The invention in its fourth pharmaceutical composition aspect is a pharmaceutical composition comprising a compound having structural formula I''' and the pharmaceutically acceptable salts thereof in combination with a pharmaceutically acceptable carrier.

The invention in its fifth pharmaceutical composition aspect is a pharmaceutical composition comprising a compound having structural formula I'''' and the pharmaceutically acceptable salts thereof in combination with a pharmaceutically acceptable carrier.

The invention in its sixth pharmaceutical composition aspect is a pharmaceutical composition comprising a compound having structural formula $I^v$ and the pharmaceutically acceptable salts thereof in combination with a pharmaceutically acceptable carrier.

The invention in its seventh pharmaceutical composition aspect is a pharmaceutical composition comprising a compound having structural formula $I^{vi}$ and the pharmaceutically acceptable salts thereof in combination with a pharmaceutically acceptable carrier.

The invention in its eighth pharmaceutical composition aspect is a pharmaceutical composition comprising a compound having structural formula IV and the pharmaceutically acceptable salts thereof in combination with a pharmaceutically acceptable carrier.

The invention in its first pharmaceutical method aspect is a method for treating microbial infections in a mammal which comprises administering a sufficient amount of a compound having structural formula I and the pharmaceutically acceptable salts thereof in combination with a pharmaceutically acceptable carrier to a mammal in need thereof.

The invention in its second pharmaceutical method aspect is a method for treating leukemia in a mammal which comprises administering a sufficient amount of a compound having structural formula I' and the pharmaceutically acceptable salts thereof in combination with a pharmaceutically acceptable carrier, to a mammal in need thereof.

The invention in its third pharmaceutical method aspect is a method for treating leukemia in a mammal which comprises administering a sufficient amount of a compound having structural formula I'' and the pharmaceutically acceptable salts thereof in combination with a pharmaceutically acceptable carrier, to a mammal in need thereof.

The invention in its fourth pharmaceutical method aspect is a method for treating solid tumors in a mammal which comprises administering a sufficient amount of a compound having structural formula I''' and the pharmaceutically acceptable salts thereof in combination with a pharmaceutically acceptable carrier, to a mammal in need thereof.

The invention in its fifth pharmaceutical method aspect is a method for treating solid tumors in a mammal which comprises administering a sufficient amount of a compound having structural formula I'''' and the pharmaceutically acceptable salts thereof in combination with a pharmaceutically acceptable carrier, to a mammal in need thereof.

The invention in its sixth pharmaceutical method aspect is a method for treating solid tumors in a mammal which comprises administering a sufficient amount of a compound having structural formula I$^v$ and the pharmaceutically acceptable salts thereof in combination with a pharmaceutically acceptable carrier, to a mammal in need thereof.

The invention in its seventh pharmaceutical method aspect is a method for treating solid tumors in a mammal which comprises administering a sufficient amount of a compound having structural formula I$^{vi}$ and the pharmaceutically acceptable salts thereof in combination with a pharmaceutically acceptable carrier, to a mammal in need thereof.

The invention in its eighth pharmaceutical method aspect is a method for treating solid tumors in a mammal which comprises administering a sufficient amount of a compound having structural formula IV and the pharmaceutically acceptable salts thereof in combination with a pharmaceutically acceptable carrier, to a mammal in need thereof.

DESCRIPTION OF THE PREFERRED EMBODIMENTS

The compounds of the invention may be prepared conveniently by the following reaction sequence

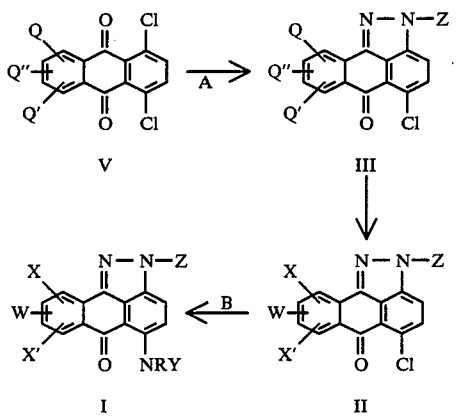

The reaction step "A," involves the reaction of compound V and a suitably substituted hydrazine, NH$_2$-NHZ wherein Q, Q' and Q", and Z are defined hereinabove. This reaction may be accomplished in any of a variety of reaction inert solvents by mixing approximately equimolar amounts of compound V and the desired hydrazine in the chosen solvent at elevated temperature. Use of a catalyst such as potassium fluoride or of a slight molar excess of the hydrazine reactant may improve a particular yield. Examples of suitable solvents are N,N-dimethylformamide, dimethylsulfoxide, pyridine, acetonitrile, the cellosolves, and the like. Pyridine is the preferred solvent, suitable reaction temperatures are from about 30°–85° C. In general, the reaction is allowed to proceed for about six to about 24 hours at which time the reaction is substantially complete. The completeness of a particular reaction may be measured by known procedures such as thin layer chromatography for example. It is generally observed that increasing the reaction temperature will decrease the time necessary for completing the reaction. The proper choice of the reaction variables is within the skill of the art. The products of the reaction are isolated and purified by standard procedures. For example, the reaction mixture may be concentrated by evaporating the solvent and the residue may be partitioned between water and a convenient nonwater-miscible organic solvent such as chloroform, benzene, dichloromethane, and the like. The solvent may then be evaporated and the residue may be chromatographed, for example, on silica gel. Choice of the proper chromatography solvent is within the skill of the art. After chromatography, the product may be recrystallized, if desired. When the Q, Q', and Q" substituents of the so produced compound III comprise benzyloxy, p-chlorobenzyloxy, or p-methoxybenzyloxy, the benzyl substituents may be removed, for example, by treatment with boron trichloride or boron tribromide in a chlorinated hydrocarbon solvent such as dichloromethane at about 0° C. to produce compound II wherein the corresponding X substituents represent hydroxyl. Acid addition salts may also be prepared by standard procedures. For example, a hydrochloride salt may be prepared by dissolving the free base in a convenient solvent such as 2-propanol and treating this solution with a solution of hydrogen chloride in 2-propanol. The acid addition salts may be reconverted to the respective free base by treatment with a dilute solution of sodium hydroxide or potassium carbonate for example.

The reaction step "B" involves the reaction of compound II with a suitably substituted amine HNRY wherein R, W, X, X', Y, and Z are defined hereinabove. This reaction may be accomplished in any of a variety of reaction inert solvents by mixing approximately equimolar amounts of compound II and the desired amine in the chosen solvent at elevated temperature. The use of a slight molar excess of the amine reactant, an inert atmosphere and a catalyst such as anhydrous cuprous chloride may improve a particular yield. The use of these variations for a particular reaction is optional and is within the skill of the art. Examples of suitable solvents are N,N'-dimethylformamide, dimethylsulfoxide, pyridine, acetonitrile, the cellosolves, and the like. Suitable reaction temperatures are from about 85°–130° C. This reaction has been observed to proceed particularly efficiently in refluxing pyridine. In general, the reaction is allowed to proceed for about 6 to about 24 hours at which time it is substantially complete. The completeness of a particular reaction may be measured by known procedures such as thin layer chromatography for example. It is generally observed that increasing the reaction temperature will decrease the time necessary for completing the reaction. The proper choice of the reaction variables is within the skill of the art. The products of the reaction are isolated and purified by standard procedures which are substantially identical to those described above for compound II. Likewise, acid addition salts of compound I may be prepared by standard procedures such as that described hereinabove for compound II.

Alternatively, the compound of formula III may be treated directly with an amine of formula HNRY to produce a compound of the formula

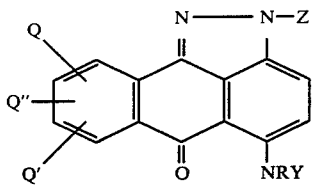

This compound may then be debenzylated by a standard procedure to produce the corresponding compound having structural formula I.

In an alternate process the compounds of formula I wherein X and X' are hydroxy may be prepared by the reaction of compound VI (compound V wherein Q and Q' are dihydroxy

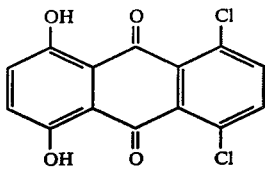

with a suitably substituted hydrazine NH$_2$-NHZ to produce a compound of structural formula II wherein X is OH; Z is defined hereinabove. The reaction of VI and the hydrazine may be accomplished by mixing approximately equimolar amounts of the reactants in a solvent such as N,N-dimethylformamide, dimethylsulfoxide, pyridine, and the like at temperatures about 30°–90° C., preferably 30°–60° C., in the presence of a base such as potassium bicarbonate. Pyridine is the preferred solvent and when utilized does not require an additional base. The use of catalyst such as potassium fluoride may improve the yield of a particular reaction. The subsequent conversion of the so produced compound II wherein X and X' are hydroxy to the corresponding compound I is carried out as already described hereinabove as reaction step "B".

In an alternate method for preparing the compounds of formula III, a compound of formula V is reacted with a hydroxyalkylhydrazine of the formula NH$_2$—NH(CH$_2$)$_{2-11}$—OH, preferably NH$_2$—NH(CH$_2$)$_{2-3}$—OH to produce a compound of formula III wherein Z is —(CH$_2$)$_{2-11}$—OH and is preferably —(CH$_2$)$_{2-3}$—OH. This reaction is carried out substantially as described hereinabove as reaction step "A". The OH group of the Z substituent is then derivatized to produce an easily displaceable substituent known to those skilled in the art as a "leaving group". For example, the OH group may be converted to a tosyloxy or mesyloxy group by reaction with respectively p-toluenesulphonylchloride or methanesulphonylchloride in pyridine by procedures known to those skilled in the art. The leaving group, so produced, may be subsequently displaced with, for example, an amine such as diethylamine to produce a Z substituent of the structure —(CH$_2$)$_{2-11}$—NEt$_2$. In the preferred procedure the substituent Z so produced is —(CH$_2$)$_{2-3}$NEt$_2$. The benzyl groups or substituted benzyl groups of compound III, if present, are removed as described above to produce a compound of formula II, which may be converted to a compound of formula I as already described hereinabove as reaction step "B".

The compounds having structural formula I wherein X and X' are chloro are prepared starting from compound VI by first converting VI to the corresponding di-p-toluenesulfonic acid ester VI'.

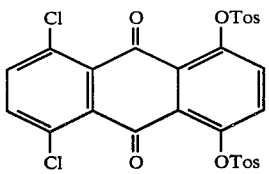

This conversion is conveniently carried out by treating VI with p-toluenesulfonyl chloride in a nonreactive solvent such as acetonitrile at reflux temperature. The diester VI' is then treated with a substituted hydrazine NH$_2$NHZ substantially as described above for the conversion of compound V to compound III. The product of this reaction, VI"

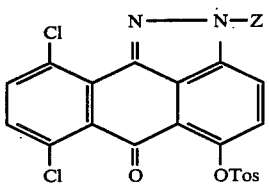

is then treated with an amine having the formula HNYR substantially as described above for the conversion of compound II to compound I. The product of this reaction has the following structural formula

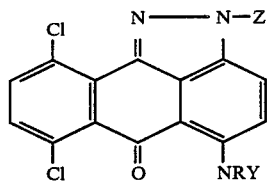

wherein R, Y, and Z are as defined hereinabove.

The compounds having structural formula IV are prepared by reacting a compound having structural formula VII with an amine having the formula HNRY using substantially the same reaction conditions described above for the conversion of compound II to compound I, i.e., reaction step "B". A particular Z substituent, for example, CH$_2$CH$_2$OH may also be derivatized and converted to another particular Z substituent, for example CH$_2$CH$_2$NEt$_2$ in a similar manner to the procedure already described hereinabove.

The compounds of structural formula VII are prepared by reacting a suitably substituted hydrazine, NH$_2$-NHZ, wherein Z is defined hereinabove, with 1,5-dichloro-9,10-anthracenedione in a manner substantially identical to that described above for converting compound V to compound III, i.e., reaction sequence "A".

The present invention also contemplates the novel hydrazine, 2-[(hydrazinoethyl)amino]ethanol, NH$_2$NHCH$_2$CH$_2$NHCH$_2$CH$_2$OH. This novel hydrazine is a useful intermediate for the preparation of a variety of final compounds of the invention. This novel hydrazine may be prepared by a variety of procedures which are considered equivalent for purposes of the invention. One such procedure involves the reaction of hydrazine and N-(2-hydroxyethyl)aziridine in an aqueous medium at reflux temperature. The novel 2-[(hydrazinoethyl)amino]ethanol so produced is isolated by standard procedures as a clear liquid which has bp 120° C. at 0.035 mmHg. The novel 2-[(hydrazinoethyl)amino]ethanol forms acid addition salts with organic and inorganic acids such as hydrochloric, hydrobromic, sulfonic, phosphonic, methanlsulfonic, acetic, benzoic, and the like. For purposes of the invention, such salts are considered equivalent to the free base form of the novel hydrazine.

The benzylated ethers V wherein any of the Q substituents represent benzyloxy, p-chlorobenzyloxy, or p-methoxybenzyloxy may be prepared by treating compound V wherein any of the Q substituents represent OH with the corresponding benzyl bromide or benzyl chloride in a convenient nonreactive solvent such as acetone, dimethylsulfoxide, N,N-dimethylformamide, and the like. The use of a hydrogen halide acceptor such as an alkali metal carbonate (e.g., potassium carbonate) for this reaction is preferred.

The novel intermediate, 5,8-dichloro-1,4,9,10-anthracenetetrone may be prepared by oxidation of 1,4-dichloro-5,8-dihydroxy-9,10-anthracenedione. The reaction may be carried out with lead tetraacetate in glacial acetic acid at or near room temperature.

The 1,4-dichloro-9,10-anthracenedione, compound V wherein Q=Q'=Q"=hydrogen, may be prepared by known methods, see for example J. Am. Chem. Soc., 48; 3198 (1926).

The 1,4-dichloro-5,8-dihydroxy-9,10-anthracenedione, compound VI, may be prepared by known methods, see for example U.S. Pat. No. 3,631,074.

The compound 1,5-dichloro-9,10-anthracenedione, which is utilized to prepare the compounds of formula VII is commercially available or may be prepared by methods known to those skilled in the art, see for example Beilstein 7, 787.

The compounds of the invention form pharmaceutically acceptable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include fluorine, chlorine, bromine, and iodine.

The alkyl and alkoxy groups contemplated by the invention, unless specified otherwise, comprise both straight and branched carbon chains of from one to about six carbon atoms. Representative of such groups are methyl, ethyl, isopropyl, butyl, pentyl, 3-methylpentyl, methoxy, ethoxy, i-propoxy, t-butoxy, n-hexoxy, 3-methylpentoxy, and the like.

The alkylene groups contemplated by the invention, unless specified otherwise, comprise both straight and branched carbon chains of from two to about 11 carbon atoms. Representative of such groups are ethylene, n-propylene, n-butylene, n-heptalene, i-propylene, 3-ethyl-1,5-pentalene, 3-propyl-1,6-hexalene, and the like. The preferred alkylene groups of the invention have the following structural formulas:

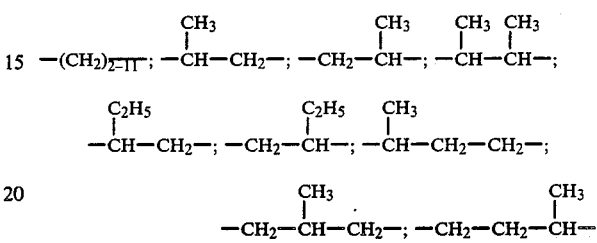

Certain substituents, such as alkyl or alkylene substituents contemplated by the invention are defined as possibly being substituted with additional substituents, e.g., $NH_2$. Those skilled in the art will recognize that certain combinations of such substituents are most probably unstable and these are not intended to be included within the scope of the definitions. For example, an α-aminoalkyl or alkylene group of the general formula =N—CH—$NH_2$ would not be expected to be stable whereas the corresponding dialkylated substituent =N—CH—N(Alk)$_2$ is expected to be stable and is intended to be included within the definitions. It is within the skill of the art to recognize these and other such substituents which are possibly unstable.

The compounds of the invention are new chemical substances of value as pharmacological agents for the treatment of bacterial and fungal infections in warm-blooded animals. They may also be utilized as antiseptic agents such as for use in the sterilization of laboratory glassware etc. The antibacterial and antifungal activity of representative compounds of the invention was established by the screening procedure described below.

1. Preparation of inocula (A) Bacteria and yeast:

The bacterial and yeast isolates are maintained in agar slants or in liquid media, hereby designated as inoculum media. The cultures are transferred at regular intervals in such media. (See Table for the corresponding inoculum media of each culture.) The organisms are generally transferred on to agar slants or liquid inoculum media and incubated overnight (18–20 hours): 37° C. for the bacterial isolates and 28° C. for the fungal cultures.

The microbial cells from the overnight agar slants are then scraped off and suspended in saline solution (0.85% NaCl). The microbial concentrations are adjusted to a light transmittancy of 20–35%, Junior Coleman Spectrophotometer (555 M ). For the organisms that are maintained in liquid media, an aliquot of the culture suspension is simply diluted with saline to 20–35% light transmittancy.

The above microbial suspension serve as inocula for the assay plates. Thus, 0.16–10 ml (see Table for exact amount) are used to inoculate 100 ml of the molten-agar assay medium.

(B) Mycelial fungi:

The *Penicillium avellaneum* is grown for six days, at 28° C., on an agar medium. This is to allow sporulation of the culture. The organism is then harvested by scraping off the cells from the agar surface (mycelia and spores) and suspending them in saline solution containing 0.05% Tween 80.

The suspension is adjusted to a light transmitancy of 20%. One ml of this suspension is used to inoculate 100 ml of the molten-agar assay medium.

2. Preparation of assay plates

Stainless steel frames, 12.3×25.3 cm (ID) and glass plates, 15.3×31.7 cm are used to make the test trays. The frames are attached to the plates with tape at each end and the inner edges sealed with 2% agar. Twenty five ml of inoculated assay medium is spread evenly on each tray and allowed to solidify. The trays are covered, inverted, and refrigerated until used.

3. Disking of samples

The compounds or samples to be tested are dissolved in suitable solvents, e.g., alcohols, dimethylsulfoxide, or N,N-dimethylformamide. The samples are generally dissolved so that the final concentration of the solvent is <10%.* The compounds are tested at different concentrations: 3,000; 1,000; 500; 100; and 10 mcg/ml. Paper discs (12.7 mm diameter) are placed on the agar trays with forceps, then 0.08 ml of the dissolved compound is pipetted onto each disc using a 0.2 ml pipette.

(*If the compound does not stay in solution at <10% alcohol, then the full strength alcohol is used. However, the impregnated discs are air-dried before they are laid on to the seeded agar plates.)

4. Interpretation of results

The disked agar trays are incubated overnight (18-20 hours) at 37° C. for the bacterial cultures and 28° C. for the yeasts. The *Penicillium avellaneium* tray is incubated for at least 20-24 hours since it is a slower-growing organism. Active compounds show a zone of inhibition around the disc. The diameter of the zone is measured in mm. The zone diameter of active compounds ranges from a minimum of 13.5 mm to as high as 60 mm. The size of the zone diameter generally reflects the activity of the compound: the larger the zone the greater the activity.

TABLE

| Culture | Number | Inoculum Medium | Inoculum Level ml/100 ml | Assay Medium |
|---|---|---|---|---|
| *Aerobacter aerogenes* | 0126 | Veal Infusion Broth | 1 | Mycin Agar |
| *Escherichia coli* | 04863 | AM-08 Agar | 1 | AM-08 |
| *Bacillus subtilis* | 04555 | AM-08 Broth | 0.5 | AM-08 |
| *Streptococcus faecalis* | 05045 | Folic Acid Assay Broth | 2 | AM-09 |
| *Penicillium avellaneum* | M2988 | AM-25 Agar | 1 | AM-25 |

5. Culture media

The composition of the various culture media, except for the commercially available media, are shown below. The commercial ready-made Veal Infusion Medium is obtained from Difco Laboratories, Detroit, Mich., USA. Add 1.5% agar to these media for use as agar plates.

| AM-08 | % |
|---|---|
| Glucose | 0.2 |
| Sodium Glutamate | 1.04 |
| $KH_2PO_4$ | 0.03 |
| $Na_2HPO_4$ | 0.07 |
| Salts #1[a] | 1 ml |
| Salts #2[b] | 10 ml |
| $H_2O$ (distilled) | |

| [a]Salts #1 | % | [b]Salts #2 | % |
|---|---|---|---|
| $MgSO_4$ | 1.0 | $MnSO_4$ | 1.0 |
| $CaCl_2$ | 5.0 | $ZnSO_4 \cdot 7H_2O$ | 1.0 |
| NaCl | 5.0 | $FeSO_4 \cdot 7H_2O$ | 1.0 |
| $CuSO_4 \cdot 5H_2O$ | 0.01 | $H_2O$ (distilled) | |
| $H_2O$ (distilled) | | | |

| AM-09 | |
|---|---|
| $K_2HPO_4$ | 3.9 gm |
| Dextrose | 25 gm |
| Na—citrate · 2 $H_2O$ | 34.4 gm |
| Casein hydrolysate | 6.2 gm |
| Asparagine | 375 mg |
| L—tryptophan | 125 mg |
| Cysteine | 312.5 mg |
| Glutathione | 3.1 mg |
| Thiamine HCl | 250 g |
| Riboflavin | 625 g |
| Ca pantothenate | 500 g |
| Nicotinic acid | 500 g |
| p-aminobenzoic acid | 625 g |
| Biotin | 12.5 g |
| Pyridoxine HCl | 2.5 g |
| Folic Acid | 500 g |
| NaCl | 12.5 g |
| $MgSO_4$ | 250 g |
| $FeSO_4$ | 12.5 g |
| $MnSO_4 \cdot H_2O$ | 125 g |
| Tween 80 | 62.5 mg |
| $H_2O$ (distilled) | 1000 ml |

| AM-25 | |
|---|---|
| $Na_2HPO_4 \cdot H_2O$ | 0.35 |
| $KH_2PO_4$ | 0.05 |
| Yeast Extract (Difco) | 0.5 |
| Dextrose | 1.0 |
| Distilled Water | |

Utilizing the above described procedure, the following results were obtained for representative compounds of the invention.

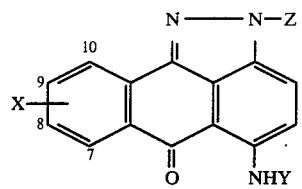

Inhibition Zone Diameter mm (Dose mg/ml)

| X | Y | Z | A. Aerogenes | E. Coli | B. Subtilis | S. Faecalis | P. Avellaneum |
|---|---|---|---|---|---|---|---|
| H | $CH_2CH_2NEt_2$ | $CH_2CH_2NEt_2$ | 19 (0.5) | 15 (1.0) | 15 (0.1) | 14 (0.5) | 19 (3.0) |
| H | $CH_2CH_2NHCH_2CH_2OH$ | $CH_2CH_2NEt_2$ | 18 (0.5) | 14 (0.1) | 16 (0.1) | 15 (0.5) | 0 (3.0) |
| H | $CH_2CH_2NEt_2$ | $CH_3$ | 17 (0.5) | 15 (3.0) | 15 (0.1) | 16 (1.0) | 16 (0.5) |
| H | $CH_2CH_2NHCH_2CH_2OH$ | $CH_2CH_2OH$ | 14 (0.5) | 14 (3.0) | 14 (0.1) | 16 (3.0) | 0 (3.0) |
| H | $CH_2CH_2NEt_2$ | $CH_2CH_2OH$ | 20 (0.5) | 15 (1.0) | 15 (0.1) | 14 (1.0) | 16 (3.0) |
| H | $CH_2CH_2NHCH_2CH_2OH$ | H | 18 (0.5) | 0 (3.0) | 19 (0.5) | 17 (3.0) | 0 (3.0) |
| H | $CH_2CH_2NHCH_2CH_2OH$ | $CH_3$ | 17 (0.5) | 14 (1.0) | 14 (0.1) | 14 (1.0) | 0 (3.0) |
| H | $CH_2CH_2NH_2$ | $CH_2CH_2NEt_2$ | 14 (0.5) | 14 (1.0) | 15 (0.1) | 17 (0.5) | 16 (3.0) |
| H | $CH_2CH_2NHCH_2CH_2OH$ | $CH_2CH_2NHCH_2CH_2OH$ | 14 (1.0) | 16 (3.0) | 18 (0.5) | 0 (3.0) | 0 (3.0) |
| H | $CH_2CH_2NH_2$ | $CH_2CH_2NHCH_2CH_2OH$ | 16 (0.5) | 14 (1.0) | 15 (0.1) | 0 (3.0) | 0 (3.0) |
| H | $CH_2CH_2NEt_2$ | $CH_2CH_2NHCH_2CH_2OH$ | 18 (0.5) | 14 (0.1) | 14 (0.1) | 15 (0.5) | 16 (3.0) |
| H | $CH_2CH_2OH$ | $CH_2CH_2NHCH_2CH_2OH$ | 14 (1.0) | 15 (0.5) | 18 (0.5) | 14 (1.0) | 0 (3.0) |
| H | $CH_2CH_2NMe_2$ | $CH_2CH_2NHCH_2CH_2OH$ | 16 (0.5) | 15 (1.0) | 20 (0.5) | 15 (0.5) | 0 (3.0) |
| H | $CH_3$ | $CH_2CH_2NHCH_2CH_2OH$ | 15 (0.1) | 14 (0.5) | 14 (0.1) | 15 (0.5) | 0 (3.0) |
| H | $CH_2CH_2$–N(morpholino) | $CH_2CH_2OH$ | 0 (3.0) | 16 (3.0) | 16 (1.0) | 0 (3.0) | 0 (3.0) |
| H | $(CH_2)_3NEt_2$ | $CH_2CH_2OH$ | 15 (1.0) | 0 (3.0) | 22 (1.0) | 14 (3.0) | 0 (3.0) |
| H | $CH_2CH_2$–N(morpholino) | $CH_2CH_2NEt_2$ | 15 (1.0) | 14 (1.0) | 25 (1.0) | 14 (0.5) | 14 (1.0) |
| H | $(CH_2)_3NEt_2$ | $CH_2CH_2NEt_2$ | 20 (0.1) | 15 (3.0) | 25 (1.0) | 14 (1.0) | 15 (3.0) |
| H | $(CH_2)_4NEt_2$ | $CH_2CH_2NEt_2$ | 16 (0.1) | 15 (3.0) | 17 (1.0) | 14 (3.0) | 14 (3.0) |
| H | $(CH_2)_7NEt_2$ | $CH_2CH_2NEt_2$ | 0 (3.0) | 14 (1.0) | 17 (0.5) | 14 (3.0) | 14 (1.0) |
| H | $(CH_2)_4NEt_2$ | $CH_2CH_2OH$ | 0 (3.0) | 0 (3.0) | 25 (1.0) | 0 (3.0) | 0 (3.0) |
| H | $(CH_2)_7NEt_2$ | $CH_2CH_2OH$ | 0 (3.0) | 0 (3.0) | 20 (1.0) | 0 (3.0) | 0 (3.0) |
| H | $(CH_2)_5CH_3$ | $CH_2CH_2NEt_2$ | 0 (3.0) | 0 (3.0) | 16 (1.0) | 0 (3.0) | 16 (3.0) |
| H | $CH_2CH_2$–N(piperazino)NH | $CH_2CH_2NEt_2$ | 19 (0.1) | 0 (3.0) | 24 (1.0) | 14 (3.0) | 0 (1.0) |
| H | $CH_2CH_2NHCH_2CH_2OH$ | $CH_2CH_2NH_2$ | 17 (0.1) | 14 (0.5) | 14 (3.0) | 0 (3.0) | 0 (3.0) |
| 7,10-$(OH)_2$ | $CH_2CH_2NHCH_2CH_2OH$ | $CH_2CH_2NEt_2$ | 14 (1.0) | 14 (0.5) | 15 (1.0) | 14 (1.0) | 0 (3.0) |
| 7,10-$(OH)_2$ | $CH_2CH_2NEt_2$ | $CH_2CH_2NEt_2$ | 0 (3.0) | 14 (0.5) | 14 (0.5) | 14 (0.5) | 16 (3.0) |
| 7,10-$(OH)_2$ | $CH_2CH_2NH_2$ | $CH_3$ | 14 (3.0) | 14 (3.0) | 0 (3.0) | 14 (3.0) | 0 (3.0) |
| 7,10-$(OH)_2$ | $CH_2CH_2NHCH_2CH_2OH$ | $CH_2CH_2OH$ | 0 (3.0) | 0 (3.0) | 17 (3.0) | 0 (3.0) | 0 (3.0) |
| 7,10-$(OH)_2$ | $CH_2CH_2NH_2$ | $CH_2CH_2OH$ | 15 (1.0) | 0 (3.0) | 15 (1.0) | 0 (3.0) | 0 (3.0) |
| 7,10-$(OH)_2$ | $CH_2CH_2NH_2$ | $CH_2CH_2NEt_2$ | 16 (0.5) | 15 (1.0) | 16 (1.0) | 0 (3.0) | 14 (3.0) |
| 7,10-$(OH)_2$ | $CH_2CH_2NHMe$ | $CH_2CH_2NEt_2$ | 16 (0.5) | 16 (0.5) | 17 (1.0) | 14 (3.0) | 0 (3.0) |
| 7,10-$(OH)_2$ | $CH_2CH_2NEt_2$ | $CH_2CHOHCH_2NEt_2$ | 14 (3.0) | 16 (0.5) | 15 (3.0) | 14 (3.0) | 0 (3.0) |
| 7,10-$(OH)_2$ | $CH_2CH_2NH_2$ | $CH_2CHOHCH_2NEt_2$ | 15 (0.5) | 15 (0.5) | 14 (3.0) | 0 (3.0) | 0 (3.0) |
| 7,10-$(OH)_2$ | $(CH_2)_3NH(CH_2)_2OH$ | $(CH_2)_2NH(CH_2)_2OH$ | 14 (0.5) | 14 (0.5) | 16 (1.0) | 14 (3.0) | 0 (3.0) |
| 7,10-$(OH)_2$ | $(CH_2)_2NH(CH_2)_2NMe_2$ | $(CH_2)_2NH(CH_2)_2OH$ | 14 (1.0) | 15 (1.0) | 18 (3.0) | 16 (3.0) | 0 (3.0) |
| 7,10-$(OH)_2$ | $(CH_2)_2NH(CH_2)_2OH$ | $(CH_2)_2NMe_2$ | 14 (1.0) | 15 (0.5) | 15 (1.0) | 0 (3.0) | 0 (3.0) |
| 7,10-$(OH)_2$ | $(CH_2)_2NMe_2$ | $(CH_2)_2OH$ | 15 (0.5) | 0 (3.0) | 14 (3.0) | 14 (3.0) | 0 (3.0) |
| 7,10-$(OH)_2$ | $(CH_2)_2NH_2$ | $(CH_2)_2NMe_2$ | 14 (0.5) | 14 (0.5) | 14 (3.0) | 16 (3.0) | 0 (3.0) |
| 7,10-$(OH)_2$ | $(CH_2)_2NH_2$ | $(CH_2)_2NH(CH_2)_2OH$ | 15 (3.0) | 14 (1.0) | 14 (3.0) | 0 (3.0) | 0 (3.0) |
| 7,10-$(OH)_2$ | $(CH_2)_2NH(CH_2)_2OH$ | $(CH_2)_2NH(CH_2)_2OH$ | 15 (3.0) | 14 (1.0) | 14 (3.0) | 0 (3.0) | 0 (3.0) |
| 7,10-$(OH)_2$ | $(CH_2)_2NH(CH_2)_2OH$ | $(CH_2)_2OCH_3$ | 14 (3.0) | 14 (1.0) | 14 (3.0) | 0 (3.0) | 0 (3.0) |
| 7,10-$(OH)_2$ | $(CH_2)_2NMe_2$ | $(CH_2)_2NH(CH_2)_2OH$ | 14 (0.5) | 14 (0.5) | 14 (1.0) | 14 (1.0) | 0 (3.0) |
| 7,10-$(OH)_2$ | $(CH_2)_2NEt_2$ | $(CH_2)_2NH(CH_2)_2OH$ | 14 (0.5) | 14 (0.5) | 15 (0.5) | 14 (1.0) | 14 (3.0) |
| 7,10-$(OH)_2$ | $(CH_2)_2NH_2$ | $(CH_2)_2OMe$ | 14 (3.0) | 16 (3.0) | 16 (3.0) | 0 (3.0) | 0 (3.0) |
| 7,10-$(OH)_2$ | $(CH_2)_3NH_2$ | $(CH_2)_2NH(CH_2)_2OH$ | 14 (3.0) | 15 (3.0) | 0 (3.0) | 0 (3.0) | 0 (3.0) |
| 7,10-$(OH)_2$ | $(CH_2)_4NH_2$ | $(CH_2)_2NH(CH_2)_2OH$ | 16 (3.0) | 15 (3.0) | 14 (3.0) | 0 (3.0) | 0 (3.0) |
| 7,10-$(OH)_2$ | $(CH_2)_5NH_2$ | $(CH_2)_2NH(CH_2)_2OH$ | 0 (3.0) | 14 (3.0) | 0 (3.0) | 0 (3.0) | 0 (3.0) |

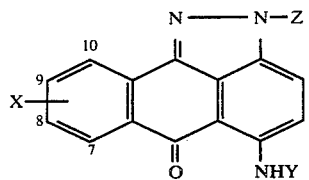

Inhibition Zone Diameter mm (Dose mg/ml)

| X | Y | Z | A. Aerogenes | E. Coli | B. Subtilis | S. Faecalis | P. Avellaneum |
|---|---|---|---|---|---|---|---|
| 7,10-(OH)$_2$ | (CH$_2$)$_2$N⌐O⌐ (morpholino) | (CH$_2$)$_2$NH(CH$_2$)$_2$OH | 0 (3.0) | 14 (3.0) | 15 (1.0) | 0 (3.0) | 0 (3.0) |
| 7,10-(OH)$_2$ | N⌐N—Me* (piperazinyl) | (CH$_2$)$_2$NH(CH$_2$)$_2$OH | 17 (0.5) | 14 (1.0) | 0 (3.0) | 0 (3.0) | 0 (3.0) |
| 7,10-(OH)$_2$ | N(CH$_2$)$_2$NMe$_2$* Me | (CH$_2$)$_2$NH(CH$_2$)$_2$OH | 16 (0.5) | 15 (3.0) | 0 (3.0) | 0 (3.0) | 0 (3.0) |
| 7,10-(OH)$_2$ | (CH$_2$)$_2$NH$_2$ | (CH$_2$)$_2$NH$_2$ | 14 (3.0) | 0 (3.0) | 0 (3.0) | 0 (3.0) | 0 (3.0) |
| 7,10-(OH)$_2$ | (CH$_2$)$_3$NH$_2$ | (CH$_2$)$_2$NMe$_2$ | 14 (3.0) | 15 (3.0) | 0 (3.0) | 0 (3.0) | 0 (3.0) |
| 7,10-(OH)$_2$ | (CH$_2$)$_2$NH(CH$_2$)$_2$OH | (CH$_2$)$_3$NMe$_2$ | 16 (3.0) | 0 (3.0) | 0 (3.0) | 0 (3.0) | 0 (3.0) |
| 7,10-(OH)$_2$ | (CH$_2$)$_3$NH$_2$ | (CH$_2$)$_3$NMe$_2$ | 14 (3.0) | 14 (3.0) | 14 (3.0) | 0 (3.0) | 0 (3.0) |
| 7,10-(OH)$_2$ | (CH$_2$)$_2$NH$_2$ | (CH$_2$)$_3$NMe$_2$ | 15 (3.0) | 15 (3.0) | 0 (3.0) | 0 (3.0) | 0 (3.0) |
| 7,10-(OH)$_2$ | (CH$_2$)$_2$NEt$_2$ | CH$_2$CH$_2$OH | 0 (3.0) | 0 (3.0) | 14 (0.5) | 14 (3.0) | 0 (3.0) |
| 7,10-(OH)$_2$ | CH$_2$CH$_2$NHCH$_2$CH$_2$OH | CH$_2$CHOHCH$_2$NEt$_2$ | 16 (0.5) | 16 (0.5) | 14 (3.0) | 15 (3.0) | 0 (3.0) |
| 7,10-(OH)$_2$ | CH$_2$CH$_2$NHCH$_2$CH$_2$NMe$_2$ | CH$_2$CH$_2$NH$_2$ | — | — | 16 (3.0) | 0 (3.0) | 0 (3.0) |
| 7,10-(OH)$_2$ | (CH$_2$)$_3$NHCH$_2$CH$_2$OH | CH$_2$CH$_2$NH$_2$ | — | — | 14 (0.5) | 0 (3.0) | 0 (3.0) |
| 7,10-(OH)$_2$ | CH$_2$CH$_2$NHCH$_2$CH$_2$OH | CH$_2$CH$_2$CH$_2$NH$_2$ | — | — | 16 (3.0) | 0 (3.0) | 0 (3.0) |
| 7 10-(OH)$_2$ | CH$_2$CH$_2$NHCH$_2$CH$_2$NMe$_2$ | CH$_2$CH$_2$CH$_2$NH$_2$ | — | — | 15 (3.0) | 0 (3.0) | 0 (3.0) |
| 7-OH | CH$_2$CH$_2$NHCH$_2$CH$_2$OH | CH$_2$CH$_2$NHCH$_2$CH$_2$OH | — | — | 14 (0.5) | 0 (3.0) | 0 (3.0) |
| 10-OH | CH$_2$CH$_2$NHCH$_2$CH$_2$OH | CH$_2$CH$_2$NHCH$_2$CH$_2$OH | — | — | 14 (3.0) | 0 (3.0) | 0 (3.0) |
| 7-OH | CH$_2$CH$_2$NHCH$_3$ | CH$_2$CH$_2$NHCH$_2$CH$_2$OH | — | — | 15 (3.0) | 14 (3.0) | 0 (3.0) |
| H | Cl* | (CH$_2$)$_2$NEt$_2$ | 14 (0.5) | 14 (0.5) | 16 (0.1) | 16 (1.0) | 16 (0.5) |
| H | Cl* | (CH$_2$)$_2$NH$_2$ | 25 (0.1) | 16 (0.1) | 14 (3.0) | 0 (3.0) | 16 (3.0) |
| H | Cl* | (CH$_2$)$_2$NH(CH$_2$)$_2$OH | 18 (0.5) | 16 (0.1) | 16 (0.1) | 15 (3.0) | 0 (3.0) |
| H | Cl* | CH$_2$CHOHCH$_2$NEt$_2$ | 17 (3.0) | 14 (0.5) | 14 (1.0) | 15 (1.0) | 16 (1.0) |
| 7,10-(OH)$_2$ | Cl* | CH$_2$CHOHCH$_2$NEt$_2$ | 0 (3.0) | 14 (0.5) | 14 (3.0) | 14 (3.0) | 14 (3.0) |
| 7,10-(OH)$_2$ | Cl* | (CH$_2$)$_2$NEt$_2$ | 0 (3.0) | 0 (3.0) | 14 (1.0) | 0 (3.0) | 16 (3.0) |
| 7,10-(OH)$_2$ | Cl* | (CH$_2$)$_2$NMe$_2$ | 15 (3.0) | 14 (1.0) | 0 (3.0) | 0 (3.0) | 15 (0.5) |
| 7,10-(OH)$_2$ | Cl* | (CH$_2$)$_2$NH(CH$_2$)$_2$OH | 14 (1.0) | 14 (0.5) | 0 (3.0) | 0 (3.0) | 0 (3.0) |
| 7,10-(OH)$_2$ | Cl* | (CH$_2$)$_2$NH(CH$_2$)$_2$NMe$_2$ | 0 (3.0) | 0 (3.0) | 14 (3.0) | 0 (3.0) | 0 (3.0) |
| 7,10-(OH)$_2$ | Cl* | (CH$_2$)$_2$NH$_2$ Me | 14 (1.0) | 15 (3.0) | 0 (3.0) | 0 (3.0) | 0 (3.0) |
| 7,10-(OH)$_2$ | Cl* | (CH$_2$)$_2$N(CH$_2$)$_2$OH | 0 (3.0) | 14 (3.0) | 0 (3.0) | 0 (3.0) | 0 (3.0) |
| 7,10-(OH)$_2$ | Cl* | (CH$_2$)$_3$NH$_2$ | | | | | |
| | (CH$_2$)$_2$NH(CH$_2$)$_2$OH | CH$_2$CH$_2$NEt$_2$ | 18 (0.5) | 15 (0.5) | 20 (0.1) | 16 (0.5) | 15 (3.0) |
| | (CH$_2$)$_2$NEt$_2$ | CH$_2$CH$_2$NEt$_2$ | 16 (0.5) | 14 (0.5) | 19 (0.1) | 15 (0.5) | 16 (1.0) |
| | (CH$_2$)$_2$NH(CH$_2$)$_2$OH | (CH$_2$)$_2$NH(CH$_2$)$_2$OH | 17 (0.5) | 20 (1.0) | 16 (0.5) | 0 (3.0) | 0 (3.0) |

*Substituent bonded directly to aromatic ring.

In addition to their usefulness as antibiotic and antifungal agents, certain of the compounds of the invention display in vivo antileukemic activity when tested by the following procedure.

The in vivo lymphocytic leukemia P388 test is carried out by the United States National Cancer Institute. The animals used are either male or female CD2F$_1$ mice. There are six to seven animals per test group. The tumor transplant is by intraperitoneal injection of dilute ascitic fluid containing cells of lymphocytic leukemia P388. The test compounds are administered intraperitoneally in two single doses with a four-day interval between doses at various dose levels following tumor inoculation. The animals are weighed and survivors are recorded on a regular basis for 30 days. A ratio of survival time for treated (T)/control (C) animals is calculated. The criterion for efficacy is T/C×100>125%. The positive control compound in this test is 1,4-dihydroxy-5,8-[bis[[2-[(2-hydroxyethyl)amino]-ethyl]amino]-9,10-anthracenedione given at dosages ranging from 12.0 to 0.075 mg/kg. See Cancer Chemotherapy Reports, Part 3, 3, 1 (1972) for a comprehensive discussion of the protocol.

Utilizing this procedure, the following results were obtained for representative compounds of the invention.

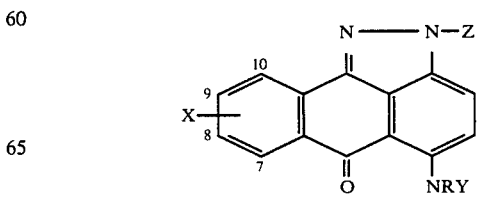

| X | Z | NRY | Dose mg/kg | T/C × 100 (Percent) |
|---|---|---|---|---|
| 7,10-(OH)$_2$ | (CH$_2$)$_2$N(Me)$_2$ .2HCl | NH(CH$_2$)$_2$NH(CH$_2$)$_2$OH | 12.5<br>6.25<br>3.12<br>1.56<br>0.78 | 242, 182<br>214, 214<br>192, 171<br>163<br>161 |
| 7,10-(OH)$_2$ | (CH$_2$)$_2$N(Me)$_2$ .2HCl | NH(CH$_2$)$_2$NH$_2$ | 12.5<br>6.25<br>3.12<br>1.56<br>0.78 | 283, 245 Cures<br>216, 192<br>182, 173<br>194, 149<br>194, 146 |
| 7,10-(OH)$_2$ | (CH$_2$)$_2$N(Et)$_2$ .2HCl | NH(CH$_2$)$_2$N(Et)$_2$ | 100<br>50<br>25<br>12.5 | 180, 174<br>168, 154, 146<br>140, 143, 149<br>132, 114, 140 |
| H | (CH$_2$)$_2$N(Et)$_2$ .2HCl | NH(CH$_2$)$_2$N[CH$_2$]$_2$O | 400<br>200<br>100 | 211<br>190, 148<br>145, 126 |
| H | (CH$_2$)$_2$N(Et)$_2$ .2HCl | NH(CH$_2$)$_2$NH(CH$_2$)$_2$OH | 25<br>12.5<br>6.25<br>3.12<br>1.56<br>0.78 | 197<br>161, 152, 178<br>145, 146, 161, 178<br>128, 142, 164, 151<br>142, 142, 146<br>135 |
| 7,10-(OH)$_2$ | (CH$_2$)$_2$NEt)$_2$ .2HCl | NH(CH$_2$)$_2$NH(CH$_2$)$_2$OH | 12.5<br>6.25<br>3.12<br>1.56<br>0.78<br>0.39 | 264, 212<br>180, 180, 164<br>164, 164, 166<br>148, 149, 155<br>140, 151, 159<br>152, 126 |
| 7,10-(OH)$_2$ | (CH$_2$)$_2$N(Et)$_2$ .2HBr | NH(CH$_2$)$_2$NHMe | 50<br>25<br>12.5<br>6.25<br>3.12 | 172<br>219 Cures<br>191<br>163<br>154 |
| 7,10-(OH)$_2$ | (CH$_2$)$_2$N(Et)$_2$ .2HCl | NH(CH$_2$)$_2$NH$_2$ | 25<br>12.5<br>6.25<br>3.12<br>1.56 | 179 Cures<br>280, 189 Cures<br>189, 191<br>154, 160<br>172 |
| 7,10-(OH)$_2$ | (CH$_2$)$_2$NH(CH$_2$)$_2$N(Me) | NH(CH$_2$)$_2$NH(CH$_2$)$_2$OH | 50<br>25<br>12.5<br>6.25<br>3.12 | 226<br>226, 169 Cures<br>179, 219<br>188, 191<br>207 |
| 7,10-(OH)$_2$ | (CH$_2$)$_2$NH(CH$_2$)$_2$OH .2HCl | NCH$_3$(CH$_2$)$_2$N(Me)$_2$ | 12.5<br>6.25 | 188<br>179 |
| 7,10-(OH)$_2$ | (CH$_2$)$_2$NH(CH$_2$)$_2$OH .2HCl | N[(CH$_2$)$_2$]$_2$NMe | 25<br>12.5<br>6.25 | 150<br>169<br>163 |
| H | (CH$_2$)$_2$NH(CH$_2$)$_2$OH .2HCl | NH(CH$_2$)$_2$N(Me)$_2$ | 25<br>12.5<br>6.25<br>3.12 | 162<br>166, 168<br>163, 174<br>158 |
| 7,10-(OH)$_2$ | (CH$_2$)$_2$NH(CH$_2$)$_2$OH .2HCl | NH(CH$_2$)$_2$N(Me)$_2$ | 25<br>12.5<br>6.25<br>3.12<br>1.56<br>0.78 | 88 Cures<br>220, 250 Cures<br>165, 182<br>165, 165<br>161, 165<br>152 |
| H | (CH$_2$)$_2$NH(CH$_2$)$_2$OH .2HCl | NH(CH$_2$)$_2$N(Et)$_2$ | 25<br>12.5<br>6.25<br>3.12<br>1.56 | 149<br>150, 155, 158, 160<br>138, 146, 150, 142<br>143, 143, 144, 151<br>138, 133 |
| 7,10-(OH)$_2$ | (CH$_2$)$_2$NH(CH$_2$)$_2$OH .2HCl | NH(CH$_2$)$_2$N(Et)$_2$ | 50<br>25<br>12.5<br>6.25<br>3.12<br>1.56 | 241<br>190, 209 Cures<br>177, 190<br>154, 168<br>148, 150<br>131, 135 |
| 7,10-(OH)$_2$ | (CH$_2$)$_2$NH(CH$_2$)$_2$OH .2HCl | NH(CH$_2$)$_2$NH(CH$_2$)$_2$N(Me)$_2$ | 50<br>25<br>12.5<br>6.25<br>3.12 | 200, 254 Cures<br>207, 228, 129 Cures<br>157, 179, 188<br>169, 172<br>152, 163 |
| H | (CH$_2$)$_2$NH(CH$_2$)$_2$OH .CH$_3$CO$_2$H | NH(CH$_2$)$_2$NH(CH$_2$)$_2$OH | 50<br>25<br>12.5<br>6.25 | 199<br>171, 185, 185<br>148, 189, 166<br>147, 157, 166 |

-continued

| X | Z | NRY | Dose mg/kg | T/C × 100 (Percent) |
|---|---|---|---|---|
| | | | 3.12 | 138, 150, 166 |
| | | | 1.56 | 132, 142 |
| 7,10-(OH)$_2$ | (CH$_2$)$_2$NH(CH$_2$)$_2$OH .2HCl | NH(CH$_2$)$_2$NH(CH$_2$)$_2$OH | 50 | 139 |
| | | | 25 | 158, 168 |
| | | | 12.5 | 153, 177 |
| | | | 6.25 | 206 Cures |
| | | | 3.12 | 187, 187 |
| | | | 1.56 | 158, 168 |
| H | (CH$_2$)$_2$NH(CH$_2$)$_2$OH .2HCl | NH(CH$_2$)$_2$NH$_2$ | 25 | 189 |
| | | | 12.5 | 175, 180 |
| | | | 6.25 | 146, 180 |
| | | | 3.12 | 162, 173 |
| | | | 1.56 | 150 |
| 7,10-(CH)$_2$ | (CH$_2$)$_2$NH(CH$_2$)$_2$OH .2HCl | NH(CH$_2$)$_2$NH$_2$ | 3.12 | 158, 196 Cures |
| | | | 1.56 | 173, 187 Cures |
| | | | 0.78 | 182 |
| | | | 0.39 | 175 |
| 7,10-(OH)$_2$ | (CH$_2$)$_2$NH(CH$_2$)$_2$OH .2HCl | NH(CH$_2$)$_3$NH(CH$_2$)$_2$OH | 6.25 | 169, 254 Cures |
| | | | 3.12 | 173, 186 |
| | | | 1.56 | 201, 166 |
| 7,10-(OH)$_2$ | (CH$_2$)$_2$NH(CH$_2$)$_2$OH .2CHl | NH(CH$_2$)$_3$NH$_2$ | 100 | 131 Cures |
| | | | 50 | 254, 272 Cures |
| | | | 25 | 207, 250 Cures |
| | | | 12.5 | 177, 190 |
| | | | 6.25 | 165, 172 |
| | | | 3.12 | 165, 165 |
| 7,10-(OH)$_2$ | (CH$_2$)$_2$NH(CH$_2$)$_2$OH .HCl | NH(CH$_2$)$_4$NH$_2$ | 100 | 172, 173 |
| | | | 50 | 139, 165 |
| | | | 25 | 150, 152 |
| | | | 12.5 | 139, 145 |
| | | | 6.25 | 131 |
| | | | 3.12 | 130 |
| 7,10-(OH)$_2$ | (CH$_2$)$_2$NH(CH$_2$)$_2$OH .2HCl | NH(CH$_2$)$_5$NH$_2$ | 100 | 150 |
| | | | 50 | 127, 139 |
| | | | 25 | 127, 127 |
| | | | 12.5 | 127 |
| H | (CH$_2$)$_2$NH$_2$ .2HCl | NH(CH$_2$)$_2$NH(CH$_2$)$_2$OH | 25 | 187, 187 |
| | | | 12.5 | 173, 177 |
| | | | 6.25 | 158, 173 |
| | | | 3.12 | 149, 158 |
| | | | 1.56 | 139 |
| 7,10-(OH)$_2$ | (CH$_2$)$_2$NH$_2$ .2HCl | NH(CH$_2$)$_2$NH(CH$_2$)$_2$OH | 25 | 257 Cures |
| | | | 12.5 | 182 |
| | | | 6.25 | 163 |
| | | | 3.12 | 160 |
| | | | 1.56 | 153 |
| 7,10-(OH)$_2$ | (CH$_2$)$_2$OMe .HCl | NH(CH$_2$)$_2$NH(CH$_2$)$_2$OH | 100 | 139, 140 |
| | | | 50 | 135 |
| | | | 25 | 127, 131 |
| | | | 12.5 | 127 |
| 7,10-(OH)$_2$ | (CH$_2$)$_2$OH .2HCl | NH(CH$_2$)$_2$N(Me)$_2$ | 200 | 157, 283 Cures |
| | | | 100 | 225, 242 |
| | | | 50 | 180, 182, 182 |
| | | | 25 | 153, 157, 173 |
| | | | 12.5 | 124, 135, 139 |
| 7,10-(OH)$_2$ | (CH$_2$)$_2$OH .2HCl | NH(CH$_2$)$_2$N(Et)$_2$ | 400 | 190 |
| | | | 300 | 177 |
| | | | 200 | 167 |
| | | | 150 | 155 |
| | | | 100 | 149 |
| | | | 75 | 135 |
| | | | 37.5 | 135 |
| | | | 25 | 128 |
| 7,10-(OH)$_2$ | (CH$_2$)$_2$OH .HCl | NH(CH$_2$)$_2$NH(CH$_2$)$_2$OH | 200 | 196, 271 |
| | | | 100 | 172, 184 |
| | | | 50 | 163, 165 |
| | | | 25 | 165, 187 |
| | | | 12.5 | 158, 163 |
| | | | 6.25 | 143, 163 |
| 7,10-(OH)$_2$ | (CH$_2$)$_2$OH .2HCl | NH(CH$_2$)$_2$NH$_2$ | 100 | 172, 196 |
| | | | 50 | 162, 172 |
| | | | 25 | 146, 154 |
| | | | 12.5 | 145, 151 |
| | | | 6.25 | 135 |
| 7,10-(OH)$_2$ | (CH$_2$)$_2$SMe .2HCl | NH(CH$_2$)$_2$NH(CH$_2$)$_2$OH | 12.5 | 132 |
| | | | 6.25 | 140 |
| 7,10-(OH)$_2$ | CH$_2$CHOHCH$_2$N(Et)$_2$ .2HCl | NH(CH$_2$)$_2$N(Et)$_2$ | 100 | 157 |
| | | | 50 | 131, 135 |
| | | | 25 | 131, 135 |
| | | | 12.5 | 128 |

-continued

| X | Z | NRY | Dose mg/kg | T/C × 100 (Percent) |
|---|---|---|---|---|
| 7,10-(OH)$_2$ | CH$_2$CHOHCH$_2$N(Et)$_2$ .2HCl | NH(CH$_2$)$_2$NH(CH$_2$)$_2$OH | 12.5 | 182, 223 Cures |
| | | | 6.25 | 128, 203 |
| | | | 3.12 | 128, 188, 189 |
| | | | 1.56 | 139 |
| | | | 0.78 | 132 |
| 7,10-(OH)$_2$ | CH$_2$CHOHCH$_2$N(Et)$_2$ .2HCl | NH(CH$_2$)$_2$NH$_2$ | 12.5 | 142, 210 |
| | | | 6.25 | 166, 189, 262 Cures |
| | | | 3.12 | 166, 182, 202 |
| | | | 1.56 | 157, 146 |
| | | | 0.78 | 132, 179 |
| | | | 0.39 | 135 |
| 7,10-(OH)$_2$ | Me .HCl | NH(CH$_2$)$_2$NH(CH$_2$)$_2$OH | 100 | 174 |
| | | | 50 | 162, 164 |
| | | | 25 | 150, 164 |
| | | | 12.5 | 140, 149 |
| | | | 6.25 | 133, 155 |
| | | | 3.12 | 138 |
| 7,10-(OH)$_2$ | CH$_2$CH$_2$NH$_2$ .2HCl | NHCH$_2$CH$_2$NH$_2$ | 25 | 156, 218 |
| | | | 12.5 | 144, 203, 221 |
| 7,10-(OH)$_2$ | CH$_2$CH$_2$NMe$_2$ .2HCl | NHCH$_2$CH$_2$NH$_2$ | 12.5 | 205, 208 |
| | | | 6.25 | 196 Cures |
| 7,10-(OH)$_2$ | CH$_2$CH$_2$CH$_2$NMe$_2$ .2HCl | NHCH$_2$CH$_2$NHCH$_2$CH$_2$OH | 12.5 | 218, 203 |
| | | | 6.25 | 185, 167 |
| 7,10-(OH)$_2$ | CH$_2$CH(OH)CH$_2$OH .HCl | NHCH$_2$CH$_2$NHCH$_2$CH$_2$OH | 400 | 281, 255 |
| | | | 200 | 218, 213 |
| | | | 100 | 208, 194 Cures |
| | | | 50 | 177 |
| | | | 25 | 184, 166 |
| 7,10-(OH)$_2$ | CH$_2$CH$_2$CH$_2$NMe$_2$ .2HCl | NHCH$_2$CH$_2$CH$_2$NH$_2$ | 25 | 194, 212 |
| | | | 12.5 | 173, 180 |
| | | | 6.25 | 167, 173, 190 |
| 7,10-(OH)$_2$ | CH$_2$CH$_2$CH$_2$NMe$_2$ .2HCl | NHCH$_2$CH$_2$NH$_2$ | 12.5 | 224 Cures |
| | | | 6.25 | 186, 200 |
| | | | 3.12 | 191, 180 |
| 7,10-(OH)$_2$ | CH$_2$CH$_2$NMeCH$_2$CH$_2$OH .1.6HCl | NHCH$_2$CH$_2$NHCH$_2$CH$_2$OH | 12.5 | 203 |
| | | | 6.25 | 182 |
| | | | 3.12 | 184 |
| 7,10-(OH)$_2$ | CH$_2$CH$_2$NHCH$_2$CH$_2$OH .2.1HCl | NH(CH$_2$)$_3$N(CH$_2$CH$_2$OH)$_2$ | 100 | 192 |
| | | | 50 | 167 |
| | | | 25 | 163 |
| 7,10-(OH)$_2$ | CH$_2$CH$_2$NHCH$_2$CH$_2$OH .HCl | NHCH$_2$CH$_2$NHCH$_2$CH$_2$NH$_2$ | 25 | 221, 227 Cures |
| | | | 12.5 | 233, 231 Cures |
| | | | 6.25 | 194, 157 |
| 7,10-(OH)$_2$ | CH$_2$CH$_2$NHCH$_2$CH$_2$OH .2.3HCl | NHCH$_2$CH$_2$N(CH$_2$CH$_2$OH)$_2$ | 100 | 223, 254 |
| | | | 50 | 203, 169 |
| | | | 25 | 187, 194 |
| | | | 12.5 | 158, 166 |
| 7,10-(OH)$_2$ | CH$_2$CH$_2$NHCH$_2$CH$_2$OH .2.75HCl | NH(CH$_2$)$_3$NH(CH$_2$)$_4$NH(CH$_2$)$_3$NH$_2$ | 12.5 | 145, 117 |
| | | | 6.25 | 127, 109 |
| 7,10-(OH)$_2$ | (CH$_2$)$_3$NHCH$_2$CH$_2$OH | NHCH$_2$CH$_2$NHCH$_2$CH$_2$OH | 100 | 259 Cures |
| | | | 50 | 222, 183 |
| | | | 25 | 183, 174 |
| | | | 12.5 | 157, 146 |
| 7,10-(OH)$_2$ | (CH$_2$)$_3$NHCH$_2$CH$_2$OH .0.1HCl | NHCH$_2$CH$_2$CH$_2$NH$_2$ | 100 | 185, 155 |
| | | | 50 | 160, 146 |
| 7,10-(OH)$_2$ | CH$_2$CH$_2$NHCH$_2$CH$_2$OH .CH$_3$CO$_2$H.HBr | NHCH$_2$CH$_2$NHCH$_3$ | 12.5 | 277, 275 Cures |
| | | | 6.25 | 277, 275 Cures |
| | | | 3.12 | 268, 177 Cures |
| 7,10-(OH)$_2$ | CH$_2$CH$_2$NH$_2$ .3.3HCl | NHCH$_2$CH$_2$NHCH$_2$CH$_2$NMe$_2$ | 50 | 220 Cures |
| | | | 25 | 192, 177 |
| | | | 12.5 | 186, 167 |
| 7,10-(OH)$_2$ | CH$_2$CH$_2$NH$_2$ .2.1HCl | NHCH$_2$CH$_2$CH$_2$NHCH$_2$CH$_2$OH | 6.25 | 184, 194 |
| | | | 3.12 | 177, 184 |
| | | | 1.56 | 181, 172 |
| 7,10-(OH)$_2$ | CH$_2$CH$_2$CH$_2$NH$_2$ .2HCl | NHCH$_2$CH$_2$NHCH$_2$CH$_2$OH | 50 | 285 Cures |
| | | | 25 | 285 Cures |
| | | | 12.5 | 247, 163 Cures |
| | | | 6.25 | 193, 134 |
| 7,10-(OH)$_2$ | CH$_2$CH$_2$CH$_2$NH$_2$ .3HCl | NHCH$_2$CH$_2$NHCH$_2$CH$_2$NMe$_2$ | 25 | 228, 130 |
| | | | 12.5 | 219, 123 |
| 7,10-(OH)$_2$ | CH$_2$CH$_2$NHCH$_3$ .2HCl | NHCH$_2$CH$_2$NHCH$_2$CH$_2$OH | 12.5 | 147 |
| 7-OH | CH$_2$CH$_2$NHCH$_2$CH$_2$OH .2HCl | NHCH$_2$CH$_2$NHCH$_2$CH$_2$OH | 25 | 285, 184 Cures |
| | | | 12.5 | 228, 142 Cures |
| | | | 6.25 | 183, 134 |
| 10-OH | CH$_2$CH$_2$NHCH$_2$CH$_2$OH .2.1HCl | NHCH$_2$CH$_2$NHCH$_2$CH$_2$OH | 100 | 221, 184 |
| | | | 50 | 172, 162 |
| | | | 25 | 163, 155 |
| 7,8,10-(OH)$_3$ | CH$_2$CH$_2$NHCH$_2$CH$_2$OH | NHCH$_2$CH$_2$NHCH$_2$CH$_2$OH | 25 | 265 Cures |

| X | Z | NRY | Dose mg/kg | T/C × 100 (Percent) |
|---|---|---|---|---|
| 7,9,10-(OH)$_3$ | .2.1HCl<br>CH$_2$CH$_2$NHCH$_2$CH$_2$OH<br>.2.1HCl | NHCH$_2$CH$_2$NHCH$_2$CH$_2$OH | 12.5<br>3.12<br>1.56 | 257 Cures<br>165<br>155 |

Antileukemic Activity of Chloroanthrapyrazoles Against Leukemias

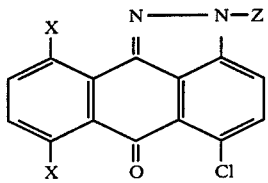

| | | L1210 Leukemia | P388 Leukemia in Mice | |
|---|---|---|---|---|
| X | Z | In Vitro*<br>ID$_{50}$ Molar | Dose<br>(mg/kg) | T/C × 100<br>(Percent) |
| H | (CH$_2$)$_2$NH(CH$_2$)$_2$OH.CH$_3$CO$_2$H | 3.9 × 10$^{-7}$ | 200<br>100 | 148, 126<br>124 |
| OH | (CH$_2$)$_2$NH(CH$_2$)$_2$OH.HCl | 6.6 × 10$^{-7}$ | 50<br>25<br>12.5<br>6.25 | 161, 161<br>143, 145<br>138, 140<br>131 |
| OH | (CH$_2$)$_2$NH$_2$.HCl | 6.3 × 10$^{-7}$ | 50 | 125 |

*Procedure described in Europ. J. Cancer 17, 671 (1981)

Broad Spectrum Antitumor Activity* of 2-[2-(Diethylamino)ethyl]-7,10-dihydroxy-5-[[2-[(2-hydroxyethyl)amino]ethyl]amino]anthra[1,9-cd]pyrazol-6(2H)—one Dihydrochloride in Mice

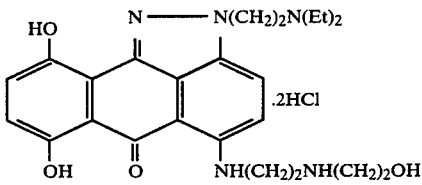

| Tumor | Route Tumor/Drug | Regimen | Dose (mg/kg) | T/C × 100 (Percent) | % Tumor Reduction |
|---|---|---|---|---|---|
| ADJ-PC6 Plasmacytoma | IP/IP | Q04D × 03 | 16<br>8<br>4<br>2 | 163<br>235<br>216<br>207 | |
| B16 Melanoma (BDF1) | IP/IP | Q01D × 09 | 8<br>4 | 176<br>151 | |
| B16 Melanoma (B6C3F1) | IP/IP | Q01D × 09 | 6<br>3 | 189<br>148 | |
| Colon 38 (BDF1) | SC/IP | Q01D × 09 | 16 | | 71 |
| L1210 Leukemia (CDF1) | IP/IP | Q01D × 09 | 16<br>8<br>4<br>2<br>1 | 133<br>240<br>178<br>144<br>137 | |
| M5076 Ovary | IP/IP | Q04D × 04 | 10<br>5<br>2.5<br>1.25 | 260<br>186<br>233<br>143 | |

*Procedure described in Cancer Chemotherapy Reviews, 7, 167 (1980) and references cited therein.

In addition to their usefulness as antibiotic and antifungal agents and as antileukemic agents, certain of the compounds of the invention display in vitro activity against solid tumors when tested by the following procedure.

HCT-8 (human colon adenocarcinoma) cells are trypsinized using Trypsin-EDTA. A single cell suspension is achieved by passing the cells through a 26 gauge needle with a 20 cc syringe. A cell suspension is prepared using RPMI 1640 growth medium (available from Gibco Laboratories) +10% fetal calf serum +50 µg/ml garamycin with a cell concentration of approximately 30,000 cells/ml. The cell suspension is dispensed in Linbro 24-well plates; 1 ml/well. The plates are incubated for approximately 48 hrs at 37° C. in a 5% $CO_2$ atmosphere. At this time test compounds are added in the appropriate concentration. Five µl of the 200 µg/ml stock solution is added to each well in a primary test. Ten µl of the appropriate dilution is added to each well for a titration test. The plates are reincubated an additional 60-65 hrs at 37° C. in a 5% $CO_2$ atmosphere. The test is read by lysing the cells using a mix of cationic surfactant, glacial acetic acid and sodium chloride. Two ml of the lysed cell suspension from each well is added to 8 ml of diluent. Each sample is read with a Coulter counter (ZBI model). The activity of each sample is measured as a percentage of the controls and the data is reported as $ID_{50}$, that is the molar quantity of drug required to kill 50% of the tumor cells.

Utilizing this procedure, the following results were obtained for representative compounds of the invention.

In Vitro Activity of Aminoanthrapyrazoles Against Human Colon Adenocarcinoma

| X | $Z_s$ | $NRY_s$ | $ID_{50}$ Molar |
|---|---|---|---|
| H | $(CH_2)_2NEt_2.2HCl$ | $NH(CH_2)_2NEt_2$ | $1.4 \times 10^{-7}$ |
| H | $CH_3.2HCl$ | $NH(CH_2)_2NEt_2$ | $4.1 \times 10^{-7}$ |
| H | $(CH_2)_2OH.2HCl$ | $NH(CH_2)_2NEt_2$ | $1.8 \times 10^{-6}$ |
| H | H.HCl | $NH(CH_2)_2NH(CH_2)_2OH$ | $1.5 \times 10^{-6}$ |
| H | $CH_3.HCl$ | $NH(CH_2)_2NH(CH_2)_2OH$ | $4.0 \times 10^{-7}$ |
| H | $(CH_2)_2NEt_2.2HCl$ | $NH(CH_2)_2NH_2$ | $5.2 \times 10^{-8}$ |
| H | $(CH_2)_2NH(CH_2)_2OH.CH_3CO_2H$ | $NH(CH_2)_2NH(CH_2)_2OH$ | $9.6 \times 10^{-7}$ |

| X | Z | NRY | $ID_{50}$ Molar |
|---|---|---|---|
| H | $(CH_2)_2NH(CH_2)_2OH.2HCl$ | $NH(CH_2)_2NH_2$ | $4.2 \times 10^{-8}$ |
| H | $(CH_2)_2NH(CH_2)_2OH.2HCl$ | $NH(CH_2)_2NEt_2$ | $1.2 \times 10^{-7}$ |
| H | $(CH_2)_2NH(CH_2)_2OH.2HCl$ | $NH(CH_2)_2NMe_2$ | $2.3 \times 10^{-7}$ |
| H | $(CH_2)_2NH(CH_2)_2OH.HCl$ | $NHCH_3$ | $2.8 \times 10^{-7}$ |
| H | $(CH_2)_2OH.2HCl$ | $NH(CH_2)_3NEt_2$ | $4.8 \times 10^{-7}$ |
| H | $(CH_2)_2NEt_2.2HCl$ | $NH(CH_2)_2N{\bigcirc}O$ (morpholine) | $1.2 \times 10^{-7}$ |
| H | $(CH_2)_2NEt_2.2HCl$ | $NH(CH_2)_3NEt_2$ | $1.8 \times 10^{-7}$ |
| H | $(CH_2)_2NEt_2.2HCl$ | $NH(CH_2)_4NEt_2$ | $2.2 \times 10^{-7}$ |
| H | $(CH_2)_2NEt_2.2HCl$ | $NH(CH_2)_7NEt_2$ | $2.2 \times 10^{-6}$ |
| H | $(CH_2)_2NEt_2.3HBr$ | $NH(CH_2)_2N{\bigcirc}NH$ (piperazine) | $3.8 \times 10^{-7}$ |
| H | $(CH_2)_2NH_2.2HCl$ | $NH(CH_2)_2NH(CH_2)_2OH$ | $6.8 \times 10^{-8}$ |
| 7,10-$(OH)_2$ | $(CH_2)_2NEt_2.2HCl$ | $NH(CH_2)_2NH(CH_2)_2OH$ | $2.7 \times 10^{-7}$ |
| 7,10-$(OH)_2$ | $(CH_2)_2NEt_2.2HCl$ | $NH(CH_2)_2NEt_2$ | $6.4 \times 10^{-7}$ |
| 7,10-$(OH)_2$ | $CH_3.HCl$ | $NH(CH_2)_2NH(CH_2)_2OH$ | $7.9 \times 10^{-7}$ |
| 7,10-$(OH)_2$ | $(CH_2)_2NEt_2.2HCl$ | $NH(CH_2)_2NH_2$ | $3.8 \times 10^{-7}$ |
| 7,10-$(OH)_2$ | $(CH_2)_2NEt_2.2HBr$ | $NH(CH_2)_2NHMe$ | $1.2 \times 10^{-7}$ |
| 7,10-$(OH)_2$ | $(CH_2)_2NMe_2.2HCl$ | $NH(CH_2)_2NH(CH_2)_2OH$ | $1.8 \times 10^{-7}$ |
| 7,10-$(OH)_2$ | $CH_2CHOHCH_2NEt_2.2HCl$ | $NH(CH_2)_2NH_2$ | $4.6 \times 10^{-7}$ |
| 7,10-$(OH)_2$ | $CH_2CHOHCH_2NEt_2.2HCl$ | $NH(CH_2)_2NH(CH_2)_2OH$ | $6.9 \times 10^{-7}$ |
| 7,10-$(OH)_2$ | $(CH_2)_2OH.HCl$ | $NH(CH_2)_2NMe_2$ | $1.7 \times 10^{-7}$ |
| 7,10-$(OH)_2$ | $(CH_2)_2NMe_2.2HCl$ | $NH(CH_2)_2NH_2$ | $1.4 \times 10^{-7}$ |
| 7,10-$(OH)_2$ | $(CH_2)_2NH_2.2HCl$ | $NH(CH_2)_2NH(CH_2)_2OH$ | $1.7 \times 10^{-6}$ |
| 7,10-$(OH)_2$ | $(CH_2)_2NH(CH_2)_2OH.2HCl$ | $N{\bigcirc}N-CH_3$ (N-methylpiperazine) | $5.4 \times 10^{-7}$ |
| 7,10-$(OH)_2$ | $(CH_2)_2NH_2.2HCl$ | $NH(CH_2)_2NH_2$ | $9.1 \times 10^{-7}$ |
| 7,10-$(OH)_2$ | $(CH_2)_2NMe_2.2HCl$ | $NH(CH_2)_3NH_2$ | $1.1 \times 10^{-6}$ |
| 7,10-$(OH)_2$ | $(CH_2)_3NMe_2.2HCl$ | $NH(CH_2)_3NH_2$ | $3.5 \times 10^{-7}$ |
| 7,10-$(OH)_2$ | $CH_2CH_2CH_2NMe_2.2HCl$ | $NHCH_2CH_2NHCH_2CH_2OH$ | $9.2 \times 10^{-8}$ |
| 7,10-$(OH)_2$ | $CH_2CH_2NMeCH_2CH_2OH1.6HCl$ | $NHCH_2CH_2NHCH_2CH_2OH$ | $4.5 \times 10^{-7}$ |

-continued

| | In Vitro Activity of Aminoanthrapyrazoles Against Human Colon Adenocarcinoma | | |
|---|---|---|---|
| 7,10-(OH)$_2$ | CH$_2$CH$_2$NHCH$_2$CH$_2$OH.1.8HCl | NHCH$_2$CH$_2$NHCH$_3$ | $4.0 \times 10^{-7}$ |
| 7,10-(OH)$_2$ | CH$_2$CH$_2$NH$_2$.3.3HCl | NHCH$_2$CH$_2$NHCH$_2$CH$_2$NMe$_2$ | $1.2 \times 10^{-6}$ |
| 7,10-(OH)$_2$ | CH$_2$CH$_2$NH$_2$.2.1HCl | NH(CH$_2$)$_3$NHCH$_2$CH$_2$OH | $2.8 \times 10^{-7}$ |
| 7,10-(OH)$_2$ | CH$_2$CH$_2$NH$_2$.2.9HCl | NHCH$_2$CH$_2$CH$_2$NH$_2$ | $8.5 \times 10^{-7}$ |
| 7,10-(OH)$_2$ | CH$_2$CH$_2$CH$_2$NH$_2$.2HCl | NHCH$_2$CH$_2$NHCH$_2$CH$_2$OH | $7.7 \times 10^{-7}$ |
| 7,10-(OH)$_2$ | CH$_2$CH$_2$NHCH$_3$.2HCl | NHCH$_2$CH$_2$NHCH$_2$CH$_2$OH | $2.3 \times 10^{-7}$ |
| 7-OH | CH$_2$CH$_2$NHCH$_2$CH$_2$OH.2HCl | NHCH$_2$CH$_2$NHCH$_2$CH$_2$OH | $6.1 \times 10^{-8}$ |
| 10-OH | CH$_2$CH$_2$NHCH$_2$CH$_2$OH.2.1HCl | NHCH$_2$CH$_2$NHCH$_2$CH$_2$OH | $1.1 \times 10^{-6}$ |
| 7-OH | CH$_2$CH$_2$NHCH$_2$CH$_2$OH.1.8HCl | NHCH$_2$CH$_2$NHMe | $2.7 \times 10^{-8}$ |

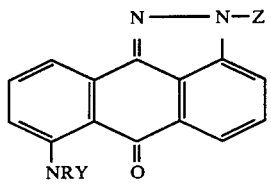

| Z | NRY | ID$_{50}$ Molar |
|---|---|---|
| (CH$_2$)$_2$NEt$_2$.2HCl | NH(CH$_2$)$_2$NEt$_2$ | $2.2 \times 10^{-7}$ |
| (CH$_2$)$_2$NEt$_2$.2HCl | NH(CH$_2$)$_2$NH(CH$_2$)$_2$OH | $9.3 \times 10^{-8}$ |

When being utilized as antibiotic and antifungal agents, the compounds of the invention can be prepared and administered in a wide variety of topical, oral, and parenteral dosage forms. It will be clear to those skilled in the art that the following dosage forms may comprise as the active component, either a compound of formula I, certain of the compounds of formula II or a corresponding pharmaceutically acceptable salt of one of said compounds or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well known procedures. See for example Remington's Pharmaceutical Sciences, Chapter 43, 14th ed. 1970, Mack Publishing Co., Easton Pennsylvania 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged form.

The quantity of active compound in a unit dose of preparation may be varied or adjusted from 50 mg to 500 mg according to the particular application and the potency of the active ingredient.

In therapeutic use as antibiotic and antifungal agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropyl-cellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

The following nonlimiting examples illustrate the inventors' preferred methods for preparing the compounds of the invention.

EXAMPLE 1

2-[2-(Diethylamino)ethyl)]-5-[[2-(diethylamino)ethyl]amino]anthra[1,9-cd]pyrazol-6(2$\underline{H}$)-one A mixture of 1.2 g (3.4 mmol) 5-chloro-2-[2-(diethylamino)ethyl]anthra[1,9-cd]pyrazol-6(2$\underline{H}$)-one, 1.0 g (8 mmol) of N,N-diethylethylenediamine, about 1 mg of anhydrous cuprous chloride and 30 ml of anhydrous 2-ethoxyethanol is heated at reflux under argon. After seven hours, an additional 0.5 g (4 mmol) of the diamine and about 1 mg of catalyst is added and the mixture is refluxed for 23 hours, cooled, and concentrated. The residue is dissolved in dichloromethane, washed successively with water, dilute ammonium hydroxide, and brine. Chromatography of the dried dichloromethane layer over silica gel with 10:1:89 methanol:triethylamine:dichloromethane provides the purified product. Dissolution in hot 2-propanol followed by treatment with excess hydrogen chloride in 2-propanol affords 1.2 g of the dried product as a salt with 2.1 equivalents of hydrogen chloride solvated with 1.2 equivalents of water; mp 262°–276° C. (decomposition).

5-Chloro-2-[2-(diethylamino)ethyl]anthra[1,9-cd]pyrazol-6(2$\underline{H}$)-one is prepared as follows:

A mixture of 4.15 g (15 mmol) of 1,4-dichloro-9,10-anthracenedione [*J. Amer. Chem. Soc.* 48; 3198 (1926)] 2.6 g (20 mmol) of (2-diethylaminoethyl)hydrazine [*J. Med. Chem.*, 1; 493, (1964)], and 35 ml of pyridine is heated at reflux for ten hours, cooled, and concentrated. The residue is dissolved in dichloromethane and washed with water. Chromatography of the dried dichloromethane layer over silica gel with ethyl acetate and then 95:5 ethyl acetate:methanol affords 3.8 g of a solid whose crystallization from 2-propanol gives 2.9 g of pure material; mp 90°–92° C.

Dissolution of 0.89 g of the product in hot 2-propanol followed by treatment with excess hydrogen chloride in 2-propanol affords 0.9 g of the hydrochloride salt; mp 263°–266° C. (decomposition).

EXAMPLE 2

2-[2-(Diethylamino)ethyl)]-5-[[2-[(2-hydroxyethyl)amino]ethyl]amino]anthra[1,9-cd]pyrazol-6(2H)-one A mixture of 2.5 g (7.1 mmol) of 5-chloro-2-[2-(diethylamino)ethyl]anthra[1,9-cd]pyrazol-6(2H)-one, 1 g (9 mmol) of 2-(2-aminoethylamino)ethanol and catalytic amounts of anhydrous cuprous chloride and potassium iodide in 25 ml of anhydrous 2-ethoxyethanol is heated at reflux under argon. Additional 0.5–1.0 g portions of the amine and catalytic amounts of the halide salts are added after six and 12 hours, respectively. After a total reflux time of 30 hours, the mixture is worked up as described for Example 1, with purification on silica gel utilizing first 10:1:89 and then 15:1:84 methanol:triethylamine:ethyl acetate. Following treatment with hydrogen chloride, there is obtained 1.1 g of the dried product as a salt with 2.0 equivalents of hydrogen chloride solvated with 2.4 equivalents of water; mp 239°–241° C. (decomposition).

EXAMPLE 3

5-[(2-Aminoethyl)amino]-2-[2-(diethylamino)ethyl]anthra[1,9-cd]pyrazol-6(2H)-one A mixture of 1.6 g (4.5 mmol) of 5-chloro-2-[2-(diethylamino)ethyl]anthra[1,9-cd]pyrazol-6(2H)-one, 2.5 ml of anhydrous ethylenediamine, and 25 ml of anhydrous pyridine is heated at reflux under argon for seven hours, cooled, diluted with toluene, and concentrated. The solid residue is dissolved in dichloromethane, washed with water, and then brine. Chromatography of the dried dichloromethane layer over silica gel with 1:9 methanol:dichloromethane provides 0.8 g of the product. Dissolution in hot 2-propanol followed by treatment with excess hydrogen chloride in 2-propanol affords 1.0 g of dried product as a salt with 2.0 equivalents of hydrogen chloride solvated with 1.8 equivalents of water; mp 276°–279° C. (decomposition).

The following compounds are prepared as described in Example 3 from 5-chloro-2-[2-(diethylamino)ethyl]anthra[1,9-cd]pyrazol-6(2H)-one and the corresponding amine:

EXAMPLE 4

2-[2-(Diethylamino)ethyl]-[[2-(4-morpholinyl)ethyl)]amino]anthra[1,9-cd]pyrazol-6(2H)-one Reaction with 4-(2-aminoethyl)morpholine gives the product as a salt with 2.0 equivalents of hydrogen chloride solvated with 1.2 equivalents of water; mp 288°–290° C. (decomposition).

EXAMPLE 5

2-[2-(Diethylamino)ethyl]-5-[[3-(diethylamino)propyl]amino]anthra[1,9-cd]pyrazol-6(2H)-one Reaction with N,N-diethyl-1,3-propanediamine gives the product as a salt with 2.0 equivalents of hydrogen chloride solvated with 0.2 equivalent of water; mp 270°–272° C. (decomposition).

EXAMPLE 6

2-[2-(Diethylamino)ethyl]-5-[[7-(diethylamino)heptyl]amino]anthra[1,9-cd]pyrazol-6(2H)-one Reaction with N,N-diethyl-1,7-heptanediamine gives the product as a salt with 2.0 equivalents of hydrogen chloride solvated with 0.3 equivalent of water; mp 190°–192° C. (decomposition).

EXAMPLE 7

5-[[4-(Diethylamino)butyl]amino]-2-[2-(diethylaminoethyl]anthra[1,9-cd]pyrazol-6(2H)-one Reaction with N,N-diethyl-1,4-butanediamine gives the product as a salt with 2.0 equivalents of hydrogen chloride solvated with 0.7 equivalent of water; mp 243°–246° C. (decomposition).

EXAMPLE 8

2-[2-(Diethylamino)ethyl]-5-(hexylamino)anthra[1,9-cd]-pyrazol-6(2H)-one

Reaction with n-hexylamine gives the product as a salt with 1.0 equivalent of hydrogen chloride solvated with 0.1 equivalent of water; mp 176°–179° C. (decomposition).

EXAMPLE 9

2-[2-(Diethylamino)ethyl]-5-[[2-(1-piperazinyl)ethyl]amino]anthra[1,9-cd]pyrazol-6(2H)-one Reaction with 4-(2-aminoethyl)-1-piperazine carboxylic acid, benzyl ester, then hydrolysis of the isolated intermediate with hot 48% hydrobromic acid in acetic acid gives the product as a salt with 3.3 equivalents of hydrogen bromide solvated with 1.4 equivalents of water and 0.1 equivalent of acetic acid; mp 284°–287° C. (decomposition).

4-(2-Aminoethyl)-1-piperazine carboxylic acid, benzyl ester, is prepared from 4-(2-aminoethyl)-1piperazine by a procedure analogous to that described for the preparation of (2-aminoethyl)-methylcarbamic acid, benzyl ester, in U.S. Pat. No. 3,931,268; $^1$H NMR (deuteriochloroform): δ 2.78 (triplet), 5.08 (singlet), 7.30 (singlet).

EXAMPLE 10

5-[[2-(Diethylamino)ethyl]amino]-2-methylanthra[1,9-cd]pyrazol-6(2H)-one

A mixture of 1.88 g (7 mmol) of 5-chloro-2-methylanthra[1,9-cd]pyrazol-6(2H)-one [*J. Chem. Soc.*, 1630 (1952)], 1.2 g (10 mmol) of N,N-diethylethylenediamine, 0.14 g of anhydrous potassium fluoride, and 10 ml of dimethylsulfoxide is heated at reflux under argon for four hours, cooled, diluted with water, and extracted with dichloromethane. The dichloromethane extract is washed twice with brine and then with 5% aqueous hydrochloric acid. The acid solution is washed with dichloromethane, made basic with sodium carbonate, and extracted with dichloromethane. The dried dichloromethane layer is clarified with charcoal, filtered, and concentrated to a residue. The salt was made as described in Example 3 to afford 1.1 g of the dried product, after thorough washing with ether, as a salt with 1.8 equivalents of hydrogen chloride solvated with 0.7 equivalent of water; mp 260°–264° C. (decomposition).

EXAMPLE 11

5-[[2-[(2-Hydroxyethyl)amino]ethyl]amino]-2-methylanthra[1,9-cd]pyrazol-6(2H)-one A mixture of 1.75 g (6.5 mmol) of 5-chloro-2-methylanthra[1,9-cd]pyrazol-6(2H)-one, 6 ml (59 mmol) of 2-(2-aminoethylamino)ethanol, catalytic amounts of anhydrous cuprous chloride and potassium iodide, and 25 ml of 2-methoxyethanol is heated at reflux under argon for four hours, cooled, and concentrated. The residue is dissolved in dichloromethane, washed with water, and then with 5% aqueous hydrochloric acid. The acid solution is washed with dichloromethane, made basic, and extracted into dichloromethane. Chromatography of the dried dichloromethane extract over silica gel with gradient elution employing 5–15% methanol in dichloromethane provides the purified product. The salt was made as described in Example 3 to afford 0.69 g of the dried product as a salt with 1.0 equivalent of hydrogen chloride solvated with 0.1 equivalent of water; mp 270°–272° C. (decomposition).

EXAMPLE 12

2-(2-Hydroxyethyl)-5-[[2-[(2-hydroxyethyl)amino]ethyl]amino]anthra[1,9-cd]pyrazol-6(2H)-one A mixture of 896 mg (3 mmol) of 5-chloro-2-(2-hydroxyethyl)anthra[1,9-cd]pyrazol-6(2H)-one, 3.1 ml (30 mmol) of 2-(2-aminoethylamino)ethanol, and 6 ml of anhydrous pyridine is heated at reflux under argon for 8.5 hours, cooled, and concentrated to leave a residue. Trituration from ether: 2-propanol leaves a gummy solid which upon further trituration from methanol-ether provides 851 mg of the product. Dissolution in chloroform followed by treatment with excess hydrogen chloride in 2-propanol affords 923 mg of the dried product as a salt with 1.6 equivalents of hydrogen chloride solvated with 0.5 equivalent of water; mp 267°–272° C. (decomposition).

5-Chloro-2-(2-hydroxyethyl)anthra[1,9-cd]pyrazol-6(2H)-one is prepared as follows:

A mixture of 5.54 g (20 mmol) of 1,4-dichloro-9,10-anthracenedione, 2.2 ml (33.3 mmol) of (2-hydroxyethyl)hydrazine and 20 ml of dry pyridine is stirred at 60° C. for 32 hours and concentrated. A solid residue is triturated with ether and then crystallized from chloroform to give 3.58 g of product; mp 209°–211° C. Processing of the mother liquor affords 0.21 g of additional product; mp 208°–210° C.

EXAMPLE 13

5-[[2-(Diethylamino)ethyl]amino]-2-(2-hydroxyethyl)anthra[1,9-cd]pyrazol-6(2H)-one Reaction of 896 mg (3 mmol) of 5-chloro-2-(2-hydroxyethyl)anthra[1,9-cd]pyrazol-6(2H)-one, 4.2 ml (30 mmol) of N,N-diethylethylenediamine, and 6 ml of anhydrous pyridine as described in Example 12 gives 1.02 g of the dried product as a salt with 1.75 equivalents of hydrogen chloride solvated with 0.5 equivalent of water; mp 199°–205° C. (decomposition).

The following compounds are prepared as described in Example 12 from 5-chloro-2-(2-hydroxyethyl)anthra[1,9-cd]pyrazol-6(2H)-one and the corresponding amine:

EXAMPLE 14

2-(2-Hydroxyethyl)-5-[[2-(4-morpholinyl)ethyl]amino][1,9-cd]pyrazol-6(2H)-one

Reaction with 4-(2-aminoethyl)morpholine gives the product as a salt with 1.9 equivalents of hydrogen chloride solvated with 0.5 equivalent of water; mp 260° C. (decomposition).

EXAMPLE 15

5-[[3-(Diethylamino)propyl]amino]-2-(2-hydroxyethyl)anthra[1,9-cd]pyrazol-6(2H)-one Reaction with N,N-diethyl-1-1,3-propanediamine gives the product as a salt with 2.0 equivalents of hydrogen chloride solvated with 0.5 equivalent of water; mp 201°–210° C. (decomposition).

EXAMPLE 16

5-[[4-(Diethylamino)butyl]amino]-2-(2-hydroxyethyl)anthra[1,9-cd]pyrazol-6(2H)-one Reaction with N,N-diethyl-1,4-propanediamine gives the product as a salt with 1.9 equivalents of hydrogen chloride solvated with 1.0 equivalent of water; mp 155°–185° C. (decomposition).

EXAMPLE 17

5-[[7-(Diethylamino)heptyl]amino]-2-(2-hydroxyethyl)anthra[1,9-cd]pyrazol-6(2H)-one Reaction with N,N-diethyl-1,7-heptanediamine gives the product as a salt with 1.0 equivalent of hydrogen chloride; mp 206°–208° C. (decomposition).

EXAMPLE 18

2-(2-Hydroxyethyl)-5-[[2-(1-piperazinyl)ethyl]amino]anthra[1,9-cd]pyrazol-6(2H)-one Reaction with 4-(2-aminoethyl)-1-piperazine carboxylic acid, benzyl ester, then hydrolysis of the isolated intermediate with refluxing 48% hydrobromic acid in acetic acid and salt formation gives the product as a salt with 2.0 equivalents of hydrogen chloride solvated with 0.5 equivalent of water; mp 292°–297° C. (decomposition).

EXAMPLE 19

5-[[2-[(2-Hydroxyethyl)amino]ethyl]amino]anthra[1,9-cd]pyrazol-6(2H)-one

A mixture of 2.54 g (10 mmol) of 5-chloroanthra[1,9-cd]pyrazol-6(2H)-one [*J. Chem. Soc.*, 1630 (1952)], 10 ml (100 mmol) of 2-(2-aminoethylamino)ethanol, and 25 ml of anhydrous pyridine is heated at reflux under argon for 24 hours, cooled, and concentrated. The residue is triturated with 2-propanol to give a solid whose dissolution in methanol:dichloromethane followed by salt formation as described in Example 3 affords 1.5 g of the dried product as a salt with 1.5 equivalents of hydrogen chloride solvated with 0.6 equivalent of water; mp 251°–254° C. (decomposition).

EXAMPLE 20

5-[[2-(Diethylamino)ethyl]amino]anthra[1,9-cd]pyrazol-6(2H)-one

A mixture of 1.6 g (6.3 mmol) of 5-chloroanthra[1,9-cd]pyrazol-6(2H)-one, 3.5 g (30 mmol) of N,N-diethylethylenediamine, and 20 ml of anhydrous pyridine is heated at reflux for 20 hours, cooled, and concentrated. The residue is dissolved in dichloromethane, washed with water, and then extracted with 1% aqueous hydrochloric acid. The acid solution is washed with dichloromethane, then made basic with aqueous sodium hydroxide. The aqueous solution is extracted with dichloromethane and the dried dichloromethane layer is concentrated to a residue which is converted into a salt as described for Example 3 to give 0.7 g of the dried product as a salt with 1.4 equivalents of hydrogen chloride solvated with 0.1 equivalent of water; mp 120°–130° C.

EXAMPLE 21

2-[2-[(2-Hydroxyethyl)amino]ethyl]-5-[[2-[(2-hydroxyethyl)amino]ethyl]amino]anthra[1,9-cd]pyrazol-6(2H)-one A mixture of 1.91 g (5 mmol) of 5-chloro-2-[2-[(2-hydroxyethyl)amino]ethyl]anthra[1,9-cd]pyrazol-6(2H)-one, hydrochloride, 2.6 ml of 2-(2-aminoethylamino)ethanol, and 5 ml of anhydrous pyridine is heated at reflux under argon for 6.5 hours, cooled, and concentrated. Trituration of the solid residue with cold 2-propanol gives 1.43 g of the dried product; mp 154°–156° C. Crystallization from glacial acetic acid: 2-propanol gives 1.35 g of the dried product as a salt with 1.0 equivalent of acetic acid solvated with 0.5 equivalent of water; mp 146°–148° C.

5-Chloro-2-[2-[(2-hydroxyethyl)amino]ethyl]anthra[1,9-cd]pyrazol-6(2H)-one is prepared as follows:

To a refluxing mixture of 832 mg (3 mmol) of 1,4-dichloro-9,10-anthracenedione in 8 ml of dry acetonitrile is added dropwise over 40 minutes, 450 mg (3.8 mmol) of 2-[(hydrazinoethyl)amino]ethanol in 3 ml of acetonitrile. The mixture is refluxed for one hour, cooled, and triturated with cold 2-propanol to give 602 mg of product; mp 140°–142° C. Processing of the mother liquor affords 71 mg of additional product; mp 124°–126° C. Crystallization of the free base from glacial acetic acid gives the diacetate salt; mp 125°–130° C. The hydrochloride salt is prepared as described in Example 3; mp 260°–263° C. (decomposition).

2-[(Hydrazinoethyl)amino]ethanol is prepared as follows:

A solution of 86.8 g (1.0 mol) of N-(2-hydroxyethyl)ethyleneimine and 400 ml (about 6 mol) of 54% aqueous hydrazine is heated at reflux for two days. Excess water and hydrazine is distilled at 40°–50° C./13 mm, then the pot residue is distilled at 142° C./0.10 mm to yield 80.9 g of product with an 88% purity. Careful redistillation of a small sample gives analytically pure material; bp 120° C./0.035 mm.

EXAMPLE 22

5-[(2-Aminoethyl)amino]-2-[2-[(2-hydroxyethyl)amino]ethyl]anthra[1,9-cd]pyrazol-6(2H)-one Reaction of 1.91 g of 5-chloro-2-[2-[(2-hydroxyethyl)amino]ethyl]anthra[1,9-cd]pyrazol-6(2H)-one hydrochloride with 1.6 ml (25 mmol) of 1,2-ethylenediamine, as described in Example 21, followed by concentration affords a solid which is washed with ether, 2-propanol, and a little dichloromethane, then triturated with methanol to remove a solid impurity. The concentrated filtrate is dissolved in water and purified over a column of HP-20 resin eluting first with water and then with methanol. Concentration of the methanol eluate followed by salt formation as described in Example 3 affords 1.0 g of the dried product as a salt with 2.0 equivalents of hydrogen chloride solvated with 0.9 equivalent of water; mp 263°–267° C. (decomposition).

EXAMPLE 23

5-[[2-(Diethylamino)ethyl]amino]-2-[2-[(2-hydroxyethyl)amino]ethyl]anthra[1,9-cd]pyrazol-6(2H)-one Reaction of 1.91 g of 5-chloro-2-[2-[(2-hydroxyethyl)amino]ethyl]anthra[1,9-cd]pyrazol-6(2H)-one, hydrochloride, with 3.5 ml (25 mmol) of N,N-diethylethylenediamine as described in Example 21 affords 1.4 g of product; mp 132°–133° C. Processing of the mother liquor affords 0.3 g of additional product; mp 130°–131° C. Salt formation as described for Example 3 gives 1.6 g of the dried product as a salt with 2.0 equivalents of hydrogen chloride solvated with 1.0 equivalent of water; mp 272°–274° C. (decomposition).

EXAMPLE 24

5-[(2-Hydroxyethyl)amino]-2-[2-[(2-hydroxyethyl)amino]ethyl]anthra[1,9-cd]pyrazol-6(2H)-one A mixture of 2.5 g (6.6 mmol) of 5-chloro-2-[2-[(2-hydroxyethyl)amino]ethyl]anthra[1,9-cd]pyrazol-6(2H)one, hydrochloride, 2 ml (33 mmol) of 2-aminoethanol and 13 ml of anhydrous pyridine is reacted and worked up as described in Example 21 to afford a solid precipitate whose salt formation as described in Example 3 affords 1.4 g of the dried product as a salt with 1.1 equivalents of hydrogen chloride solvated with 0.6 equivalent of water; mp 260°–261° C. (decomposition).

EXAMPLE 25

2-[2-[(2-Hydroxyethyl)amino]ethyl]-5-[[2-(dimethylamino)ethyl]amino]anthra[1,9-cd]pyrazol-6(2H)-one Reaction of 2.72 g (7 mmol) of 5-chloro-2-[2-[(2-hydroxyethyl)amino]ethyl]anthra[1,9-cd]pyrazol-6(2H)-one, hydrochloride, 1.2 g (14 mmol) of N,N-dimethylethylenediamine, and 20 ml of pyridine for 42 hours at reflux followed by workup as described in Example 21 gives a solid residue whose dissolution in hot methanol followed by salt formation as described in Example 3 gives 1.0 g of the dried product as a salt with 2.1 equivalents of hydrogen chloride solvated with 0.9 equivalent of water; mp 286°–288° C. (decomposition).

EXAMPLE 26

2-[2-[(2-Hydroxyethyl)amino]ethyl]-5-(methylamino)anthra[1,9-cd]pyrazol-6(2H)-one Reaction of 5-chloro-2-[2-[(2-hydroxyethyl)amino]ethyl]anthra[1,9-cd]pyrazol-6-(2H)-one, hydrochloride, with excess methylamine as described in Example 21 gives the product as a salt with 1.0 equivalent of hydrogen chloride; mp 285°–288° C. (decomposition).

EXAMPLE 27

2-(2-Aminoethyl)-5-[[2-[(2-hydroxyethyl)amino]ethyl]amino]anthra[1,9-cd]pyrazol-6(2H)-one A mixture of 3.0 g (8.9 mmol) of 2-(2-aminoethyl)-5-chloroanthra[1,9-cd]pyrazol-6(2H)-one, 2.0 ml of 2-(2-aminoethylamino)ethanol, and 15 ml of anhydrous pyridine is heated at reflux for 30 hours, cooled, and filtered. The filtrate is concentrated and chromatographed over silica gel with 99:2:1 dichloromethane:methanol:triethylamine, then gradient elution to 99:20:1 to provide the purified product. Salt formation as described in Example 3 gives 0.8 g of the dried product as a salt with 1.7 equivalents of hydrogen chloride solvated with 1.0 equivalent of water and 0.2 equivalent of 2-propanol; mp 270°–272° C. (decomposition).

2-(2-Aminoethyl)-5-chloroanthra[1,9-cd]pyrazol-6-(2H)-one is prepared as follows:

To a solution of 1.0 g (3.6 mmole) of 1,4-dichloro-9,10-anthracenedione in 10 ml of pyridine at 35° is added dropwise 1.9 ml of (2-aminoethyl)hydrazine [British Pat. No. 880,332]. The mixture is stirred for four hours, concentrated, and purified on silica gel utilizing 94:5:1 dichloromethane:methanol:triethylamine.

Salt formation as described in Example 3 gives 0.45 g of the product as a salt with 1.0 equivalent of hydrogen chloride solvated with 1.2 equivalents of water and 0.1 equivalent of 2-propanol; mp 284°–285° C. (decomposition).

EXAMPLE 28

2-[2-(Diethylamino)ethyl]-7,10-dihydroxy-5-[[2-[(2-hydroxyethyl)amino]ethyl]amino]anthra[1,9-cd]pyrazol-6(2H)-one Reaction of a mixture of 2.9 g (7.5 mmol) of 5-chloro-2-[2-(diethylamino)ethyl]-7,10-dihydroxyanthra[1,9-cd]pyrazol-6(2H)-one, 7.5 ml (75 mmol) of 2-(2-aminoethylamino)ethanol, and 35 ml of pyridine for four hours at reflux followed by workup as described in Example 21 and salt formation as described in Example 3 gives 2.8 g of the dried product as a salt with 2.0 equivalents of hydrogen chloride solvated with 0.7 equivalent of water; mp 198°–202° C. (decomposition).

5-Chloro-2-[2-(diethylamino)ethyl]-7,10-dihydroxyanthra[1,9-cd]pyrazol-6(2H)-one is prepared as follows:

Reaction of a mixture of 12.7 g (41 mmol) of 1,4-dichloro-5,8-dihydroxy-9,10-anthracenedione, 12 g (90 mmol) of (2-diethylaminoethyl)hydrazine, and 65 ml of pyridine at 50° C. for four hours followed by workup as described in Example 22 gives a residue that is dissolved in dichloromethane. Chromatography over silica gel with dichloromethane and then with 3% methanol in dichloromethane affords crude material whose crystallization from 2-propanol gives 6.5 g of a purified solid; mp 136°–140° C. Salt formation as described in Example 3 on 1.5 g of this material gives 1.3 g of a dried solid as a salt with 1.0 equivalent of hydrogen chloride solvated with 0.3 equivalent of water; mp 280°–282° C. (decomposition).

EXAMPLE 29

2-[2-(Diethylamino)ethyl]-5-[[2-(diethylamino)ethyl]amino]-7,10-dihydroxyanthra[1,9-cd]pyrazol-6(2H)-one Reaction of a mixture of 1.93 g (5 mmol) of 5-chloro-2-[2-(diethylamino)ethyl]-7,10-dihydroxyanthra-[1,9-cd]pyrazol-6(2H)-one, 2.9 g (24 mmol) of N,N-diethylethylenediamine, and 25 ml of pyridine for five hours at reflux followed by workup as described in Example 21 gives a crude solid which is dissolved in dichloromethane. Chromatography over silica gel with 3%, 6%, and 10% solutions of methanol in dichloromethane affords 1.6 g of pure material. Salt formation as described in Example 3 gives 1.4 g of the dried product as a salt with 2.0 equivalents of hydrogen chloride solvated with 0.3 equivalent of water; mp 290°–292° C. (decomposition).

EXAMPLE 30

5-[(2-Aminoethyl)amino]-2-[2-(diethylamino)ethyl]-7,10-dihydroxyanthra[1,9-cd]pyrazol-6(2H)-one Reaction of 5-chloro-2-[2-(diethylamino)ethyl]-7,10-dihydroxyanthra[1,9-cd]pyrazol-6(2H)-one with ethylenediamine as described in Example 28 gives the product as a salt with 2.0 equivalents of hydrogen chloride solvated with 1.7 equivalents of water and 0.1 equivalent of 2-propanol; mp 277°–281° C. (decomposition).

EXAMPLE 31

2-[2-(Diethylamino)ethyl]-7,10-dihydroxy-5-[[2-(methylamino)ethyl]amino]anthra[1,9-cd]pyrazol-6(2H)-one Reaction of 5-chloro-2-[2-(diethylamino)ethyl]-7,10-dihydroxyanthra[1,9-cd]pyrazol-6(2H)-one with (2-aminoethyl)-methylcarbamic acid, benzyl ester [U.S. Pat. No. 3,931,268] followed by isolation of the intermediate as described in Example 29 then hydrolysis with hot 48% hydrobromic acid in acetic acid gives the product as a salt with 2.3 equivalents of hydrogen bromide solvated with 2.7 equivalents of water; mp 217°–220° C. (decomposition).

EXAMPLE 32

2-[2-(Dimethylamino)ethyl]-7,10-dihydroxy-5-[[2-[(2-hydroxyethyl)amino]ethyl]amino]anthra[1,9-cd]pyrazol-6(2H)-one Reaction of 2.0 g (5.6 mmol) of 5-chloro-2-[2-(dimethylamino)ethyl]-7,10-dihydroxyanthra-[1,9-cd]pyrazol-6(2H)-one, 5.6 ml of 2-(2-aminoethylamino)ethanol, and 20 ml of pyridine at 70° C. for 24 hours followed by workup as described in Example 21 and salt formation as described in Example 3 gives 2.4 g of the dried product as a salt with 2.4 equivalents of hydrogen chloride solvated with 2.0 equivalents of water; mp 310°–313° C. (decomposition).

5-Chloro-2-[2-(dimethylamino)ethyl]-7,10-dihydroxyanthra[1,9-cd]pyrazol-6(2H)-one is prepared as follows:

Reaction of a mixture of 15.5 g (50 mmol) of 1,4-dichloro-5,8-dihydroxy-9,10-anthracenedione, 10.3 g (100 mmol) of (2-dimethylaminoethyl)hydrazine [*J. Med. Chem.*, 1;493 (1964)] and 60 ml of pyridine at 35° C. overnight followed by workup as described in Example 28 gives 3.8 g of product; mp 143°–146° C. Salt formation as described in Example 3 gives the product as a salt with 1.1 equivalents of hydrogen chloride solvated with 1.2 equivalents of water; mp 295°–300° C. (decomposition).

The following compounds are prepared as described in Example 32 from 5-chloro-2-[2-(dimethylamino)ethyl]-7,10-dihydroxyanthra[1,9-cd]pyrazol-6(2H)-one and the corresponding amine:

EXAMPLE 33

5-[(2-Aminoethyl)amino]-2-[2-(dimethylamino)ethyl]-7,10-dihydroxyanthra[1,9-cd]pyrazol-6(2H)-one Reaction with ethylenediamine gives the product as a salt with 1.9 equivalents of hydrogen chloride solvated with 2.4 equivalents of water; mp 300°–302° C. (decomposition).

EXAMPLE 34

5-[(3-Aminopropyl)amino]-2-[2-(dimethylamino)ethyl]-7,10-dihydroxyanthra[1,9-cd]pyrazol-6(2H)-one Reaction with 1,3-propanediamine gives the product as a salt with 1.9 equivalents of hydrogen chloride solvated with 1.4 equivalents of water; mp 281°–285° C. (decomposition).

EXAMPLE 35

5-[[2-(Diethylamino)ethyl]amino]-7,10-dihydroxy-2-(2-hydroxyethyl)anthra[1,9-cd]pyrazol-6(2H)-one Reaction of a mixture of 3.3 g (10 mmol) of 5-chloro-7,10-dihydroxy-2-(2-hydroxyethyl)anthra[1,9-cd]pyrazol-6(2H)-one, 14.5 ml (100 mmol) of N,N-diethylethylenediamine, and 20 ml of pyridine for three hours at reflux followed by workup as described in Example 21 gives 2.47 g of a solid, mp 197°–200° C. Salt formation as described in Example 12 affords 2.21 g of the dried product as a salt with 1.6 equivalents of hydrogen chloride solvated with 0.6 equivalent of water; mp 215°–219° C. (decomposition).

5-Chloro-7,10-dihydroxy-2-(2-hydroxyethyl)anthra[1,9-cd]pyrazol-6(2H)-one is prepared as follows:

A mixture of 12 g (40 mmol) of 1,4-dichloro-5,8-dihydroxy-9,10-anthracenedione, 4.5 g (60 mmol) of (2-hydroxyethyl)hydrazine, and 40 ml of pyridine is stirred at 50° C. overnight, cooled, and concentrated. The residue is triturated successively with chloroform and hot methanol to give 1.1 g of the dried product; mp 231°–234° C.

EXAMPLE 36

5-[[2-[(2-Hydroxyethyl)amino]ethyl]amino]-7,10-dihydroxy-2-(2-hydroxyethyl)anthra[1,9-cd]pyrazol-6(2H)-one A mixture of 3.3 g (10 mmol) of 5-chloro-7,10-dihydroxy-2-(2-hydroxyethyl)anthra[1,9-cd]pyrazol-6(2H)-one, 10.4 g (100 mmol) of 2-(2-aminoethylamino)ethanol, and 20 ml of pyridine is heated at reflux for four hours, cooled, and concentrated. Successive trituration of the residue with acetonitrile, 2-propanol, and methanol gives 1.35 g of a powder. Salt formation as described in Example 12 affords 1.06 g of the dried product as a salt with 1.0 equivalent of hydrogen chloride solvated with 0.5 equivalent of water; mp 196°–203° C. (decomposition).

The following compounds are prepared as described in Example 35 from 5-chloro-7,10-dihydroxy-2-(2-hydroxyethyl)anthra[1,9-cd]pyrazol-6(2H)-one and the corresponding amine:

EXAMPLE 37

5-[(2-Aminoethyl)amino]-7,10-dihydroxy-2-(2-hydroxyethyl)anthra[1,9-cd]pyrazol-6(2H)-one Reaction with ethylenediamine gives the product as a salt with 1.8 equivalents of hydrogen chloride solvated with 0.5 equivalent of water; mp > 195° C. (decomposition).

EXAMPLE 38

7,10-Dihydroxy-2-(2-hydroxyethyl)-5-[[2-(4-morpholinyl)ethyl]amino]anthra[1,9-cd]pyrazol-6(2H)-one Reaction with 4-(2-aminoethyl)morpholine gives the product as a salt with 0.4 equivalent of hydrogen chloride and 0.3 equivalent of water; mp 240°–251° C. (decomposition).

EXAMPLE 39

5-[[2-(Dimethylamino)ethyl]amino]-7,10-dihydroxy-2-(2-hydroxyethyl)anthra[1,9-cd]pyrazol-6(2H)-one Reaction with N,N-dimethylethylenediamine gives the product as a salt with 1.5 equivalents of hydrogen chloride solvated with 2.0 equivalents of water; mp 250° C. (decomposition).

EXAMPLE 40

5-[(2-Aminoethyl)amino]-7,10-dihydroxy-2-methylanthra[1,9-cd]pyrazol-6(2H)-one

Reaction of a mixture of 3.2 g (10.6 mmol) of 5-chloro-7,10-dihydroxy-2-methylanthra[1,9-cd]pyrazol-6(2H)-one, 5 ml (74 mmol) of ethylenediamine, and 55 ml of pyridine for seven hours at reflux followed by workup as described in Example 21 gives a solid residue. Dissolution of the solid in hot methanol and N,N-dimethylformamide followed by salt formation as described in Example 3 affords 1.5 g of the dried product as a salt with 1.0 equivalent of hydrogen chloride solvated with 0.2 equivalent of water and 0.1 equivalent of N,N-dimethylformamide; mp 323°–326° C. (decomposition).

5-Chloro-7,10-dihydroxy-2-methylanthra[1,9-cd]pyrazol-6(2H)-one is prepared as follows:

A mixture of 12.4 g (40 mmol) of 1,4-dichloro-5,8-dihydroxy-9,10-anthracenedione, 2.7 ml (50 mmol) of methylhydrazine, and 250 ml of pyridine is heated at 35° C. for seven hours, treated with an additional 1 ml of methylhydrazine, heated for seven hours at 35° C., and cooled. The solids are filtered and recrystallized from N,N-dimethylformamide to give 8.85 g of the dried product as a salt with 0.1 equivalent of hydrogen chloride, mp 298°–305° C. (decomposition).

EXAMPLE 41

7,10-Dihydroxy-5-[[2-[(2-hydroxyethyl)amino]ethyl]amino]-2-methylanthra[1,9-cd]pyrazol-6(2H)-one Reaction of a mixture of 3.25 g (10.8 mmol) of 5-chloro-7,10-dihydroxy-2-methylanthra[1,9-cd]pyrazol-6(2H)-one, 3 ml (30 mmol) of 2-(2-aminoethylamino)ethanol, and 50 ml of pyridine for seven hours at reflux followed by workup as described in Example 21 and salt formation as described in Example 3 gives 1.8 g of the dried product as a salt with 1.0 equivalent of hydrogen chloride solvated with 0.6 equivalent of water; mp 280°–284° C. (decomposition).

EXAMPLE 42

5-[[2-(Diethylamino)ethyl]amino]-7,10-dihydroxy-2-methylanthra[1,9-cd]pyrazol-6(2H)-one Reaction of a mixture of 2.0 g (6.7 mmol) of 5-chloro-7,10-dihydroxy-2-methylanthra[1,9-cd]pyrazol-6(2H)-one, 3.5 ml (20 mmol) of N,N-diethylethylenediamine, and 45 ml of pyridine for seven hours at reflux followed by workup as described in Example 21 and salt formation as described in Example 3 gives 1.7 g of the dried product as a salt with 1.5 equivalents of hydrogen chloride solvated with 0.8 equivalent of water; mp 298° C. (decomposition).

EXAMPLE 43

2-[3-(Diethylamino)-2-hydroxypropyl]-7,10-dihydroxy-5-[[2-[(2-hydroxyethyl)amino]ethyl]amino]anthra[1,9-cd]pyrazol-6(2H)-one Reaction of a mixture of 1.3 g (3 mmol) of 5-chloro-2-[3-(diethylamino)-2-hydroxypropyl]-7,10-dihydroxyanthra[1,9-cd]pyrazol-6(2H)-one, 2.1 ml (21 mmol) of 2-(2-aminoethylamino)ethanol, and 10 ml of pyridine at reflux for six hours followed by workup as described for Example 21 and salt formation as described in Example 3 gives the product as a salt with 2.2 equivalents of hydrogen chloride solvated with 2.8 equivalents of water and 0.2 equivalent 2-propanol; mp 105°–120° C.

5-Chloro-2-[3-(diethylamino)-2-hydroxypropyl]-7,10-dihydroxyanthra[1,9-cd]pyrazol-6(2H)-one is prepared as follows:

A mixture of 6.2 g (20 mmol) of 1,4-dichloro-5,8-dihydroxy-9,10-anthracenedione, 9.7 g (60 mmol) of 1-(diethylamino)-3-hydrazino-2-propanol (German Pat. No. 1,126,877) and 35 ml of pyridine is stirred at 40° C. for one hour then at room temperature overnight. The mixture is concentrated and purified on silica gel utilizing 97:2:1 dichloromethane methanol:triethylamine to give 1.7 g of product. Salt formation as described in Example 3 gives 1.4 g of the product as a salt with 1.0 equivalent of hydrogen chloride solvated with 0.7 equivalent of water; mp 264°–267° C. (decomposition).

EXAMPLE 44

5-[[2-(Diethylamino)ethyl]amino]-2-[3-(diethylamino)-2-hydroxypropyl]-7,10-dihydroxyanthra[1,9-cd]pyrazol-6(2H)-one Reaction of 5-chloro-2-[3-(diethylamino)-2-hydroxypropyl]-7,10-dihydroxyanthra[1,9-cd]pyrazol-6(2H)-one with N,N-diethylethylenediamine as described in Example 43 gives the product as a salt with 2.0 equivalents of hydrogen chloride solvated with 1.9 equivalents of water; mp 253°–255° C. (decomposition).

EXAMPLE 45

5-[(2-Aminoethyl)amino]-2-[3-(diethylamino)-2-hydroxypropyl]-7,10-dihydroxyanthra[1,9-cd]pyrazol-6(2H)-one Reaction of 5-chloro-2-[3-(diethylamino)-2-hydroxypropyl]-7,10-dihydroxyanthra[1,9-cd]pyrazol-6(2H)-one with ethylenediamine as described in Example 43 gives the product as a salt with 2.0 equivalents of hydrogen chloride solvated with 2.8 equivalents of water; mp 148°–152° C.

EXAMPLE 46

2-[3-(Dimethylamino)propyl]-7,10-dihydroxy-5-[[2-[(2-hydroxyethyl)amino]ethyl]amino]anthra[1,9-cd]pyrazol-6(2H)-one Reaction of a mixture of 2.5 g (6 mmol) of 5-chloro-2-[3-(dimethylamino)propyl]-7,10-dihydroxyanthra[1,9-cd]pyrazol-6(2H)-one, hydrochloride, 2.8 ml (28 mmol) of 2-(2-aminoethylamino)ethanol, and 20 ml of pyridine at reflux for 24 hours followed by workup as described for Example 21 and salt formation as described in Example 3 gives the product as a salt with 2.0 equivalents of hydrogen chloride solvated with 1.0 equivalent of water; mp 311° C. (decomposition).

5-Chloro-2-[3-(dimethylamino)propyl]-7,10-dihydroxyanthra[1,9-cd]pyrazol-6(2H)-one is prepared as follows:

To a suspension of 30.9 g (100 mmol) of 1,4-dichloro-5,8-dihydroxy-9,10-anthracenedione in 200 ml of pyridine at 37° C. is added dropwise 14 g (120 mmol) of (3-dimethylaminopropyl)hydrazine [*J. Med. Chem.*, 1;493 (1964)]. The mixture is diluted with 50 ml of N,N-dimethylformamide, stirred for ten hours, and concentrated. The residue is distributed between dichloromethane and 5% aqueous sodium bicarbonate. Purification of the dried organic layer on silica gel utilizing 95.5:4:0.5 dichloromethane:methanol:triethylamine gives 8 g of product. Salt formation as described in Example 3 gives 7.6 g of the product as a salt with 0.8 equivalent of hydrogen chloride solvated with 0.1 equivalent of 2-propanol; mp 267°–271° C. (decomposition).

EXAMPLE 47

5-[(3-Aminopropyl)amino]-2-[3-(dimethylamino)propyl]-7,10-dihydroxyanthra[1,9-cd]pyrazol-6(2H)-one Reaction of 5-chloro-2-[3-(dimethylamino)propyl]-7,10-dihydroxyanthra[1,9-cd]pyrazol-6(2H)-one, hydrochloride, with 1,3-propanediamine as described in Example 46 gives the product as a salt with 2.0 equivalents of hydrogen chloride solvated with 0.5 equivalent of water; mp>300° C.

EXAMPLE 48

7,10-Dihydroxy-5-[[2-[(2-hydroxyethyl)amino]ethyl]amino-2-[2-(methylthio)ethyl]anthra[1,9-cd]pyrazol-6(2H)-one Reaction of a mixture of 0.66 g (3.6 mol) of 5-chloro-2-(2-thiomethylethyl)-7,10-dihydroxyanthra[1,9-cd]pyrazol-6(2H)-one, 1.8 ml (18 mmol) of 2-(2-aminoethylamino)ethanol, and 16 ml of pyridine at reflux overnight followed by workup as described in Example 21 and salt formation as described in Example 3 gives 0.7 g of the dried product as a salt with 1.6 equivalents of hydrogen chloride solvated with 0.5 equivalent of water; mp>133° C. (decomposition).

5-Chloro-2-(2-thiomethylethyl)-7,10-dihydroxyanthra-[1,9-cd]pyrazol-6(2H)-one is prepared as follows:

An ice-cold mixture of 2.64 g (5 mmol) of 5-chloro-2-(2-thiomethylethyl)-7,10-bis(phenylmethoxy)anthra[1,9-cd]pyrazol-6(2H)-one in 15 ml dichloromethane is treated dropwise during 30 minutes with 30 ml of a 1M solution of boron trichloride in dichloromethane. The mixture is stirred for one hour then treated carefully with 30 ml of methanol. The mixture is warmed to room temperature overnight then concentrated to a residue which is triturated with 2-propanol to give a red solid. Further trituration with 75 ml of boiling methanol gives 0.9 g of pure product; mp 186°–190° C.

5-Chloro-2-(2-thiomethylethyl)-7,10-bis(phenylmethoxy)anthra[1,9-cd]pyrazol-6(2H)-one is prepared as follows:

A mixture of 5.1 g (10 mmol) of 5-chloro-2-(2-hydroxyethyl)-7,10-bis(phenylmethoxy)anthra-[1,9-cd]pyrazol-6(2H)-one, 9.4 g (100 mmol) of methyldisulfide, 20.2 g (100 mmol) of tri-n-butylphosphine, and 50 ml of N,N-dimethylformamide is stirred overnight at room temperature. The mixture is cooled and treated carefully with 75 ml of water. The orange solid is collected and washed successively with water, 2-propanol, and diethyl ether to give 5.1 g of the dried product; mp 155°–160° C.

5-Chloro-2-(2-hydroxyethyl)-7,10-bis(phenylmethoxy)anthra[1,9-cd]pyrazol-6(2H)-one is prepared as follows:

Reaction of a mixture of 35.4 g (72 mmol) of 1,4-dichloro-5,8-bis(phenylmethoxy)-9,10-anthracenedione, 11.2 g (147 mmol) of (2-hydroxyethyl)hydrazine, 2.1 g (37 mmol) of anhydrous potassium fluoride, 7.4 g (74 mmol) of anhydrous potassium bicarbonate, and 220 ml of dry dimethylsulfoxide as described in Example 54 gives 33.1 g of the dried product; mp 178°–184° C. Crystallization from chloroform raises the melting point to 201°–204° C.

1,4-Dichloro-5,8-bis(phenylmethoxy)-9,10-anthracenedione is prepared as follows:

A mixture of 51.3 g (160 mmol) of 1,4-dichloro-5,8-dihydroxy-9,10-anthracenedione (U.S. Pat. No. 3,631,074), 46 g (330 mmol) of powdered anhydrous potassium carbonate, 44 ml (380 mmol) of benzyl bromide, and 670 ml of dry acetone are heated at reflux for five days. The mixture is cooled, the solids are filtered, then washed sequentially with water, methanol, and diethyl ether to give 63.6 g of the dried product; mp 190°–194° C. Processing of the acetone filtrate gives 9.4 g of a second crop; mp 142°–155° C.

EXAMPLE 49

5-Chloro-2-[2-(diethylamino)ethyl]-7,10-dihydroxyanthra[1,9-cd]pyrazol-6(2H)-one An ice-cold mixture of 9.1 g (16 mmol) of 5-chloro-2-[2-(diethylamino)ethyl]-7,10-bis(phenylmethoxy)anthra[1,9-cd]pyrazol-6(2H)-one in 30 ml of dichloromethane is treated dropwise during two hours with 96 ml of a 1 M solution of boron trichloride. Following addition, the mixture is treated carefully with 30 ml of methanol. The mixture is warmed to room temperature overnight and the solid residue is collected, washed sequentially with 2-propanol, methanol, and diethyl ether to give 5.5 g of the dried product as a salt with 1.0 equivalent of hydrogen chloride, and solvated with 0.2 equivalent of water; mp 280°–282° C. (decomposition).

5-Chloro-2-[2-(diethylamino)ethyl]-7,10-bis(phenylmethoxy)anthra[1,9-cd]pyrazol-6(2H)-one is prepared as follows:

A mixture of 4.2 g (6.3 mmol) of 5-chloro-2-[2-[[(4-methylphenyl)sulfonyl]oxy]ethyl]-7,10-bis(phenylmethoxy)anthra[1,9-cd]pyrazol-6(2H)-one, 4.4 g (60 mmol) of diethylamine, 17 g (12.6 mmol) of powdered potassium carbonate, and 35 ml of dimethylsulfoxide is stirred overnight at 50° C. The mixture is cooled and diluted with 50 ml of water. The solid is collected and washed with water. The solid is crystallized from chloroform:2-propanol (3:1) to give 2.1 g of product; mp 209°–211° C.

5-Chloro-2-[2-[[(4-methylphenyl)sulfonyl]oxy]ethyl]-7,10-bis(phenylmethoxy)anthra[1,9-cd]pyrazol-6(2H)one is prepared as follows:

An ice-cold mixture of 22 g (43 mmol) of 5-chloro-2-(2-hydroxyethyl)-7,10-bis(phenylmethoxy)anthra[1,9-cd]pyrazol-6(2H)-one, 12.3 g (65 mmol) of p-toluenesulfonyl chloride and 170 ml of pyridine is stirred for 50 hours. The solid is filtered, washed with methanol and diethyl ether, and dried to give 10.5 g of the product; mp 203°–206° C. (decomposition). Processing of the filtrate gives 9.3 g of additional product; mp 182°–188° C. (decomposition).

EXAMPLE 50

2-[2-[[2-(Dimethylamino)ethyl]amino]ethyl]-5-[[2-[(2-hydroxyethyl)amino]ethyl]amino]-7,10-dihydroxyanthra-[1,9-cd]pyrazol-6(2H)-one Reaction of a mixture of 3.6 g (7.4 mmol) 5-chloro-2-[2-[[2-(dimethylamino)ethyl]amino]ethyl]-7,10-dihydroxyanthra[1,9-cd]pyrazol-6(2H)-one, dihydrochloride, 4.5 ml (45 mmol) of 2-(2-aminoethylamino)ethanol, and 35 ml of pyridine at 80° C. overnight followed by workup as described in Example 21 gives 0.5 g of product as a salt with 0.25 equivalent of hydrogen chloride and solvated with 0.75 equivalent of water; mp 110°–117° C.

5-Chloro-2-[2-[[2-(dimethylamino)ethyl]amino]ethyl]-7,10-dihydroxyanthra[1,9-cd]pyrazol-6(2H)-one is prepared as follows:

An ice-cold mixture of 9.3 g (16 mmol) of 5-chloro-2-[2-[[2-(dimethylamino)ethyl]amino]ethyl]-7,10-bis(phenylmethoxy)anthra[1,9-cd]pyrazol-6(2H)-one in 30 ml of dichloromethane is treated dropwise during two hours with 96 ml of a 1 M solution of boron trichloride. Following addition, the mixture is treated carefully with 30 ml of methanol. The mixture is warmed to room temperature overnight and the solid residue is collected, washed sequentially with 2-propanol, methanol, and diethyl ether to give 3.68 g of the dried product as a salt with 1.8 equivalents of hydrogen chloride and solvated with 0.2 equivalent of 2-propanol and 0.8 equivalent of water; mp 260°–268° C. (decomposition).

5-Chloro-2-[2-[[2-(dimethylamino)ethyl]amino]ethyl]-7,10-bis(phenylmethoxy)anthra[1,9-cd]pyrazol-6(2H)-one is prepared as follows:

A mixture of 4.2 g (6.3 mmol) of 5-chloro-2-[2-[[(4-methylphenyl)sulfonyl]oxy]ethyl]-7,10-bis(phenylmethoxy)anthra[1,9-cd]pyrazol-6(2H)-one, 5.3 g (60 mmol) of N,N-dimethylethylenediamine, 17 g (12.6 mmol) of powdered potassium carbonate, and 35 ml of dimethylsulfoxide is stirred overnight at 50° C. The mixture is cooled and diluted with 50 ml of water. The solid is collected and washed with water. The solid is heated in dichloromethane, the solution filtered, then concentrated. Trituration of the residue with hot ethyl acetate gives 1.7 g of the dried product; mp 148°–153° C.

EXAMPLE 51

7,10-Dihydroxy-5-[[2-[(2-hydroxyethyl)amino]ethyl]-amino]-2-[2-[(2-hydroxyethyl)methylamino]ethyl]-anthra[1,9-cd]pyrazol-6(2H)-one Reaction of a mixture of 3.3 g (7.3 mmol) of 5-chloro-7,10-dihydroxy-2-[2-[(2-hydroxyethyl)methylamino]ethyl]anthra[1,9-cd]pyrazol-6(2H)-one, hydrochloride, 3.6 ml (36 mmol) of 2-(2-aminoethylamino)ethanol, and 30 ml of pyridine overnight at 80° C. followed by workup as described in Example 21 and salt formation as described in Example 3 gives 1.4 g of the dried product as a salt with 1.6 equivalents of hydrogen chloride solvated with 0.4 equivalent of water; mp 240° C. (decomposition).

5-Chloro-7,10-dihydroxy-2-[2-[(2-hydroxyethyl)methylamino]ethyl]anthra[1,9-cd]pyrazol-6(2H)-one is prepared as follows:

Reaction of a mixture of 8.3 g (15 mmol) of 5-chloro-2-[2-[(2-hydroxyethyl)methylamino]ethyl]-7,10-bis(phenylmethoxy)anthra[1,9-cd]pyrazol-6(2H)-one, 87 ml of a 1 M solution of boron trichloride in dichloromethane, and 60 ml of dichloromethane as described for Example 49 gives 3.5 g of the dried product as a salt with 1.0 equivalent of hydrogen chloride solvated with 1.75 equivalents of water; mp 279°–282° C. (decomposition).

5-Chloro-2-[2-[(2-hydroxyethyl)methylamino]ethyl]-7,10-bis(phenylmethoxy)anthra[1,9-cd]pyrazol-6(2H)-one is prepared as follows:

Reaction of a mixture of 10.0 g (15 mmol) of 5-chloro-2-[2-[[4-methylphenyl)sulfonyl]oxy]ethyl]-7,10-bis(-phenyl)methoxy)anthra[1,9-cd]pyrazol-6(2H)-one, 12.1 ml (150 mmol) of 2-methylaminoethanol, 4.1 g (30 mmol) of potassium carbonate, and 90 ml of dimethylsulfoxide as described in Example 49 gives 8.5 g of the product; mp 191°–194° C.

EXAMPLE 52

7,10-Dihydroxy-5-[[2-[(2-hydroxyethyl)amino]ethyl]-amino]-2-[3-[(2-hydroxyethyl)amino]propyl]anthra-[1,9-cd]pyrazol-6(2H)-one

Reaction of a mixture of 1.4 g (3.6 mmol) of 5-chloro-7,10-dihydroxy-2-[3-[(2-hydroxyethyl)amino]-propyl]anthra[1,9-cd]pyrazol-6(2H)-one, hydrochloride, 3.7 ml (37 mmol) of 2-(2-aminoethylamino)ethanol and 15 ml of pyridine overnight at 80° C. followed by workup as described in Example 21 gives 0.9 g of the dried product solvated with 0.6 equivalent of water; mp 100°–105° C.

5-Chloro-7,10-dihydroxy-2-[3-[(2-hydroxyethyl)amino]propyl]anthra[1,9-cd]pyrazol-6(2H)-one is prepared as follows:

Reaction of a mixture of 9.0 g (16 mmol) of 5-chloro-2-[3-[(2-hydroxyethyl)amino]propyl]-7,10-bis(phenylmethoxy)anthra[1,9-cd]pyrazol-6(2H)-one, 63 ml of a 1 M solution of boron trichloride in dichloromethane, and 30 ml of dichloromethane as described for Example 49 gives 6.0 g of the dried product as a salt with 0.8 equivalent of hydrogen chloride solvated with 0.7 equivalent of water; mp 255°–265° C. (decomposition).

5-Chloro-2-[3-[(2-hydroxyethyl)amino]propyl]7,10-bis(phenylmethoxy)anthra[1,9-cd]pyrazol-6(2H)-one is prepared as follows:

Reaction of a mixture of 13.4 g (19.7 mmol) of 5-chloro-2-[3-[[4-methylphenyl)sulfonyl]oxy]propyl]-7,10-bis(phenylmethoxy)anthra[1,9-cd]pyrazol-6(2H)-one, 12 ml (197 mmol) of 2-aminoethanol, 5.5 g (39.4 mmol) of potassium carbonate, and 120 ml of dimethylsulfoxide as described in Example 49 gives 9.85 g of the product; mp 174°–176° C. Crystallization from chloroform gives material of mp 180°–185° C.

5-Chloro-2-[3-[[4-methylphenyl)sulfonyl]oxy]propyl]-7,10-bis(phenylmethoxy)anthra[1,9-cd]pyrazol-6(2H)-one is prepared as follows:

Reaction of a mixture of 13.1 g (25 mmol) of 5-chloro-2-(3-hydroxypropyl)-7,10-bis(phenylmethoxy)anthra[1,9-cd]pyrazol-6(2H)-one, 9.5 g (50 mmol) of p-toluenesulfonyl chloride, 9 ml (65 mmol) of triethylamine, 150 mg of 4-dimethylaminopyridine, and 125 ml of dichloromethane at 5° C. for one day then at room temperature for five hours followed by workup as described for Example 49 gives 14.3 g of the product; mp 137°–139° C.

5-Chloro-2-(3-hydroxypropyl)-7,10-bis(phenylmethoxy)anthra[1,9-cd]pyrazol-6(2H)-one is prepared as follows:

A mixture of 48.9 g (100 mmol) of 1,4-dichloro-5,8-bis(phenylmethoxy)-9,10-anthracenedione, 18.0 g (200 mmol) of (3-hydroxypropyl)hydrazine [*J. Amer. Chem. Soc.* 76; 1283 (1954)], 2.9 g (50 mmol) of anhydrous potassium fluoride, 10.0 g (100 mmol) of anhydrous potassium bicarbonate, and 300 ml of dry dimethylsulfoxide is stirred at 80° C. overnight. The warm mixture is diluted with 1.5 ml of water, then allowed to cool. The solids are collected by filtration, washed sequentially with water, 2-propanol, and diethyl ether to afford 31.0 g of the dried product; mp 159°–163° C. Processing of the filtrate gives 4.7 g of additional product; mp 150°–154° C.

EXAMPLE 53

5-[(3-Aminopropyl)amino]-7,10-dihydroxy-2-[3-[(2-hydroxyethyl)amino]propyl]anthra[1,9-cd]pyrazol-6(2H)-one

Reaction of a mixture of 1.3 g (3.3 mmol) of 5-chloro-7,10-dihydroxy-2-[3-[(2-hydroxyethyl)amino]propyl]anthra[1,9-cd]pyrazol-6(2H)-one, 2.9 ml (35 mmol) of 1,3-propanediamine, and 15 ml of pyridine at 80° C. overnight followed by workup as described in Example 21 gives 1.0 g of the dried product as a salt with 0.1 equivalent of hydrogen chloride solvated with 0.3 equivalent of water and 0.1 equivalent of 2-propanol; mp 120°–130° C. (decomposition).

EXAMPLE 54

7,10-Dihydroxy-2-[2-[(2-hydroxyethyl)amino]ethyl]-5-[[2-[(2-hydroxyethyl)amino]ethyl]amino]anthra[1,9-cd]pyrazol-6(2H)-one

Reaction of mixture of 1.28 g (3 mmol) 5-chloro-7,10-dihydroxy-2[2-[(2-hydroxyethyl)amino]ethyl]-anthra[1,9-cd]pyrazol-6(2H)-one, hydrochloride, 1.5 ml (15 mmol) of 2-(2-aminoethylamino)ethanol and 6 ml of pyridine at 80° C. overnight followed by workup as described in Example 21 and salt formation as described in Example 3 gives 675 mg of the product as a salt with 2.0 equivalents of hydrogen chloride solvated with 0.9 equivalent of water; mp 215°–225° C. (decomposition).

5-Chloro-7,10-dihydroxy-2-[2-[(2-hydroxyethyl)amino]ethyl]anthra[1,9-cd]pyrazol-6(2H)-one is prepared as follows:

To an ice-cold mixture of 26.8 g (48 mmol) of 5-chloro-2-[2-[(hydroxyethyl)amino]ethyl]-7,10-bis(phenylmethoxy)anthra[1,9-cd]pyrazol-6(2H)-one and 60 ml of dry dichloromethane is added dropwise during 2¼ hours 794 ml of a 1 M solution of boron trichloride. The mixture is stirred for an additional 0.5 hours, then 200 ml of methanol is added dropwise during 1.5 hours. The mixture is allowed to warm to room temperature overnight and the solids are filtered, washed sequentially with methanol, dichloromethane, diethyl ether, and 2-propanol to give 14.7 g of the dried product; mp 175° C. (decomposition). Processing of the filtrate affords 5.4 g of additional product; mp 125°–135° C. (decomposition). Crystallization of the solid from methanol gives a salt with 1.0 equivalent of hydrogen chloride solvated with 0.7 equivalent of water; mp 180°–200° C. (decomposition).

5-Chloro-2-[2-[(2-hydroxyethyl)amino]ethyl]-7,10-bis(phenylmethoxy)anthra[1,9-cd]pyrazol-6(2H)-one is prepared as follows:

A mixture of 58.8 g (120 mmol) of 1,4-dichloro-5,8-bis(phenylmethoxy)-9,10-anthracenedione, 28.6 g (240 mmol) of 2-[(hydrazinoethyl)amino]ethanol, 3.5 g (60 mmol) of anhydrous potassium fluoride, 12 g (120 mmol) of anhydrous potassium bicarbonate, and 360 ml of dry dimethylsulfoxide is stirred at 80° C. overnight. The mixture is diluted with 400 ml of water and the orange solids are filtered, washed sequentially with water, 2-propanol, and diethyl ether to give 51.2 g of the dried product; mp 164°–168° C.

The following compounds are prepared as described in Example 54 from 5-chloro-7,10-dihydroxy-2-[2-[(2-hydroxyethyl)amino]ethyl]anthra[1,9-cd]pyrazol-6(2H)-one hydrochloride and the corresponding amine:

EXAMPLE 55

5-[(2-Aminoethyl)amino]-7,10-dihydroxy-2-[2-[(2-hydroxyethyl)amino]ethyl]anthra[1,9-cd]pyrazol6(2H̲)-one Reaction with ethylenediamine gives the product as a salt with 2.0 equivalents of hydrogen chloride solvated with 0.9 equivalent of water; mp 272°–278° C. (decomposition).

EXAMPLE 56

5-[[2-(Dimethylamino)ethyl]amino]-7,10-dihydroxy-2-[2-[(2-hydroxyethyl)amino]ethyl]anthra[1,9-cd]-pyrazol-6(2H̲)-one Reaction with N,N-dimethylethylenediamine gives the product as a salt with 1.9 equivalents of hydrogen chloride solvated with 1.7 equivalents of water; mp 278°–280° C. (decomposition).

EXAMPLE 57

5-[[2-(Diethylamino)ethyl]amino]-7,10-dihydroxy-2-[2-[(2-hydroxyethyl)amino]ethyl]anthra[1,9-cd]pyrazol-6(2H̲)-one Reaction with N,N-diethylethylenediamine gives the product as a salt with 1.9 equivalents of hydrogen chloride solvated with 1.5 equivalents of water; mp 228°–231° C.

EXAMPLE 58

5-[(3-Aminopropyl)amino]-7,10-dihydroxy-2-[2-[(2-hydroxyethyl)amino]ethyl]anthra[1,9-cd]pyrazol-6-(2H̲)-one Reaction with 1,3-propanediamine gives the product as a salt with 1.7 equivalents of hydrogen chloride solvated with 1.0 equivalent of water; mp 222° C. (decomposition).

EXAMPLE 59

5-[(4-Aminobutyl)amino]-7,10-dihydroxy-2-[2-[(2-hydroxyethyl)amino]ethyl]anthra[1,9-cd]pyrazol-6(2H̲)-one Reaction with 1,4-butanediamine gives the product as a salt with 1.0 equivalent of hydrogen chloride solvated with 0.5 equivalent of water; mp 240°–245° C. (decomposition).

EXAMPLE 60

5-[(5-Aminopentyl)amino]-7,10-dihydroxy-2-[2-[(2-hydroxyethyl)amino]ethyl]anthra[1,9-cd]pyrazol-6(2H̲)-one Reaction with 1,5-pentanediamine gives the product as a salt with 1.9 equivalents of hydrogen chloride solvated with 0.7 equivalent of water; mp 270°–275° C. (decomposition).

EXAMPLE 61

7,10-Dihydroxy-2-[2-[(2-hydroxyethyl)amino]ethyl]-5-[[2-(4-morpholinyl)ethyl]amino]anthra[1,9-cd]-pyrazol-6(2H̲)-one Reaction with 4-(2-aminoethyl)morpholine gives the product as a salt with 2.4 equivalents of hydrogen chloride solvated with 0.8 equivalent of water; mp 280° C. (decomposition).

EXAMPLE 62

7,10-Dihydroxy-2-[2-[(2-hydroxyethyl)amino]ethyl]-5-[[3-[(2-hydroxyethyl)amino]propyl]amino]anthra[1,9-cd]pyrazol-6(2H̲)-one Reaction with 2-(3-aminopropylamino)ethanol gives the product as a salt with 2.1 equivalents of hydrogen chloride solvated with 0.8 equivalent of water and 0.1 equivalent of 2-propanol; mp 170°–180° C. (decomposition).

EXAMPLE 63

5-[[2-[[2-(Dimethylaminoethyl]amino]ethyl]amino]-7,10-dihydroxy-2-[2-[(2-hydroxyethyl)amino]ethyl]anthra-[1,9-cd]pyrazol-6(2H̲)-one Reaction with N,N-dimethyldiethylenetriamine gives the product as a salt with 2.4 equivalents of hydrogen chloride solvated with 1.4 equivalents of water and 0.2 equivalent of 2-propanol; mp 80°–90° C. (decomposition).

EXAMPLE 64

7,10-Dihydroxy-2-[2-[(2-hydroxyethyl)amino]ethyl]-5-(4-methyl-1-piperazinyl)anthra[1,9-cd]pyrazol-6(2H̲)-one Reaction with N-methylpiperazine gives the product as a salt with 2.2 equivalents of hydrogen chloride solvated with 0.4 equivalent of water and 0.2 equivalent of 2-propanol; mp >123° C. (decomposition).

EXAMPLE 65

5-[[2-(Dimethylamino)ethyl]methylamino]-7,10-dihydroxy-2-[2-[(2-hydroxyethyl)amino]ethyl]anthra-[1,9-cd]-pyrazol-6(2H̲)-one Reaction with N,N,N-trimethylethylenediamine gives the product as a salt with 2.1 equivalents of hydrogen chloride solvated with 1.9 equivalents of water and 0.2 equivalents of 2-propanol; mp >91° C. (decomposition).

EXAMPLE 66

5-[[2-[(2-Aminoethyl)amino]ethyl]amino]-7,10-dihydroxy-2-[2-[(2-hydroxyethyl)amino]ethyl]anthra[1,9-cd]-pyrazol-6(2H̲)-one Reaction with diethylenetriamine gives the product as a salt with 1.0 equivalent of hydrogen chloride solvated with 1.0 equivalent of water; mp 210°–215° C. (decomposition).

EXAMPLE 67

5-[[2-[Bis(2-hydroxyethyl)amino]ethyl]amino]-7,10-dihydroxy-2-[2-[(2-hydroxyethyl)amino]ethyl]anthra-[1,9-cd]pyrazol-6(2H̲)-one Reaction with N,N-bis(2-hydroxyethyl)ethylenediamine gives the product as a salt with 2.3 equivalents of hydrogen chloride solvated with 0.8 equivalent of water; mp 230° C. (decomposition).

EXAMPLE 68

5-[[3-[Bis(2-hydroxyethyl)amino]propyl]amino]-7,10-dihydroxy-2-[2-hydroxyethyl)amino]ethyl]anthra-[1,9-cd]pyrazol-6(2H̲)-one Reaction with N,N-bis (2-hydroxyethyl)-1,3-propanediamine gives the product as a salt with 2.1 equivalents of hydrogen chloride solvated with 0.4 equivalent of water; mp 198°–215° C. (decomposition).

EXAMPLE 69

5-[[3-[[4-[(3-Aminopropyl)amino]butyl]amino]propyl]-amino]-7,10-dihydroxy-2-[2-[(2-hydroxyethyl)amino]-ethyl]anthra[1,9-cd]pyrazol-6(2H)-one Reaction with spermine gives the product as a salt with 2.75 equivalents of hydrogen chloride solvated with 0.6 equivalent of water and 0.1 equivalent of 2-propanol; mp 185°–200° C. (decomposition).

EXAMPLE 70

7,10-Dihydroxy-2-[2-[(2-hydroxyethyl)amino]ethyl]-5-[[2-(methylamino)ethyl]amino]anthra[1,9-cd]pyrazol-6(2H)-one Reaction with (2-aminoethyl)-methylcarbamic acid, benzyl ester followed by isolation of the intermediate then hydrolysis with refluxing 48% hydrobromic acid in acetic acid gives the product as a salt with 2.1 equivalents of hydrogen bromide solvated with 2.3 equivalents of water and 0.5 equivalent of acetic acid; mp 222°–228° C. (decomposition).

EXAMPLE 71

2-(2-Aminoethyl)-7,10-dihydroxy-5-[[2-[(2-hydroxyethyl)amino]ethyl]amino]anthra[1,9-cd]pyrazol-6(2H)-one Reaction of a mixture of 2.0 g (6 mmol) of 2-(2-aminoethyl)-5-chloro-7,10-dihydroxyanthra [1,9-cd]pyrazol-6(2H)-one, 3 ml (30 mmol) of 2-(2-aminoethylamino)ethanol, and 25 ml of pyridine at reflux overnight followed by workup as described in Example 21 and salt formation as described in Example 3 gives 1.3 g of the product as a salt with 2.0 equivalents of hydrogen chloride solvated with 0.5 equivalent of water; mp 275°–280° C. (decomposition).

2-(2-Aminoethyl)-5-chloro-7,10-dihydroxyanthra-[1,9-cd]pyrazol-6(2H)-one is prepared from 2-(2-aminoethyl)-5-chloro-7,10-bis(phenylmethoxy)anthra[1,9-cd]-pyrazol-6(2H)-one and boron trichloride as described in Example 54 to give the product as a salt with 1.0 equivalent of hydrogen chloride solvated with 0.7 equivalent of water; mp 265°–268° C. (decomposition).

2-(2-Aminoethyl)-5-chloro-7,10-bis(phenylmethoxy)anthra[1,9-cd]pyrazol-6(2H)-one is prepared from 1,4-dichloro-5,8-bis(phenylmethoxy)-9,10-anthracenedione and (2-aminoethyl)hydrazine as described in Example 54 to give the product; mp 176°–178° C.

EXAMPLE 72

2-(2-Aminoethyl)-5-[(2-aminoethyl)amino]-7,10-dihydroxyanthra[1,9-cd]pyrazol-6(2H)-one Reaction of 2-(2-aminoethyl)-5-chloro-7,10-dihydroxyanthra[1,9-cd]pyrazol-6(2H)-one with ethylenediamine as described in Example 71 gives the product as a salt with 1.9 equivalents of hydrogen chloride solvated with 1.0 equivalent of water; mp >230° C. (decomposition).

EXAMPLE 73

2-(2-Aminoethyl)-5-[(3-aminopropyl)amino]-7,10-dihydroxyanthra[1,9cd]pyrazol-6(2H)-one Reaction of 2-(2-aminoethyl)-5-chloro-7,10-dihydroxyanthra[1,9-cd]pyrazol-6(2H)-one with 1,3-propanediamine as described in Example 71 gives the product as a salt with 2.9 equivalents of hydrogen chloride solvated with 3.5 equivalents of water; mp >310° C. (decomposition).

EXAMPLE 74

2-[2-Aminoethyl)-5-[[2-[[2-(dimethylamino)ethyl]amino]ethyl]amino]-7,10-dihydroxyanthra[1,9-cd]pyrazol-6(2H)-one Reaction of 2-(2-aminoethyl)-5-chloro-7,10-dihydroxyanthra[1,9-cd]pyrazol-6(2H)-one with N,N-dimethyldiethylenetriamine as described in Example 71 gives the product as a salt with 3.3 equivalents of hydrogen chloride solvated with 1.0 equivalent of water and 0.2 equivalent of 2-propanol; mp 245°–260° C. (decomposition).

EXAMPLE 75

2-(2-Aminoethyl)-5-[[3-[(2-hydroxyethyl)amino]-propyl]amino]-7,10-dihydroxyanthra[1,9-cd]pyrazol-6(2H)-one Reaction of 2-(2-aminoethyl)-5-chloro-7,10-dihydroxyanthra[1,9-cd]pyrazol-6(2H)-one with 2-(3-aminopropylamino)ethanol as described in Example 71 gives the product as a salt with 2.1 equivalents of hydrogen chloride solvated with 1.0 equivalent of water and 0.2 equivalent of 2-propanol; mp 175° C. (decomposition).

EXAMPLE 76

7,10-Dihydroxy-5-[[2-[(2-hydroxyethyl)amino]ethyl]-amino]-2-(2-methoxyethyl)anthra[1,9-cd]pyrazol-6(2H)-one Reaction of a mixture of 2.0 g (5.8 mmol) of 5-chloro-7,10-dihydroxy-2-(2-methoxyethyl)anthra[1,9 cd]pyrazol-6(2H)-one, 5.8 ml (58 mmol) of 2-(2-aminoethylamino)ethanol, and 25 ml of pyridine at 85° C. overnight followed by workup as described in Example 21 gives 1.75 g of product. Salt formation as described in Example 3 gives 1.91 g of product as a salt with 1.1 equivalents of hydrogen chloride solvated with 0.3 equivalent of water and 0.2 equivalent of 2-propanol; mp 68°–72° C.

5-Chloro-7,10-dihydroxy-2-(2-methoxyethyl)anthra[1,9-cd]pyrazol-6(2H)-one is prepared as follows:

Reaction of 11.9 g (23 mmol) of 5-chloro-2-(2-methoxyethyl)-7,10-bis(phenylmethoxy)anthra[1,9-cd]pyrazol-6(2H)-one, 91 ml of a 1 M solution of boron trichloride, and 46 ml of dry dichloromethane as described in Example 24 gives 6.25 g of the dried product; mp 137°–145° C. (decomposition).

5-Chloro-2-(2-methoxyethyl)-7,10-bis(phenylmethoxy)anthra[1,9-cd]pyrazol-6(2H)-one is prepared as follows:

An ice-cold mixture of 3.2 g (6 mmol) of 5-chloro-2-(2-hydroxyethyl)-7,10-bis(phenylmethoxy)anthra[1,9-cd]pyrazol-6(2H)-one, 1.23 ml (20 mmol) of iodomethane, and 20 ml of N,N-dimethylformamide is treated gradually with 0.18 g (8 mmol) of sodium hydride. The ice bath is removed and the mixture is stirred for two hours, treated with five drops of glacial acetic acid, then diluted with water. The solids are filtered, washed sequentially with 2-propanol and diethyl ether to give 2.8 g of the dried product; mp 174°–178° C.

EXAMPLE 77

5-[(2-Aminoethyl)amino]-7,10-dihydroxy-2-(2-methoxyethyl)anthra[1,9-cd]pyrazol-6(2H)-one Reaction of 5-chloro-7,10-dihydroxy-2-(2-methoxyethyl)anthra[1,9-cd]pyrazol-6(2H)-one with ethylenediamine as described in Example 76 gives the product as a salt with 1.0 equivalent of hydrogen chloride solvated with 0.3 equivalent of water; mp 263°–268° C. (decomposition).

EXAMPLE 78

2-(2,3-Dihydroxypropyl)-7,10-dihydroxy-5-[[2-[(2-hydroxyethyl)amino]ethyl]amino]anthra[1,9-cd]pyrazol-6(2H)-one A mixture of 1.3 g (2 mmol) of 2-[(2,2-dimethyl-1,3-dioxolan-4-yl)methyl]-5-[[2-[(2-hydroxyethyl)amino]ethyl]amino-7,10-bis(phenylmethoxy)anthra-[1,9-cd]pyrazol-6(2H)-one, 260 mg of 20% palladium hydroxide on carbon, and 25 ml of glacial acetic acid is stirred under an atmosphere of hydrogen for two hours. The mixture is filtered and concentrated to a residue which is dissolved in methanolic hydrogen chloride. The mixture is stirred at room temperature for two hours and concentrated to a solid which is crystallized from 1:1 methanol:ethanol to give 0.7 g of the product as a salt with 1.1 equivalents of hydrogen chloride solvated with 1.0 equivalent of water; mp >110° C.

2-[(2,2-Dimethyl-1,3-dioxolan-4-yl)methyl]-5-[[2-[(2-hydroxyethyl)amino]ethyl]amino-7,10-bis(phenylmethoxy)anthra[1,9-cd]pyrazol-6(2H)-one is prepared as follows:

A mixture of 1.2 g (2 mmol) of 5-chloro-2-[(2,2-dimethyl-1,3-dioxolan-4-yl)methyl]-7,10-bis(phenylmethoxy)anthra[1,9-cd]pyrazol-6(2H)-one, 2.2 ml (22 mmol) of 2-(2-aminoethylamino)ethanol, 17 ml of pyridine, and 0.3 g of anhydrous potassium carbonate is stirred at reflux for 42 hours. The mixture is diluted with water and filtered to give a solid that is purified by silica gel chromatography utilizing 94:5:1 dichloromethane:methanol:triethylamine. Concentration of the product fractions followed by trituration with 2-propanol gives 730 mg of pure product; mp 206° C.

5-Chloro-2-[(2,2-dimethyl-1,3-dioxolan-4-yl)methyl]-7,10-bis(phenylmethoxy)anthra[1,9-cd]pyrazol-6(2H)-one is prepared as follows:

A mixture of 19.6 g (40 mmol) of 1,4-dichloro-5,8-bis(phenylmethoxy)-9,10-anthracenedione, 10 g (68 mmol) of 4-(hydrazinomethyl)-2,2-dimethyl-1,3-dioxolan [Ann. 448; 121 (1926)], 4 g (69 mmol) of anhydrous potassium fluoride, 5.5 g (40 mmol) of anhydrous potassium carbonate, and 150 ml of dry dimethylsulfoxide is stirred at 80° C. for six hours. The mixture is diluted with water and the solids are filtered, then dissolved in dichloromethane. Chromatography of the dried dichloromethane layer over silica gel with gradient elution utilizing 0.5 to 1% methanol in dichloromethane gives 6 g of a solid that is triturated from 2-propanol, then crystallized from toluene to afford 1.8 g of pure product; mp 184°–188° C.

EXAMPLE 79

2-[2-(Diethylamino)ethyl]-7-[[2-[(2-hydroxyethyl)amino]ethyl]amino]anthra[1,9-cd]pyrazol-6(2H)-one Reaction of 2.5 g (7 mmol) of 7-chloro-2-[2-(diethylamino)ethyl]anthra[1,9-cd]pyrazol-6(2H)-one, 7 ml (70 mmol) of 2-(2-aminoethylamino)ethanol, and 20 ml of pyridine for 20 hours at reflux followed by workup as described in Example 9 gives 1.6 g of a solid, mp 104°–107° C., after recrystallization from toluene. Salt formation as described in Example 3 gives 1.6 g of the dried product as a salt with 2.0 equivalents of hydrogen chloride solvated with 1.1 equivalents of water; mp 212°–216° C. (decomposition).

7-Chloro-2-[2-(diethylamino)ethyl]anthra[1,9-cd]pyrazol6(2H)-one is prepared as follows:

A mixture of 13.85 g (50 mmol) of 1,5-dichloro-9,10-anthracenedione, 13.1 g (100 mmol) of (2-diethylaminoethyl)hydrazine, and 100 ml of pyridine is stirred at 50° C. for five hours, treated with an additional 10 ml of the substrate hydrazine, stirred at 35° C. for 48 hours, cooled, filtered, and concentrated. Trituration of the residue with 2-propanol:ethanol gives 8 g of a solid powder; mp 129°–132° C. Dissolution of a 0.9 g sample in hot methanol followed by salt formation as described in Example 3 gives 0.8 g of the dried product as a salt with 1.0 equivalent of hydrogen chloride; mp 272°–275° C. (decomposition).

EXAMPLE 80

2-[2-(Diethylamino)ethyl]-7-[[2-(diethylamino)ethyl]amino]anthra[1,9-cd]pyrazol-6(2H)-one Reaction of a mixture of 2.1 g (6 mmol) of 7-chloro-2-[2-(diethylamino)ethyl]anthra[1,9-cd]pyrazol-6(2H)-one, 5 ml (36 mmol) of N,N-diethylethylenediamine, and 20 ml of pyridine for 28 hours at reflux followed by workup as described for Example 21 gives 1.9 g of the dried product as a salt with 2.0 equivalents of hydrogen chloride solvated with 0.2 equivalent of water; mp 292°–294° C. (decomposition).

EXAMPLE 81

2-[2-[(2-Hydroxyethyl)amino]ethyl]-7-[[2-[(2-hydroxyethyl)amino]ethyl]amino]anthra[1,9-cd]pyrazol-6-(2H)-one A mixture of 1.9 g (5 mmol) of 7-chloro-2-[2-[(2-hydroxyethyl)amino]ethyl]anthra[1,9-cd]pyrazol-6(2H)-one, 2.0 ml (20 mmol) of 2-(2-aminoethylamino)ethanol, and 20 ml of pyridine is heated at reflux for 72 hours. The mixture is cooled, concentrated, and chromatographed over silica gel with 0.5% triethylamine in dichloromethane, utilizing a gradient elution of 2–10% methanol, to give the product. Salt formation as described in Example 3 gives 500 mg of the product as a salt with 2.0 equivalents of hydrogen chloride solvated with 0.4 equivalent of water; mp 285°–287° C. (decomposition).

7-Chloro-2-[2-[(2-hydroxyethyl)amino]ethyl]anthra[1,9-cd]pyrazol-6(2H)-one is prepared as follows:

A mixture of 11.1 g (40 mmol) of 1,5-dichloro-9,10-anthracenedione, 13.1 g (110 mmol) of 2-[(hydrazinoethyl)amino]ethanol, 4 g of anhydrous potassium bicarbonate, 1 g of anhydrous potassium fluoride, and 110 ml of dimethyl sulfoxide is stirred at 70° C. overnight. The mixture is chilled and the solids are collected by filtration, washed with water, then thoroughly with acetonitrile to give a residue that is crystallized from 2-propanol to leave 2.6 g of product. The hydrochloride salt is prepared as described in Example 3; mp 272°–273° C. (decomposition).

EXAMPLE 82

7,10-Dichloro-2-[2-[(2-hydroxyethyl)amino]ethyl]-5-[[2-[(2-hydroxyethyl)amino]ethyl]amino]anthra[1,9-cd]pyrazol-6(2H)-one Reaction of 7,10-dichloro-2-[2-[(2-hydroxyethyl)amino]ethyl]-5-[[(4-methylphenyl)sulfonyl]oxy]anthra[1,9-cd]pyrazol-6(2H)-one, hydrochloride, with 2-(2-aminoethylamino)ethanol gives the product.

7,10-Dichloro-2-[2-[(2-hydroxyethyl)amino]ethyl]-5-[[(4-methylphenyl)sulfonyl]oxy]anthra[1,9-cd]pyrazol-6(2H)-one is prepared as follows:

To a suspension of 30.9 g (50 mmol) of 1,4-dichloro-5,8-bis[[(4-methylphenyl)sulfonyl]oxy]-9,10-anthracenedione, 13 ml (75 mmol) of N,N-diisopropylethylamine, and 130 ml of N,N-dimethylformamide at 5° C. is added dropwise 14.9 g (125 mmol) of 2-[(hydrazinoethyl)amino]ethanol in 70 ml of N,N-dimethylformamide. The mixture is allowed to reach 10° C. during five hours, then is diluted with 20 ml of acetone. After warming to room temperature, the solution is concentrated to an oil that is distributed between water and dichloromethane. Concentration of the dried dichloromethane layer followed by salt formation as described in Example 3 gives 18.1 g of the dried product as the hydrochloride salt; mp 158°–160° C.

1,4-Dichloro-5,8-bis[[(4-methylphenyl)sulfonyl]oxy]9,10-anthracenedione is prepared as follows:

A mixture of 9.3 g (30 mmol) of 1,4-dichloro-5,8-dihydroxy-9,10-anthracenedione, 12.6 g (66 mmol) of p-toluenesulfonyl chloride, 12.2 ml (70 mmol) of N,N-diisopropylethylamine, and 120 ml of acetonitrile is heated at 70° C. for one hour, then cooled. The crystals are collected by filtration to leave 14.4 g of dried product; mp 195.5°–196.5° C. Processing of the filtrates gives 2.2 g of additional product; mp 190°–192° C.

EXAMPLE 83

7-Hydroxy-2-[2-[(2-hydroxyethyl)amino]ethyl]-5-[[2-[(2-hydroxyethyl)amino]ethyl]amino]anthra[1,9-cd]pyrazol-6(2H)-one Reaction of a mixture of 2-[2-[(2-hydroxyethyl)amino]ethyl]-5-[[2-[(2-hydroxyethyl)amino]ethyl]amino]-7-(phenylmethoxy)anthra[1,9-cd]pyrazol-6(2H)-one with hydrogen and 20% palladium hydroxide on carbon as described in Example 78 gives the product as a salt with 2.0 equivalents of hydrogen chloride solvated with 2.3 equivalents of water; mp 265°–270° C. (decomposition).

2-[2-[(2-hydroxyethyl)amino]ethyl]-5-[[2-[(2-hydroxyethyl)amino]ethyl]amino-7-(phenylmethyoxy)anthra[1,9-cd]pyrazol-6(2H)-one is prepared as follows:

Reaction of 5-chloro-2-[2-[(2-hydroxyethyl)amino]ethyl]-7-(phenylmethoxy)anthra[1,9-cd]pyrazol-6(2H)-one with 2-(2-aminoethylamino)ethanol as described in Example 78 gives the product; mp 157°–159° C.

5-Chloro-2-[2-[(2-hydroxyethyl)amino]ethyl]-7-(phenylmethoxy)anthra[1,9-cd]pyrazol-6(2H)-one is prepared as follows:

A mixture of 4.2 g (11.0 mmol) of 1,4-dichloro-5-(phenylmethoxy)-9,10-anthracenedione, 2.6 g (22.0 mmol) of 2-[(hyrazinoethyl)amino]ethanol, 320 mg (5.5 mmol) of anhydrous potassium fluoride, 1.1 g (11.0 mmol) of anhydrous potassium bicarbonate, and 33 ml of dimethylsulfoxide is stirred overnight at 80° C. The mixture is cooled and poured into water. The aqueous mixture is centrifuged and the aqueous phase is decanted to leave an oil that is dried and purified on silica gel utilizing 4:1 dichloromethane:methanol as eluting solvent. Concentration of the product fractions followed by trituration from methanol gives 840 mg of the dried product; mp 141°–145° C.

1,4-Dichloro-5-(phenylmethoxy)-9,10-anthracenedione is prepared as follows:

A mixture of 5.33 g (18 mmol) of 1,4-dichloro-5-hydroxy-9,10-anthracenedione (British Pat. No. 1,029,448), 2.6 g (19 mmol) of powdered anhydrous potassium carbonate, 2.5 ml (21 mmol) of benzyl bromide, and 75 ml of dry acetone is heated at reflux overnight. The mixture is cooled and the solids are washed well with acetone. Concentration of the filtrates gives a solid which is triturated with ether to afford 5.8 g of the dried product; mp 118°–122° C.

Prepared in a fashion similar to Example 83 is the following:

EXAMPLE 84

7-Hydroxy-2-[2-[(2-hydroxyethyl)-amino]ethyl)-5-[[2-(methylamino)ethyl]amino]anthra[1,9-cd]pyrazol-6(2H)-one as a salt with 1.8 equivalents of hydrogen chloride solvated with 1.2 equivalents of water; mp 280°–282° C. (decomposition) is prepared from 2-[2-[(2-hydroxyethyl)amino]ethyl]-5-[[2-[methyl(phenylmethyl)amino]ethyl]amino]-7-(phenylmethoxy)anthra[1,9-cd]pyrazol-6(2H)-one; mp 110°–113° C., which is prepared from the reaction of N-methyl-N-(phenylmethyl)-1,2-ethanediamine (U.S. Pat. No. 3,201,459) with 5-chloro-2-[2-[(2-hydroxyethyl)amino]ethyl]-7-(phenylmethoxy)anthra[1,9-cd]pyrazol-6(2H)-one.

EXAMPLE 85

10-Hydroxy-2-[2-[(2-hydroxyethyl)amino]ethyl]-5-[[2-[(2-hydroxyethyl)amino]ethyl]amino]anthra-1[1,9-cd]-pyrazol-6(2H)-one Reaction of a mixture of 2-[2-[(2-hydroxyethyl)amino]ethyl]-5-[[2-[(2-hydroxyethyl)amino]ethyl]amino]-10-(phenylmethoxy)anthra[1,9-cd]pyrazol-6(2H)-one with hydrogen and 20% palladium hydroxide on carbon as described in Example 78 gives the product as a salt with 2.1 equivalents of hydrogen chloride solvated with 0.8 equivalent of water; mp 260°–267° C. (decomposition).

2-[2-[(2-hydroxyethyl)amino]ethyl]-5-[[2-[(2-hydroxyethyl)amino]ethyl]amino-10-(phenylmethoxy)anthra[1,9-cd]pyrazol-6(2H)-one is prepared as follows:

Reaction of 5-chloro-2-[2-[(2-hydroxyethyl) amino]ethyl]-10-(phenylmethoxy)anthra[1,9-cd]pyrazol-6(2H)-one with 2-(2-aminoethylamino)ethanol as described in Example 78 gives the product; mp 178°–180° C.

5-Chloro-2-[2-[(2-hydroxyethyl)amino]ethyl]-10-(phenylmethoxy)anthra[1,9-cd]pyrazol-6(2H)-one is prepared as follows:

Reaction of 1,4-dichloro-5-(phenylmethoxy)-9,10-anthracenedione with 2-[(hydrazinoethyl)amino]ethanol as described in Example 83 gives the product as the minor isomer; mp 165°–167° C.

EXAMPLE 86

7,9,10-Trihydroxy-2-[2-[(2-hydroxyethyl)amino]ethyl]-5-[[2-[(2-hydroxyethyl)amino]ethyl]amino]anthra[1,9-cd]-pyrazol-6(2H)-one Reaction of a solution of 2-[2-[(2-hydroxyethyl)amino]ethyl]-5-[[2-[(2-hydroxyethyl)amino]ethyl]amino]-7,9,10-tris(phenylmethoxy)anthra[1,9-cd]pyrazol-6(2H)-on e in glacial acetic acid with hydrogen and 20% palladium hydroxide on carbon as described in Example 78 gives the product as a salt with 2.1 equivalents of hydrogen chloride solvated with 0.8 equivalent of water; mp >235° C. (decomposition).

2-[2-[(2-Hydroxyethyl)amino]ethyl]-5-[[2-[(2-hydroxyethyl)amino]ethyl]amino]-7,9,10-tris(phenylmethoxy)anthra[1,9-cd]pyrazol-6(2H)-one is prepared as follows:

A mixture of 660 mg (1 mmol) of 5-chloro-2-[2-[(2-hydroxyethyl)amino]ethyl]-7,9,10-tris (phenylmethoxy)anthra[1,9-cd]pyrazol-6(2H)-one, 1 ml (10 mmol) of 2-(2-aminoethylamino)ethanol, and 2 ml of pyridine is heated at reflux for 28 hours. Workup as described in Example 21 gives a solid whose crystallization from acetonitrile:chloroform affords 308 mg of product; mp 158°–159° C.

5-Chloro-2-[2-[(2-hydroxyethyl)amino]ethyl]-7,9,10-tris(phenylmethoxy)anthra[1,9-cd]pyrazol-6(2H)-one is prepared as follows:

A suspension of 7.2 g (12 mmol) of 5,8-dichloro-1,2,4-tris(phenylmethoxy)-9,10-anthracenedione, 2.9 g (24 mmol) of 2-[(hydrazinoethyl)amino]ethanol, 350 mg (6 mmol) of anhydrous potassium flouride, 1.2 g (12 mmol) of anhydrous potassium bicarbonate, and 25 ml of dimethylsulfoxide is stirred overnight at 75° C. The mixture is cooled, then triturated with 2-propanol. The solids are filtered, washed well with water, 2-propanol, then crystallized from chloroform to give 2.3 g of orange solid; mp 172°–173° C.

Processing of the nonaqueous filtrates gives 640 mg of additional product corresponding to ca. 1:1 mixture of isomers by $^1$H NMR; mp 135°–140° C.

5,8-Dichloro-1,2,4-tris(phenylmethoxy)-9,10-anthracenedione is prepared is as follows:

A suspension of 7.5 g (23 mmol) of 5,8-dichloro-1,2,4-trihydroxy-9,10-anthracenedione, 9.6 ml (81 mmol) of benzyl bromide, 9.9 g (72 mmol) of powdered anhydrous potassium carbonate, 0.4 ml of methanol, 92 ml of acetone, and 46 ml of N,N-dimethylformamide is heated at reflux under argon for two days. An additional 2.7 ml of benzyl bromide is added and the mixture is heated for three days. The suspension is filtered and the filtrate is concentrated to an oil which is distributed between dichloromethane and 10% aqueous acetic acid. The dried dichloromethane layer is concentrated to a solid whose crystallization from ethyl acetate affords 7.2 g of product; mp 174°–175° C.

5,8-Dichloro-1,2,4-trihydroxy-9,10-anthracenedione is prepared as follows:

A suspension of 451 mg (1 mmol) of 1,2,4-tris (acetyloxy)-5,8-dichloro-9,10-anthracenedione, 5 ml of glacial acetic acid, and 5 ml of 6 N aqueous hydrochloric acid is heated at 70° C. for one hour. The suspension is cooled and the solids are filtered off. After washing with water and drying, there remains 287 mg of the dried product; mp 290°–295° C. (decomposition).

1,2,4-Tris(acetyloxy)-5,8-dichloro-9,10-anthracenedione is prepared as follows:

A suspension of 307 mg (1 mmol) of 5,8-dichloro-1,4,9,10-anthracenetetrone, 0.05 ml of 72% perchloric acid, and 10 ml of acetic anhydride is stirred at room temperature for 30 minutes. The solution is diluted with water, the organic layer is separated, and dried, then concentrated to a solid residue. Trituration of the solid from ethyl acetate leaves 235 mg of product; mp 205°–206° C.

5,8-Dichloro-1,4,9,10-anthracenetetrone is prepared as follows:

A suspension of 618 mg (2 mmol) of 1,4-dichloro-5,8-dihydroxy-9,10-anthracenedione, 1.06 g (2.4 mmol) of lead tetraacetate, and 25 ml of glacial acetic acid is stirred at room temperature for 45 minutes. The mixture is treated with 0.5 ml ethylene glycol, and after 15 minutes is diluted with dichloromethane. The mixture is washed with water and the dried organic layer is evaporated to a solid. Trituration of the solid from diethyl ether gives 569 mg of product; mp 255°–257° C. (decomposition).

EXAMPLE 87

7,8,10-Trihydroxy-2-[2-[(2-hydroxethyl)amino]ethyl]-5-[[2-[(2-hydroxyethyl)amino]ethyl]amino]anthra[1,9-cd]pyrazol-6(2H)-one Reaction of a solution of 2-[2-[(2-hydroxyethyl)amino]ethyl]-5-[[2-[(2-hydroxyethyl)amino]ethyl]amino]-7,8,10-tris(phenylmethoxy)anthra[1,9-cd]pyrazol-6(2H)-on e in glacial acetic acid with hydrogen and 20% palladium hydroxide on carbon as described in Example 78 gives the product as a salt with 2.1 equivalents of hydrogen chloride solvated with 0.6 equivalent of water; mp >210° C. (decomposition).

2-[2-[(2-Hydroxyethyl)amino]ethyl]-5-[[2-[(2-hydroxyethyl)amino]ethyl]amino]-7,8,10-tris(phenylmethoxy)anthra[1,9-cd]pyrazol-6(2H)-one is prepared as follows:

Reaction of 5-chloro-2-[2-[(2-hydroxyethyl)amino]ethyl]-7,8,10-tris(phenylmethoxy)anthra[1,9-cd] pyrazol-6(2H)-one with 2-(2-aminoethylamino)ethanol as described in Example 86 gives the product; mp 186°–188° C.

5-Chloro-2-[2-[(2-hydroxyethyl)amino]ethyl]-7,8,10-tris(phenylmethoxy)anthra[1,9-cd]pyrazol-6(2H)-one is prepared as follows:

Reaction of 5,8-dichloro-1,2,4-tris(phenylmethoxy)-9,10-anthracenedione with 2-[(hydrazinoethyl)amino]ethanol as described in Example 86 gives the product as the minor isomer; mp 164°–167° C.

Prepared in a fashion similar to Example 87 is the following:

EXAMPLE 88

7,8,10-Trihydroxy-2-[2-[(2-hydroxyethyl)amino)]ethyl]-5-[[2-(methylamino)ethyl]amino]anthra[1,9-cd]-pyrazol-6(2H)-one as a salt with 2.0 equivalents of hydrogen chloride solvated with 0.7 equivalent of water; mp>220° C. (decomposition), which is prepared from 2-[2-[(2-hydroxyethyl)amino]ethyl]-5-[[2-[methyl(phenylmethyl)amino]ethyl]amino]-7,8,10-tris (phenylmethoxy)anthra[1,9-cd]pyrazol-6(2H)-one; mp 104°–108° C. which is prepared from the reaction of N-methyl-N(phenylmethyl)-1,2-ethanediamine with 5-chloro-2-[2-[(2-hydroxyethyl)amino]ethyl]-7,8,10-tris(phenylmethoxy)anthra[1,9-cd]pyrazol-6(2H)-one.

EXAMPLE 89

5-[[2-[(2-Aminoethyl)amino]ethyl]amino]-7,10-dihydroxy-2-(2-hydroxyethyl)anthra[1,9-cd]-pyrazol-6(2H)-one Reaction of a solution of 5-[[2-[(2-aminoethyl)amino]ethyl]amino-2-(2-hydroxyethyl)-7,10-bis(-phenylmethoxy)anthra[1,9-cd]pyrazol-6(2H)-one in glacial acetic acid with hydrogen and 20% palladium hydroxide on carbon as described in Example 78 gives the product as a salt with 2.4 equivalents of hydrogen chloride solvated with 0.8 equivalent of water; mp 170°–185° C. (decomposition).

5-[[2-[(2-Aminoethyl)amino]ethyl]amino-2-(2-hydroxyethyl)-7,10-bis(phenylmethoxy)anthra[1,9-cd]-pyrazol-6(2H)-one is prepared as follows:

A mixture of 5.1 g (10 mmol) of 5-chloro-2-(2-hydroxyethyl)-7,10-bis(phenylmethoxy)anthra[1,9-cd]-pyrazol-6(2H)-one, 10 g (100 mmol) of diethylenetriamine, 1.4 g (10 mmol) of anhydrous potassium carbonate, and 60 ml of pyridine is heated at reflux for 28 hours. The mixture is cooled, the solids are collected by filtration then washed sequentially with water and 2-propanol to give 3.1 g of the product; mp 185°–190° C.

EXAMPLE 90

2-(3-Aminopropyl)-7,10-dihydroxy-5-[[2-[(2-hydroxyethyl)amino]ethyl]amino]anthra[1,9-cd]pyrazol-6(2H)-one Reaction of a solution of 1.2 g (2 mmol) of 2-(3-aminopropyl)-5-[[2-[(2-hydroxyethyl)amino]ethyl]-amino]-7,10-bis(phenylmethoxy)anthra[1,9-cd]pyrazol-6(2H)-one in glacial acetic acid with hydrogen and 20% palladium hydroxide on carbon as described in Example 78 followed by salt formation as described in Example 3 gives 850 mg of the product a salt with 2.0 equivalents of hydrogen chloride solvated with 1.1 equivalents of water; mp 292°–294° C. (decomposition).

2-(3-Aminopropyl)-5-[[2-[(2-hyroxyethyl)amino]ethyl]amino-7,10-bis(phenylmethoxy)anthra[1,9-cd]pyrazol-6(2H)-one is prepared as follows:

A mixture of 530 mg (1 mmol) of 2-(3-aminopropyl)-5-chloro-7,10-bis(phenylmethoxy)anthra-1,9-cd]pyrazol-6(2H)-one, 1 ml (10 mmol) of 2-(2-aminoethylamino)ethanol, 140 mg (1 mmol) of anhydrous potassium carbonate, and 8 ml of pyridine is heated at reflux for 22 hours. Workup as described in Example 89 gives 400 mg of the product; mp 191°–195° C.

2-(3-Aminopropyl)-5-chloro-7,10-bis-(phenylmethoxy)anthra[1,9-cd]pyrazol-6(2H)-one is prepared as follows:

Reaction of a mixture of 1,4-dichloro-5,8-bis-(phenylmethoxy)-9,10-anthracenedione and (3-aminopropyl)-hydrazine [*Helvetica Chimica Acta* 42; 533 (1959)] as described in Example 54 gives the product; mp 180°–184° C.

Prepared in a fashion similar to Example 90 is the following:

EXAMPLE 91

2-(3-Aminopropyl)-5-[[2-[[2-(dimethylamino)ethyl]-amino]ethyl]amino]-7,10-dihydroxyanthra[1,9-cd]pyrazol-6(2H)-one as a salt with 3.0 equivalents of hydrogen chloride solvated with 2.0 equivalents of water; mp 294° C. (decomposition), which is prepared from 2-(3-aminopropyl)-5-[[2-[[2-(dimethylamino)ethyl]amino]ethyl]amino]-7,10-bis(phenylmethoxy)anthra[1,9-cd]pyrazol-6(2H)-one; mp 143°–160° C., which is prepared from the reaction of N,N-dimethyldiethylenetriamine with 2-(3-aminopropyl)-5-chloro-7,10-bis(phenylmethoxy)anthra[1,9-cd]pyrazol-6(2H)-one.

EXAMPLE 92

2-(2-Aminoethyl)-7,10-dihydroxy-5-[[2-(methylamino)ethyl]amino]anthra[1,9-cd]pyrazol-6(2H)-one Reaction of a mixture of 2-(2-aminoethyl)-5-[[2-methyl(phenylmethyl)amino]ethyl]amino]-7,10-bis-(phenylmethoxy)anthra[1,9-cd]pyrazol-6(2H)-one with hydrogen and 20% palladium hydroxide on carbon as described in Example 78 gives the product as a salt with 2.2 equivalents of hydrogen chloride solvated with 0.5 equivalent of water; mp 259°–264° C. (decomposition).

2-(2-Aminoethyl)-5-[[2-[methyl(phenylmethyl)amino]ethyl]amino]-7,10-bis(phenylmethoxy)anthra[1,9-cd]pyrazol-6(2H)-one is prepared as follows:

Reaction of 2-(2-aminoethyl)-5-chloro-7,10-bis-(phenylmethoxy)anthra[1,9-cd]pyrazol-6(2H)-one with N-methyl-N-(phenylmethyl)-1,2-ethanediamine as described in Example 78 gives the product; mp 169°–172° C.

EXAMPLE 93

7,10-Dihydroxy-5-[[2-[(2-hydroxyethyl)amino]ethyl]amino]-2-[2-(methylamino)ethyl]anthra[1,9-cd]pyrazol-6(2H)-one Reaction of a mixture of 5-[[2-[(2-hydroxyethyl)amino]ethyl]amino]-2-[2-(methylamino)ethyl]-7,10-bis-(phenylmethoxy)anthra[1,9-cd]pyrazol-6(2H)-one with hydrogen and 20% palladium hydroxide on carbon as described in Example 78 gives the product as a salt with 2.0 equivalents of hydrogen chloride solvated with 1.8 equivalents of water; mp 180°–185° C. (decomposition).

5-[[2-[(2-hydroxyethyl)amino]ethyl]amino]-2-[2-(methylamino)ethyl]-7,10-bis(phenylmethoxy)anthra[1,9-cd]pyràzol-6(2H)-one is prepared as follows:

Reaction of 5-chloro-2-[2-(methylamino)ethyl]-7,10-bis(phenylmethoxy)anthra[1,9-cd]pyrazol-6(2H)-one with 2-(2-aminoethylamino)ethanol as described in Example 78 gives the product; mp 186°–189° C.

5-Chloro-2-[2-(methylamino)ethyl]-7,10-bis-(phenylmethoxy)anthra[1,9-cd]pyrazol-6(2H)-one is prepared as follows:

Reaction of 5-chloro-2-[3-[[(4-methylphenyl)sulfonyl]oxy]ethyl]-7,10-bis(phenylmethoxy)anthra[1,9-cd]pyrazol-6(2H)-one with methylamine as described in Example 51 gives the product; mp 171°–176° C.

EXAMPLE 94

5-[(2-Aminoethyl)amino]-2-[3-(dimethylamino)propyl]-7,10-dihydroxyanthra[1,9-cd]pyrazol-6(2H)-one Reaction of 5-chloro-2-[3-(dimethylamino)propyl]-7,10-dihydroxyanthra[1,9-cd]pyrazol-6(2H)-one, hydrochloride, with ethylenediamine as described in Example 46 gives the product as a salt with 2.0 equivalents of hydrogen chloride solvated with 0.5 equivalent of water and 0.1 equivalent of 2-propanol; mp 316° C. (decomposition).

EXAMPLE 95

7,8-Dihydroxy-2-[2-[(2-hydroxyethyl)amino]ethyl]-5-[[2-[(2-hydroxyethyl)amino]ethyl]amino]anthra[1,9-cd]pyrazol-6(2H)-one Reaction of a mixture of 2-[2-[(2-hydroxyethyl)amino]ethyl]-5-[[2-[(2-hydroxyethyl)amino]ethyl]amino]-7,8-bis(phenylmethoxy)anthra[1,9-cd]pyrazol-6(2H)-one with hydrogen and 20% palladium hydroxide on carbon as described in Example 78 gives the product.

2-[2-[(2-hydroxyethyl)amino]ethyl]-5-[[2-[(2-hydroxyethyl)amino]ethyl]amino]-7,8-bis-(phenylmethoxy)anthra[1,9-cd]pyrazol-6(2H)-one is prepared as follows:

Reaction of 5-chloro-2-[2-[(2-hydroxyethyl)amino]ethyl]-7,8-bis(phenylmethoxy)anthra[1,9-cd]-pyrazol-6(2H)-one with 2-(2-aminoethylamino)ethanol as described in Example 78 gives the product.

5-Chloro-2-[2-[(2-hydroxyethyl)amino]ethyl]-7 8-bis(phenylmethoxy)anthra[1,9-cd]pyrazol-6(2H)-one is prepared as follows:

Reaction of 1,4-dichloro-5,6-bis(phenylmethoxy)-9,10-anthracenedione with 2-[(hydrazinoethyl)amino]ethanol as described in Example 54 gives the product.

1,4-Dichloro-5,6-bis(phenylmethoxy)-9,10-anthracenedione is prepared as follows:

Reaction of 1,4-dichloro-5,6-dihydroxy-9,10-anthracenedione with benzyl bromide as described in Example 48 gives the product.

1,4-Dichloro-5,6-dihydroxy-9,10-anthracenedione is prepared as follows:

Reaction of nitrosyl sulfuric acid and 5,6-diamino-1,4-dichloro-9,10-anthracenedione [*Khim. Geterotsikl. Soedin.* 808 (1968)] gives the product.

We claim:

1. A compound having the structural formula

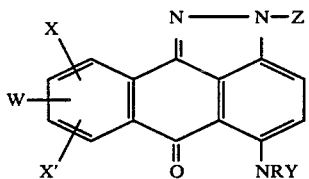

wherein X, X', and W may be the same or different and are H, OH, alkoxy of one to four carbon atoms or chlorine; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an NRaRa wherein Ra may be the same or different and is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may form

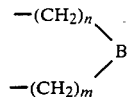

wherein n and m may be the same or different and are one, two, or three provided that the sum of n and m is such as to form a five or six-membered ring and B is a direct bond, O, S, or N-$R_4$ wherein $R_4$ is H or alkyl of from one to six carbon atoms; R and Y when taken together may form

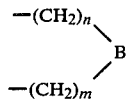

wherein n, m, and B are defined above; Z is alkyl of from one to six carbon atoms substituted with an $N(R_1)_2$, $SR_1$, or $OR_1$ group wherein $R_1$ is the same or different and is defined above, or $DNR_2R_3$ wherein D is straight or branched alkylene of from two to eight carbon atoms which may be substituted with an OH group and $R_2$ and $R_3$ are as defined above; or a pharmaceutically acceptable salt thereof.

2. A compound having the structural formula

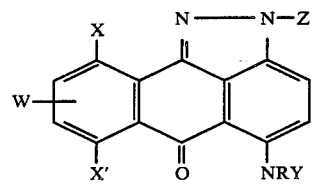

wherein X, X', and W may be the same or different and are H or OH, alkoxy of one to four carbon atoms or chlorine; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an NRaRa wherein Ra may be the same or different is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may form

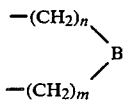

wherein n and m may be the same or different and are one, two, or three provided that the sum of n and m is such as to form a five- or six-membered ring and B is a direct bond, O, S, or N-$R_4$ wherein $R_4$ is H or alkyl of from one to six carbon atoms; R and Y when taken together may form

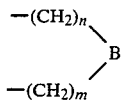

wherein n, m, and B are defined above; Z is alkyl of from one to six carbon atoms substituted with an $N(R_1)_2$, $SR_1$, or $OR_1$ group wherein $R_1$ is the same or different and is as defined above, or $DNR_2R_3$ wherein D is straight or branched alkylene of from two to eight carbon atoms which may be substituted with an OH group and $R_2$ and $R_3$ are as defined above; or a pharmaceutically acceptable salt thereof.

3. A compound having the structural formula

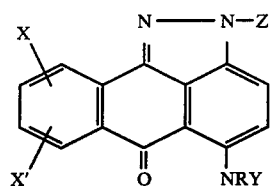

wherein X and X' may be the same or different and are H, OH, alkoxy of one to four carbon atoms or chlorine; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an NRaRa wherein Ra may be the same or different is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may form

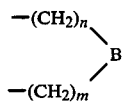

wherein n and m may be the same or different and are one, two, or three provided that the sum of n and m is such as to form a five- or six-membered ring and B is a direct bond, O, S, or N-$R_4$ wherein $R_4$ is H or alkyl of from one to six carbon atoms; R and Y when taken together may form

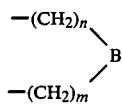

wherein n, m, and B are defined above; Z is alkyl of from one to six carbon atoms substituted with an $N(R_1)_2$, $SR_1$, or $OR_1$ group wherein $R_1$ is the same or different and is as defined above, or $DNR_2R_3$ wherein D is straight or branched alkylene of from two to eight carbon atoms which may be substituted with an OH group and $R_2$ and $R_3$ are as defined above; or a pharmaceutically acceptable salt thereof.

4. A compound having the structural Formula I

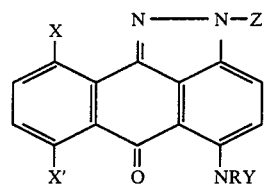

wherein X and X' may be the same or different and are H or OH; R is H or alkyl of from one to six carbon atoms; Y is H, alkyl of from one to six carbon atoms which may be substituted with an $OR_1$ group wherein $R_1$ is H or alkyl of from one to six carbon atoms, or $ANR_2R_3$ wherein A is straight or branched alkylene of from two to eight carbon atoms, $R_2$ and $R_3$ may be the same or different and are H, alkyl of from one to six carbon atoms which may be substituted with OH or an NRaRa wherein Ra may be the same or different is H or alkyl of from one to three carbon atoms which may be substituted with OH, or $NR_bR_b$ wherein $R_b$ is the same or different and is H or alkyl of from one to three carbon atoms, or $R_2$ and $R_3$ when taken together may form

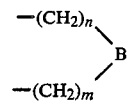

wherein n and m may be the same or different and are one, two, or three provided that the sum of n and m is such as to form a five- or six-membered ring and B is a direct bond, O, S, or N-$R_4$ wherein $R_4$ is H or alkyl of from one to six carbon atoms; R and Y when taken together may form

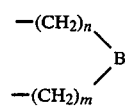

wherein n, m, and B are defined above; Z is alkyl of from one to six carbon atoms substituted with an $N(R_1)_2$, $SR_1$, or $OR_1$ group wherein $R_1$ is the same or different and is as defined above, or $DNR_2R_3$ wherein D is straight or branched alkylene of from two to eight carbon atoms which may be substituted with an OH group and $R_2$ and $R_3$ are as defined above; or a pharmaceutically acceptable salt thereof.

5. A chemical compound defined in claim 4 wherein X and X' are OH; or a pharmaceutically acceptable salt thereof.

6. A chemical compound defined in claim 4 wherein X and X' are H; or a pharmaceutically acceptable salt thereof.

7. A chemical compound defined in claim 4 wherein A and D are the same or different and are ethylene or propylene; or a pharmaceutically acceptable salt thereof.

8. A compound having the structural Formula I'

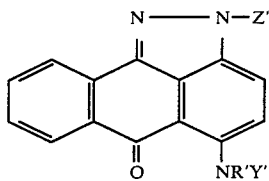  I' wherein R' is H or alkyl of from 1 to 6 carbon atoms; Y' is CH$_2$CH$_2$NHCH$_2$CH$_2$OH when Z' is alkyl of from one to four carbon atoms which may be substituted with an SR$_1$', or OR$_1$' group wherein R$_1$' is H or alkyl of from one to four carbon atoms or D'NR$_2$'R$_3$' wherein D' is straight or branched alkylene of from two to four carbon atoms which may be substituted with an OH group and R$_2$' and R$_3$' may be the same or different and are H, alkyl of from one to six carbon atoms which may be substituted with an OH or R$_2$' and R$_3$' when taken together may form

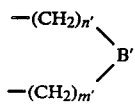

wherein n' and m' may be the same or different and are one or two provided that the sum of n' and m' is such as to form a five- or six-membered ring, and B' is a direct bond, O, S, or N-R$_4$' wherein R$_4$' is H or alkyl of from one to four carbon atoms; or Z' is CH$_2$CH$_2$NHCH$_2$CH$_2$OH when Y' is H, alkyl of from one to six carbon atoms which may be substituted with an OR$_1$' group wherein R$_1$' is defined above or A'NR$_1$'R$_2$' wherein A' is alkylene of from two to four carbon atoms and R$_1$' and R$_2$' are as defined above; or a pharmaceutically acceptable salt thereof.

9. A compound having structural Formula I''

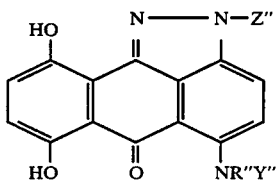  I'' wherein R'' is H or alkyl of from one to six carbon atoms; Y'' is H, alkyl of from one to six carbon atoms which may be substituted with an OR$_1$'' group wherein R$_1$'' is H or alkyl of from one to four carbon atoms, or A''NR$_2$''R$_3$'' wherein A'' is alkylene of from two to four carbon atoms, R$_2$'' and R$_3$'' may be the same or different and are H, alkyl of from one to six carbon atoms which may be substituted with an OH or an NRa''Ra'' wherein Ra'' may be the same or different and is H or alkyl of from one to three carbon atoms which may be substituted with an OH or R$_2$'' and R$_3$'' when taken together may form

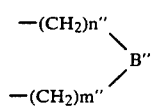

wherein n'' and m'' may be the same or different and are one or two provided that the sum of n'' and m'' is such as to form a five- or six-membered ring, and B'' is a direct bond, O, S, or N-R$_4$'' wherein R$_4$'' is H or alkyl of from one to four carbon atoms; Z'' is alkyl of from one to four carbon atoms which may be substituted with an SR$_1$'', or OR$_1$'' group wherein R$_1$'' is defined above, or D''NR$_2$''R$_3$'' wherein D'' is alkylene of from two to four carbon atoms which may be substituted with an OH group and R$_2$'' and R$_3$'' are as defined above; or a pharmaceutically acceptable salt thereof.

10. A compound having structural Formula I'''

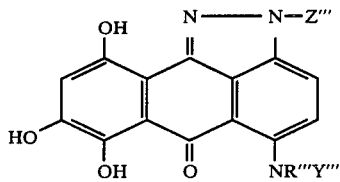  I''' wherein R''' is H or alkyl of from one to six carbon atoms; Y''' is H, alkyl of from one to six carbon atoms which may be substituted with an OR$_1$''' group wherein R$_1$''' is H or alkyl of from one to four carbon atoms, or A'''NR$_2$'''R$_3$''' wherein A''' is alkylene of from two to four carbon atoms, R$_2$''' and R$_3$''' may be the same or different and are H, alkyl of from one to six carbon atoms which may be substituted with an OH or an NRa'''Ra''' wherein Ra''' may be the same or different and is H or alkyl of from one to three carbon atoms which may be substituted with an OH or R$_2$''' and R$_3$''' when taken together may form

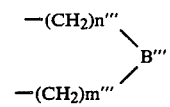

wherein n''' and m''' may be the same or different and are one or two provided that the sum of n''' and m''' is such as to form a five- or six-membered ring and B''' is a direct bond, O, S, or N-R$_4$''' wherein R$_4$''' is H or alkyl of from one to four carbon atoms; Z''' is alkyl of from one to four carbon atoms which may be substituted with an SR$_1$''', or OR$_1$''' group wherein R$_1$''' is defined above, or D'''NR$_2$'''R$_3$''' wherein D''' is alkylene of from two to four carbon atoms which may be substituted with an OH group and R$_2$''' and R$_3$''' are as defined above; or a pharmaceutically acceptable salt thereof.

11. A compound having a structural Formula I''''

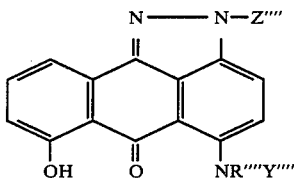  I'''' wherein R'''' is H or alkyl of from one to six carbon atoms; Y'''' is H, alkyl of from one to six carbon atoms which may be substituted with an OR$_1$'''' group wherein R$_1$'''' is H or alkyl of from one to four carbon atoms, or A''''NR$_2$''''R$_3$'''' wherein A'''' is alkylene of from two to four carbon atoms, R$_2$'''' and R$_3$'''' may be the same or different and are H, alkyl of from one to six carbon atoms which may be substituted with an OH or an NRa''''Ra'''' wherein Ra'''' may be the same or different and is H or alkyl of from one to three carbon atoms which may be substituted with an OH or $R_2''''$ and $R_3''''$ when taken together may form

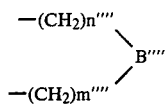

wherein n'''' and m'''' may be the same or different and are one or two provided that the sum of n'''' and m'''' is such as to form a five- or six-membered ring, and B'''' is a direct bond, O, S, or N-$R_4''''$ wherein $R_4''''$ is H or alkyl of from one to four carbon atoms; Z'''' is alkyl of from one to four carbon atoms which may be substituted with an $SR_1''''$, or $OR_1''''$ group wherein $R_1''''$ is defined above, or D''''$NR_2''''R_3''''$ wherein D'''' is alkylene of from two to four carbon atoms which may be substituted with an OH group and $R_2''''$ and $R_3''''$ are as defined above; or a pharmaceutically acceptable salt thereof.

12. A compound defined in claim 4 having the structural Formula $I^v$

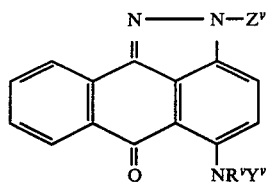

wherein $R^v$ is H or alkyl of from one to six carbon atoms; $Y^v$ is H, alkyl of from one to four carbon atoms or $A^vNR_2^vR_3^v$ wherein $A^v$ is alkylene of from two to four carbon atoms, $R_2^v$ and $R_3^v$ may be the same or different and are H or alkyl of from one to six carbon atoms which may be substituted with an OH or $R_2^v$ and $R_3^v$ when taken together may form

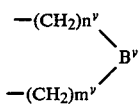

wherein $n^v$ and $m^v$ may be the same or different and are one or two provided that the sum of $n^v$ and $m^v$ is such as to form a five- or six-membered ring, and $B^v$ is a direct bond, O, S, or $NR_4^v$ wherein $R_4^v$ is H or alkyl of from one to four carbon atoms; $Z^v$ is $D^vNR_2^vR_3^v$ wherein $D^v$ is alkylene of from two to four carbon atoms which may be substituted with an OH group and $R_2^v$ and $R_3^v$ are defined above; or a pharmaceutically acceptable salt thereof.

13. A compound defined in claim 4 having the structural Formula $I^{vi}$

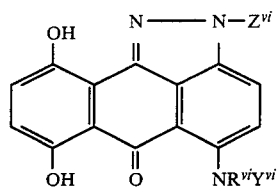

wherein $R^{vi}$ is H or alkyl of from one to six carbon atoms; $Y^{vi}$ is H, alkyl of from one to four carbon atoms which may be substituted with an $OR_1^{vi}$ group wherein $R_1^{vi}$ is H or alkyl of from one to four carbon atoms or $A^{vi}NR_2^{vi}R_3^{vi}$ wherein $A^{vi}$ is alkylene of from two to four carbon atoms $R_2^{vi}$ and $R_3^{vi}$ may be the same or or different and are alkyl of from one to six carbon atoms which may be substituted with an OH, or $R_2^{vi}$ and $R_3^{vi}$ when taken together may form

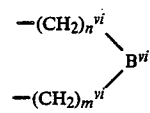

wherein $n^{vi}$ and $m^{vi}$ may be the same or different and are one or two provided that the sum of $n^{vi}$ and $m^{vi}$ is such as to form a five-bond, or six-membered ring, and $B^{vi}$ is a direct O, S, or $NR_4^{vi}$ wherein $R_4^{vi}$ is H or alkyl of from one to four carbon atoms; $Z^{vi}$ is $D^{vi}NR_2^{vi}R_3^{vi}$ wherein $D^{vi}$ is alkylene of from two to four carbon atoms, $R_2^{vi}$ and $R_3^{vi}$ are defined above; or a pharmacuetically acceptable salt thereof.

14. A chemical compound defined in claim 2 and selected from the group consisting of:
2-[2-[(2-hydroxyethyl)amino]ethyl]-5-[[2-[(2-hydroxyethyl)amino]ethyl]amino]anthra[1,9-cd]pyrazol-6(2H)-one;
2-[2-(diethylamino)ethyl]-7,10-dihydroxy-5-[[2-[(2-hydroxyethyl)amino]ethyl]amino]anthra[1,9-cd]pyrazol-6(2H)-one;
2-[2-[[2-(dimethylamino)ethyl]amino]ethyl]-5-[[2-[(2-hydroxyethyl)amino]ethyl]amino]-7,10-dihydroxyanthra[1,9-cd]-pyrazol-6(2H)-one;
5-[(2-aminoethyl)amino]-2-[2-(diethylamino)ethyl]-7,10-dihydroxyanthra[1,9-cd]pyrazol-6(2H)-one; 2-[2-(dimethylamino)ethyl]-7,10-dihydroxy-5-[[2-[(2-hydroxyethyl)amino]ethyl]amino]anthra[1,9-cd]pyrazol-6(2H)-one;
5-[[2-(dimethylamino)ethyl]amino]-7,10-dihydroxy-2-(2-hydroxyethyl)anthra[1,9-cd]pyrazol-6(2H)-one;
5-[(2-aminoethyl)amino]-7,10-dihydroxy-2-[2-[(2-hydroxyethyl)amino]ethyl]anthra[1,9-cd]pyrazol-6(2H)-one;
5-[(3-aminopropyl)amino]-7,10-dihydroxy-2-[2-[(2-hydroxyethyl)amino]ethyl]anthra[1,9-cd]pyrazol-6(2H)-one;
5-[[2-[[2-(dimethylaminoethyl]amino]ethyl]amino]-7,10-dihydroxy-2-[2-[(2-hydroxyethyl)amino]ethyl]-anthra[1,9-cd]-pyrazol-6(2H)-one;
5-[[2-[bis(2-hydroxyethyl)amino]ethyl]amino]-7,10-dihydroxy-2-[2-[(2-hydroxyethyl)amino]ethyl]-anthra[1,9-cd]pyrazol-6(2H)-one;
7,10-dihydroxy-2-[2-[(2-hydroxyethyl)amino]ethyl]-5-[[2-(methylamino)ethyl]amino]anthra[1,9-cd]pyrazol-6(2H)-one;

2-(2-aminoethyl)-7,10-dihydroxy-5-[[2-[(2-hydroxyethyl)amino]ethyl]amino]anthra[1,9-cd]pyrazol-6(2H)-one;

2-(2,3-dihydroxypropyl)-7,10-dihydroxy-5-[[2-[(2-hydroxyethyl)amino]ethyl]amino]anthra[1,9-cd]pyrazol-6(2H)-one;

7-hydroxy-2-[2-[(2-hydroxyethyl)amino]ethyl]-5-[[2-[(2-hydroxyethyl)amino]ethyl]amino]anthra[1,9-cd]pyrazol-6(2H)-one;

7-hydroxy-2-[2-[(2-hydroxyethyl)amino]ethyl]-5-[[2-(methylamino)ethyl]amino]anthra[1,9-cd]pyrazol-6(2H)one;

7,8,10-trihydroxy-2-[2-[(2-hydroxyethyl)amino]ethyl]-5-[[2-[(2-hydroxyethyl)amino]ethyl]amino]anthra[1,9-cd]pyrazol-6(2H)-one;

7,8,10-trihydroxy-2-[2-[(2-hydroxyethyl)amino)]ethyl]-5-[[2-(methylamino)ethyl]amino]anthra[1,9-cd]pyrazol-6(2H)-one;

2-(3-aminopropyl)-7,10-dihydroxy-5-[[2-[(2-hydroxyethyl)amino]ethyl]amino]anthra[1,9-cd]pyrazol-6(2H)-one;

2-(2-aminoethyl)-7,10-dihydroxy-5-[[2-(methylamino)ethyl]amino]anthra[1,9-cd]pyrazol-6(2H)-one;

5-[(2-aminoethyl)amino]-2-[3-(dimethylamino)propyl]-7,10-dihydroxyanthra[1,9-cd]pyrazol(2H)-one, and 7,8-dihydroxy-2-[2-[(2-hydroxyethyl)amino]ethyl]-5-[[2-[(2-hydroxyethyl)amino]ethyl]amino]anthra[1,9-cd]pyrazol-6(2H)-one; or a pharmaceutically acceptable salt thereof.

15. A chemical compound having the structural formula:

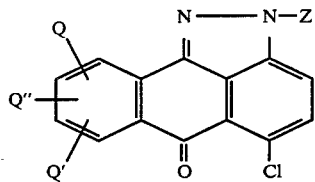

wherein Q, Q' and Q" may be the same or different and are H, OH, benzyloxy, p-chlorobenzyloxy and p-methoxybenzyloxy; Z is defined in claim 1; or a pharmaceutically acceptable salt thereof.

16. A chemical compound having the structural Formula III

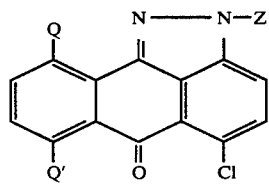

wherein Q and Q' may be the same or different and are H, OH, benzyloxy, p-chlorobenzyloxy, or p-methoxybenzyloxy and Z is defined in claim 1; or a pharmaceutically acceptable salt thereof.

17. A chemical compound defined in claim 16 wherein Q and Q' are H; or a pharmaceutically acceptable salt thereof.

18. A chemical compound defined in claim 16 wherein Q and Q' are benzyloxy, p-chlorobenzyloxy, or p-methoxybenzyloxy; or a pharmaceutically acceptable salt thereof.

19. A chemical compound defined in claim 16 wherein Q and Q' are OH; or a pharmaceutically acceptable salt thereof.

20. A chemical compound defined in claim 15 and selected from the group consisting of 5-chloro-2[2-[(2hydroxyethyl)amino]ethyl]anthra[1,9-cd]-pyrazol-6(2H)-one;

5-chloro-2[2-(diethylamino)ethyl]-7,10-dihydroxyanthra[1,9-cd]-pyrazol-6(2H)-one;

5-chloro-7,10-dihydroxy-2-(2-hydroxyethyl)anthra[1,9-cd]-pyrazol-6(2H)-one;

5-chloro-2[2-(diethylamino)ethyl]-7,10-bis-(phenylmethoxy)-anthra[1,9-cd]pyrazol-6(2H)-one;

5-chloro-7,10-dihydroxy-2-[2-[(2-hydroxyethyl)amino]ethyl]-anthra[1,9-cd]pyrazol-6(2H)-one;

5-chloro-2-[2-[(2-hydroxyethyl)amino]ethyl]-7,10-bis(-phenylmethoxy)anthra[1,9-cd]pyrazol-6(2H)-one;

5-chloro-2-[2-[[2-(dimethylamino)ethyl]amino]-ethyl]-7,10-dihydroxyanthra[1,9-cd]pyrazol6(2H)-one;

5-chloro-2-[2-(dimethylamino)ethyl]-7,10-dihydroxyanthra[1,9-cd]pyrazol-6(2H)-one;

5-chloro-2-[3-(dimethylamino)propyl]-7,10-dihydroxyanthra[1,9-cd]pyrazol-6(2H)-one;

5-chloro-2-(2-hydroxyethyl)-7,10-bis(phenylmethoxy)anthra[1,9-cd]pyrazol-6(2H)-one;

5-chloro-2-(3-hydroxypropyl)-7,10-bis(phenylmethoxy)anthra[1,9-cd]pyrazol-6(2H)-one;

2-(2-aminoethyl)-5-chloro-7,10-dihydroxyanthra[1,9-cd]pyrazol-6(2H)-one;

2-(2-aminoethyl)-5-chloro-7,10-bis(phenylmethoxy)anthra[1,9-cd]pyrazol-6(2H)-one;

5-chloro-2-[2-[(2-hydroxyethyl)amino]ethyl]-7-(phenylmethoxy)anthra[1,9-cd]pyrazol-6(2H)-one;

5-chloro-2-[2-[(2-hydroxyethyl)amino]-ethyl]-10-(phenylmethoxy)anthra[1,9-cd]pyrazol-6(2H)-one;

5-chloro-2-[2-[(2-hydroxyethyl)amino]ethyl]-7,8,10-tris-(phenylmethoxy)anthra[1,9-cd]pyrazol-6(2H)-one;

2-(3-aminopropyl)-5-chloro-7,10-bis(phenylmethoxy)anthra[1,9-cd]pyrazol-6(2H)-one;

5-chloro-2-[2-[(2-hydroxyethyl)amino]ethyl]-7,8-bis(-phenylmethoxy)anthra[1,9-cd]pyrazol-6(2H)-one, and 5-chloro-2-[2-[[2-(dimethylamino)ethyl]amino]-ethyl]-7,10-bis-(phenylmethoxy)anthra[1,9-cd]pyrazol-6(2H)-one; or a pharmaceutically acceptable salt thereof.

21. A compound having the structural Formula IV

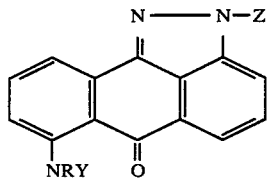

wherein R is H or alkyl of from one to six carbon atoms; Y is alkyl of from one to six carbon atoms substituted with an OR$_1$ group wherein R$_1$ is H or alkyl of from one to six carbon atoms, or ANR$_2$R$_3$ wherein A is alkylene of from two to eight carbon atoms, R$_2$ and R$_3$ may be the same or different and are H, alkyl of from one to six carbon atoms which may be substituted with OH or an NRaRa wherein Ra may be the same or different and is H or alkyl of from one to three carbon atoms which may be substituted with OH, or $R_2$ and $R_3$ when taken together may form

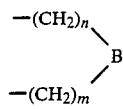

wherein n and m may be the same or different and are one, two, or three, provided that the sum of n and m is such as to form a five- or six-membered ring, and B is a direct bond, O, S, or $N-R_4$ wherein $R_4$ is H or alkyl of from one to six carbon atoms; R and Y when taken together may form

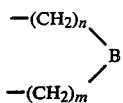

wherein n, m, and B are defined above; Z is alkyl of from one to six carbon atoms substituted with an $N(R_1)_2$, $SR_1$, or $OR_1$ group wherein $R_1$ may be the same or different and is defined above, or $DNR_2R_3$ wherein D is alkylene of from two to eight carbon atoms which may be substituted with an OH group and $R_2$ and $R_3$ are as defined above; or a pharmaceutically acceptable salt thereof.

22. A chemical compound defined in claim 21 and selected from the group consisting of:

2-[2-(diethylamino)ethyl]-7-[[2-[(2-hydroxyethyl)amino]ethyl]amino]anthra[1,9-cd]pyrazol-6(2H)-one;

2-[2-(diethylamino)ethyl-7-[[2-(diethylamino)ethyl]amino]anthra[1,9-cd]pyrazol-6(2H)-one, and 2-[2-[(2-hydroxyethyl)amino]ethyl]-7-[[2-[(2-hydroxyethyl)amino]ethyl]amino]anthra[1,9-cd]pyrazol-6-(2H)-one or a pharmaceutically acceptable salt thereof.

23. A compound having the structural Formula VII

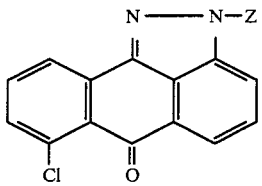

wherein Z is alkyl of from one to six carbon atoms substituted with an $N(R_1)_2$ or $SR_1$ wherein $R_1$ may be the same or different and is H or alkyl of from one to six carbon atoms, or $DNR_2R_3$ wherein D is alkylene of from two to eight carbon atoms which may be substituted with an OH group and $R_2$ and $R_3$ may be the same of different and are H, alkyl of from one to six carbon atoms which may be substituted with OH or an $NR_aR_a$ wherein $R_a$ may be the same or different and is H or alkyl of from one to three carbon atoms which may be substituted with OH, or $R_2$ and $R_3$ when taken together may form

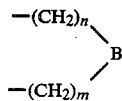

wherein n and m may be the same or different and are one, two, or three, provided that the sum of n and m is such as to form a five- or six-membered ring, and B is a direct bond, O, S, or $N-R_4$ wherein $R_4$ is H or alkyl of from one to six carbon atoms.

24. A chemical compound defined in claim 23 and selected from:

7-chloro-2[2-(diethylamino)ethyl]anthra[1,9-cd]pyrazol-6(2H)-one and 7-chloro-2[2-[(2-hydroxyethyl)amino]ethyl]anthra[1,9-cd]pyrazol-6(2H)-one.

25. An antibacterial composition comprising an effective amount of a compound defined in claim 1 or a pharmaceutically acceptable salt thereof in combination with a pharmaceutically acceptable carrier.

26. A method for treating microbial infections in a mammal which comprises administering an antibacterially effective amount of a compound defined in claim 1 or a pharmaceutically acceptable salts thereof in combination with a pharmaceutically acceptable carrier, to a mammal in need thereof.

* * * * *